United States Patent
Yamaguchi

(10) Patent No.: US 8,243,132 B2
(45) Date of Patent: Aug. 14, 2012

(54) IMAGE OUTPUT APPARATUS, IMAGE OUTPUT METHOD AND IMAGE OUTPUT COMPUTER READABLE MEDIUM

(75) Inventor: Hiroshi Yamaguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 790 days.

(21) Appl. No.: 12/294,845

(22) PCT Filed: Mar. 26, 2007

(86) PCT No.: PCT/JP2007/057332
§ 371 (c)(1),
(2), (4) Date: Jan. 15, 2009

(87) PCT Pub. No.: WO2007/116849
PCT Pub. Date: Oct. 18, 2007

(65) Prior Publication Data
US 2010/0165092 A1  Jul. 1, 2010

(30) Foreign Application Priority Data

Mar. 27, 2006 (JP) .................. 2006-086703
Feb. 22, 2007 (JP) .................. 2007-042174

(51) Int. Cl.
*H04N 7/18* (2006.01)
*A61B 1/04* (2006.01)
(52) U.S. Cl. .............. 348/78; 348/61; 348/77
(58) Field of Classification Search .............. 348/61–78
See application file for complete search history.

(56) References Cited

U.S. PATENT DOCUMENTS

| 5,341,181 A | 8/1994 | Godard |
| 5,818,954 A | 10/1998 | Tomono et al. |
| 7,054,473 B1* | 5/2006 | Roehrig et al. ............ 382/128 |
| 2003/0086061 A1* | 5/2003 | Pfleger ...................... 351/209 |
| 2006/0028697 A1* | 2/2006 | Sato ........................... 358/486 |
| 2009/0201364 A1* | 8/2009 | Konomura .................. 348/65 |

FOREIGN PATENT DOCUMENTS

| JP | 05-091394 A | 4/1993 |
| JP | 06-189906 A | 7/1994 |
| JP | 07-200632 A | 8/1995 |
| JP | 2000-201289 A | 7/2000 |

(Continued)

OTHER PUBLICATIONS

Communication, dated Nov. 24, 2011, issued in corresponding EP Application No. 07740768.2, 6 pages.

(Continued)

*Primary Examiner* — Joshua Joo
(74) *Attorney, Agent, or Firm* — Sughrue Mion, PLLC

(57) ABSTRACT

There is provided an image output apparatus including an image-capturing section that captures an image of the observed person, an observer's point of sight measuring section that measures a point of sight of the observer when the image-capturing section captures the image of the observed person, an output section that outputs the image of the observed person which is captured by the image-capturing section, and a point of sight output control section that causes the output section to output information indicating the point of sight of the observer which is measured by the observer's point of sight measuring section, together with the image of the observed person which is captured by the image-capturing section.

15 Claims, 26 Drawing Sheets

FOREIGN PATENT DOCUMENTS

| | | |
|---|---|---|
| JP | 2004-064409 A | 2/2004 |
| JP | 2004-267273 A | 9/2004 |
| WO | WO 99/05988 A2 | 2/1999 |
| WO | WO 01/74236 A1 | 10/2001 |
| WO | WO 02/054132 A2 | 7/2002 |

OTHER PUBLICATIONS

Notice of Reasons for Refusal, dated Mar. 21, 2012, issued in corresponding JP Application No. 2007-042174, 5 pages in English and Japanese.

* cited by examiner

×:POINT OF SIGHT OF OBSERVER
○:POINT OF SIGHT OF VIEWER

| TIME | COORDINATE OF POINT OF SIGHT | MOVEMENT RATE | SPEECH | REGION |
|---|---|---|---|---|
| $T_0$ | $P_0$ | — | NO | D |
| $T_1$ | $P_1$ | $V_0$ | NO | D |
| $T_2$ | $P_2$ | $V_1$ | YES | A |
| ⋮ | ⋮ | ⋮ | ⋮ | ⋮ |

*FIG. 14*

| | OBSERVER 910 | | OBSERVER 911 | | ... |
|---|---|---|---|---|---|
| | AVERAGE RATE | REGION | AVERAGE RATE | REGION | ... |
| WITH SPEECH | $V_0$ (LOW) | A (80%) | $V_2$ (HIGH) | C (90%) | ... |
| WITHOUT SPEECH | $V_1$ (HIGH) | D (70%) | $V_3$ (STARING) | F (50%) | ... |

*FIG. 15*

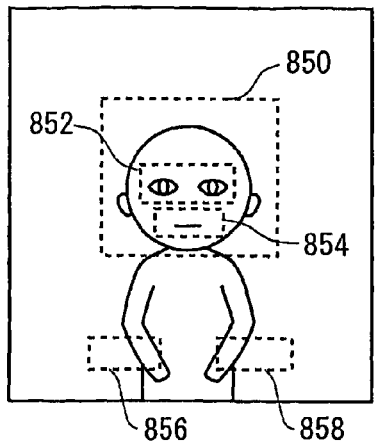
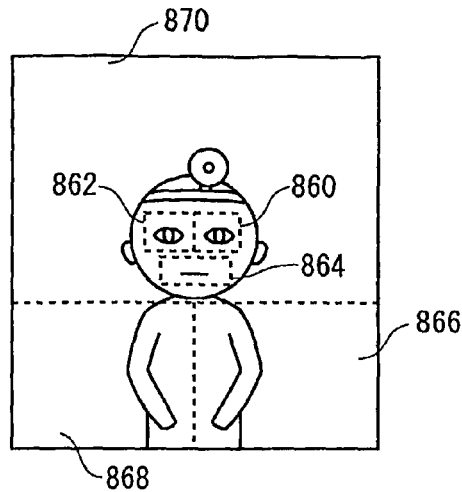
FIG. 18A      FIG. 18B
| COORDINATE DATA | REGION |
|---|---|
| $x_0 \leq x \leq x_1$<br>$y_0 \leq y \leq y_1$<br>$z_0 \leq z \leq z_1$ | 850<br>(FACE) |
| ⋮ | 852<br>(EYES) |
| ⋮ | 854<br>(MOUTH) |
| ⋮ | ⋮ |
| COORDINATE DATA | REGION |
|---|---|
| $X_0 \leq X < X_1$<br>$Y_0 \leq Y < Y_1$<br>$Z_0 \leq Z < Z_1$ | 860<br>(LEFT EYE) |
| ⋮ | 862<br>(LEFT EYE) |
| ⋮ | 864<br>(MOUTH) |
| ⋮ | ⋮ |
FIG. 19

| FILE NAME | TIME | POINT OF SIGHT OF OBSERVER | REGION | POINT OF SIGHT OF OBSERVED PERSON | REGION | FILE NAME | CONTENTS |
|---|---|---|---|---|---|---|---|
| MOVING IMAGE 1 | $t_0$ | $x'_0, y'_0, z'_0$ | RIGHT EYE | $X'_0, Y'_0, Z'_0$ | FACE OF DOCTER | SOUND DATA 1 | SPEECH 1 |
|  | $t_1$ | $x'_1, y'_1, z'_1$ | MOUTH | $X'_1, Y'_1, Z'_1$ | MOUTH OF DOCTER |  | SPEECH 2 |
|  | $t_2$ | $x'_2, y'_2, z'_2$ | MOUTH | $X'_2, Y'_2, Z'_2$ | ONE'S OWN HANDS |  |  |
|  | ... | ... | ... | ... | ... |  |  |
| MOVING IMAGE 2 |  |  | ... | ... | ... | SOUND DATA 2 | ... |
|  |  |  |  |  |  |  |  |
|  |  |  | ... | ... | ... |  |  |
| ... | ... | ... | ... | ... | ... | ... | ... |

| TIME | OBSERVATION RESULT | IMAGE | SOUND INFORMATION |
|---|---|---|---|
| MARCH 1, 2006 15:00 | ○○○○ | MOVING IMAGE A (14:57~15:00) | SOUND DATA A |
| MAY 2, 2006 9:00 | ×××× | MOVING IMAGE B (8:57~9:00) | SOUND DATA B |
| ・・・・・・ | ・・・・・ | ・・・・・ | ・・・・・・ |

| DISEASE NAME | MOVEMENT OF EYES ||||
| | LINE OF SIGHT DATA | PUPIL DATA | BLINK DATA | ... |
| DISEASE780 | 10 | 1 | 4 | ... |
| DISEASE782 | 8 | 10 | 2 | ... |
| DISEASE784 | 1 | 3 | 9 | ... |
| ... | ... | ... | ... | ... |

IMAGE OUTPUT APPARATUS, IMAGE OUTPUT METHOD AND IMAGE OUTPUT COMPUTER READABLE MEDIUM

CROSS REFERENCE TO RELATED APPLICATION

The present application claims priority from Japanese Patent Applications No. 2006-086703 filed on Mar. 27, 2006 and No. 2007-042174 filed on Feb. 22, 2007, the contents of which are incorporated herein by reference.

BACKGROUND

1. Technical Field

The present invention relates to an image output apparatus, an image output method and an image output computer readable medium. More particularly, the present invention relates to an image output apparatus, an image output method and an image output computer readable medium for assisting an observer who observes an observed person.

2. Related Art

A medical system has been proposed which records a medical image in association with observed status information obtained when a medical doctor interprets the medical image (see Patent Document 1, for example). According to the invention disclosed by Patent Document 1, the observed status information recorded includes information regarding a device used for displaying the medical image, the operation history of the displaying device, and point of sight information of the medical doctor. The operation history is used to reproduce how long the medical doctor observes the image. The point of sight information includes information that associates information regarding the line of sight of the medical doctor with a position on the display screen, a time period for which the medical doctor maintains observation with a particular point of sight, and the movement rate of the medical doctor's eyeball. The point of sight information is used to reproduce the position on the medical image the medical doctor pays attention to.

[Patent Document 1] Unexamined Japanese Patent Application Publication No. 2004-267273

In the course of diagnosing a patient who is an observed person, what plays an important role in knowing the symptoms of the observed person is the movement of the observed person noticed by a medical doctor, who is an observer, while the medical doctor diagnoses the observed person, for example, the movement of the line of sight of the observed person. According to the invention disclosed in Patent Document 1, however, what the observer notices while interpreting the medical image is reproduced based on the observed status information. Therefore, the invention can not reproduce a moving part of the observed person which catches the observer's attention while the observer diagnoses the observed person. There is another problem for the invention disclosed in Patent Document 1. What plays an important role in knowing the symptoms of the observed person also includes a change in the facial expression of the observed person which is triggered by a question the observer asks to the observed person while observing the observed person. The invention disclosed in Patent Document 1 can not reproduce the facial expression worn by the observed person in response to the observer's question.

SUMMARY

In view of the above, an object of the present invention is to provide an image output apparatus, an image output method and an image output computer readable medium which can solve the above-mentioned problems. This object is achieved by combining the features recited in the independent claims. The dependent claims define further effective specific example of the present invention.

To solve the above-mentioned problem, a first embodiment of the present invention provides an image output apparatus for assisting an observer who observes an observed person. The image output apparatus includes an image-capturing section that captures an image of the observed person, an observer's point of sight measuring section that measures a point of sight of the observer when the image-capturing section captures the image of the observed person, an output section that outputs the image of the observed person which is captured by the image-capturing section, and a point of sight output control section that causes the output section to output information indicating the point of sight of the observer which is measured by the observer's point of sight measuring section, together with the image of the observed person which is captured by the image-capturing section. Here, the point of sight output control section may cause the output section to output a mark indicating the point of sight of the observer which is measured by the observer's point of sight measuring section, in such a state that the mark is overlapped onto the image of the observed person which is captured by the image-capturing section. The image output apparatus may further include a point of sight image extracting section that extracts a partial image including the point of sight of the observer which is measured by the observer's point of sight measuring section, from the image of the observed person which is captured by the image-capturing section. Here, the point of sight output control section may cause the output section to output an image obtained by enlarging the partial image extracted by the point of sight image extracting section, together with the image of the observed person which is captured by the image-capturing section.

The image output apparatus may further include a view measuring section that measures a view of the observer. Here, the point of sight image extracting section may extract an image corresponding to the view of the observer which is measured by the view measuring section, from the image of the observed person which is captured by the image-capturing section. The image output apparatus may further include an observed person's information storing section that stores thereon the image of the observed person which is captured by the image-capturing section in association with the observed person, and a previous image output control section that, when the image-capturing section captures a new image of the observed person, causes the output section to output a previous image of the observed person which is stored on the observed person's information storing section in association with the observed person, together with the new image of the observed person which is captured by the image-capturing section. The observed person's information storing section may further store thereon the information indicating the point of sight of the observer which is measured by the observer's point of sight measuring section in association with the observed person, and the previous image output control section may cause the output section to output the information indicating the point of sight of the observer, together with the previous image of the observed person.

The image output apparatus may further include a sound recording section that records sound information of the observer when the image-capturing section captures the image of the observed person, an image storing section that stores thereon the sound information of the observer which is recorded by the sound recording section, in association with the image of the observed person which is captured by the image-capturing section, a sound information comparing section that compares sound information of the observer which is newly recorded by the sound recording section with the sound information of the observer which is previously recorded by the sound recording section and stored on the image storing section, and a previous image extracting section that extracts, based on a result of the comparison done by the sound information comparing section, a previous image of the observed person which is stored on the image storing section in association with previous sound information of the observer which shows a higher coincidence level than a predetermined level with the sound information of the observer which is newly recorded by the sound recording section. Here, the previous image output control section may cause the output section to output the previous image of the observed person which is extracted by the previous image extracting section, together with the new image of the observed person which is captured by the image-capturing section.

The output section may be a display section. The image output apparatus may further include an observed person's information storing section that stores the image of the observed person which is captured by the image-capturing section in association with the point of sight of the observer which is measured by the observer's point of sight measuring section, a previous image output control section that reads the image of the observed person which is stored on the observed person's information storing section, and causes the display section to display the read image of the observed person, and a viewer's point of sight measuring section that measures a point of sight of a viewer who views the image of the observed person which is displayed on the display section. Here, the observed person's information storing section may further store thereon information indicating the point of sight of the viewer which is measured by the viewer's point of sight measuring section, in association with the image of the observed person which is read by the previous image output control section.

The image output apparatus may further include a viewer's point of sight judging section that judges whether the point of sight of the observer which is measured by the observer's point of sight measuring section coincides with the point of sight of the viewer which is measured by the viewer's point of sight measuring section, and a viewed image extracting section that, when the viewer's point of sight judging section judges negatively, extracts an image corresponding to information indicating that the points of sight do not coincide with each other. Here, the previous image output control section may cause the output section to output the image which corresponds to the information indicating that the points of sight do not coincide with each other and is thus extracted by the viewed image extracting section.

The viewer's point of sight judging section may judge that the point of sight of the observer which is measured by the observer's point of sight measuring section does not coincide with the point of sight of the viewer which is measured by the viewer's point of sight measuring section, when the point of sight of the viewer is not present within a predetermined region including the point of sight of the observer. When the point of sight of the observer which is measured by the observer's point of sight measuring section moves to a plurality of different positions, the viewer's point of sight judging section may judge that the point of sight of the observer coincides with the point of sight of the viewer which is measured by the viewer's point of sight measuring section if the point of sight of the viewer moves to vicinities which respectively correspond to the plurality of different positions. The viewer's point of sight judging section may judge that the point of sight of the observer coincides with the point of sight of the viewer if the point of sight of the viewer which is measured by the viewer's point of sight measuring section moves to the vicinities in a same order as the point of sight of the observer.

The viewer's point of sight judging section may judge that the point of sight of the observer coincides with the point of sight of the viewer if the point of sight of the observer which is measured by the observer's point of sight measuring section and the point of sight of the viewer which is measured by the viewer's point of sight measuring section are both present in a predetermined region of the image of the observed person which is captured by the image-capturing section. The predetermined region of the image may include at least one of an eye, a mouth and a hand of the observed person.

The point of sight output control section may cause the output section to output at least one of (i) a mark indicating a position of the point of sight of the observer which is measured by the observer's point of sight measuring section and (ii) a mark indicating a position of the point of sight of the viewer which is measured by the viewer's point of sight measuring section, in such a state that the at least one of the marks is overlapped onto the image of the observed person.

A second embodiment of the present invention provides an image output method for assisting an observer who observes an observed person. The image output method includes capturing an image of the observed person, measuring a point of sight of the observer during the image capturing, and outputting information indicating the point of sight of the observer which is measured in the point of sight measuring, together with the image of the observed person which is captured in the image capturing.

A third embodiment of the present invention provides an image output computer readable medium for an image output apparatus that assists an observer who observes an observed person. The image output computer readable medium causes the image output apparatus to function as an image-capturing section that captures an image of the observed person, an observer's point of sight measuring section that measures a point of sight of the observer when the image-capturing section captures the image of the observed person, an output section that outputs the image of the observed person which is captured by the image-capturing section, and a point of sight output control section that causes the output section to output information indicating the point of sight of the observer which is measured by the observer's point of sight measuring section, together with the image of the observed person which is captured by the image-capturing section.

Here, all the necessary features of the present invention are not listed in the summary. The sub-combinations of the features may become the invention.

According to the present invention, an image can be extracted which shows an area of an observed person to which an observer pays attention while observing the observed person, and displayed with the position of the observer's line of sight being overlapped thereon. Consequently, the present invention makes it possible to accurately know how the observer observes the observed person.

BRIEF DESCRIPTION OF THE DRAWINGS

FIG. 14 is used to illustrate the operation performed by the point of sight moving method learning section 216.

FIG. 15 is used to illustrate the operation performed by the point of sight moving method learning section 216.

FIGS. 18A and 18B are used to illustrate the operation performed by an observer's point of sight judging section 250.

FIG. 19 is used to illustrate the operation performed by the observer's point of sight judging section 250.

FIG. 20 illustrates one example of data stored on an image storing section 320.

FIG. 23 illustrates exemplary data stored on the image storing section 320.

FIG. 30 illustrates an exemplary structure of data stored on a physical status data storing section 720.

DESCRIPTION OF EXEMPLARY
EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
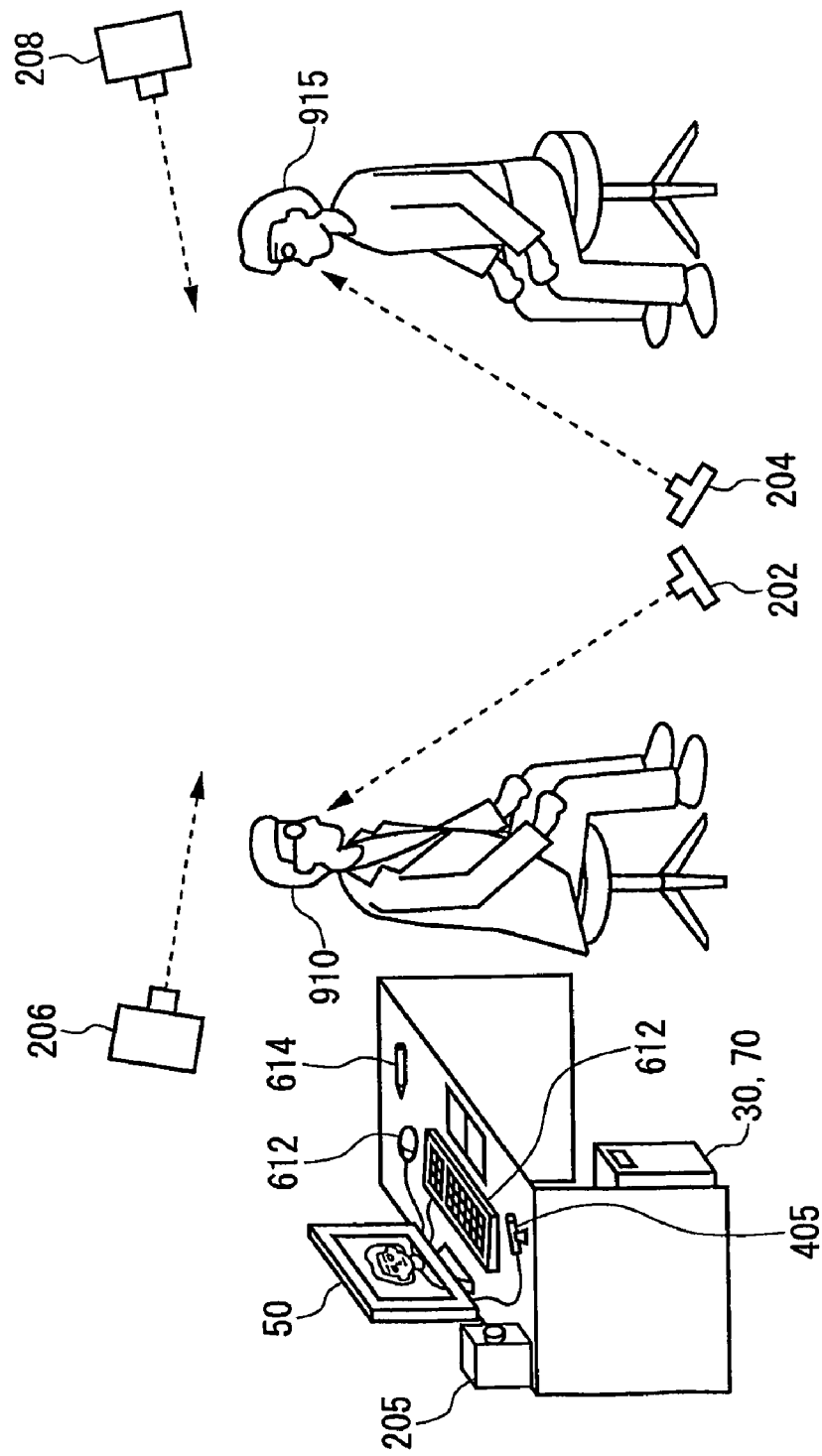
FIG. 1 is a schematic view illustrating an image recording apparatus 10.
Figure 2:
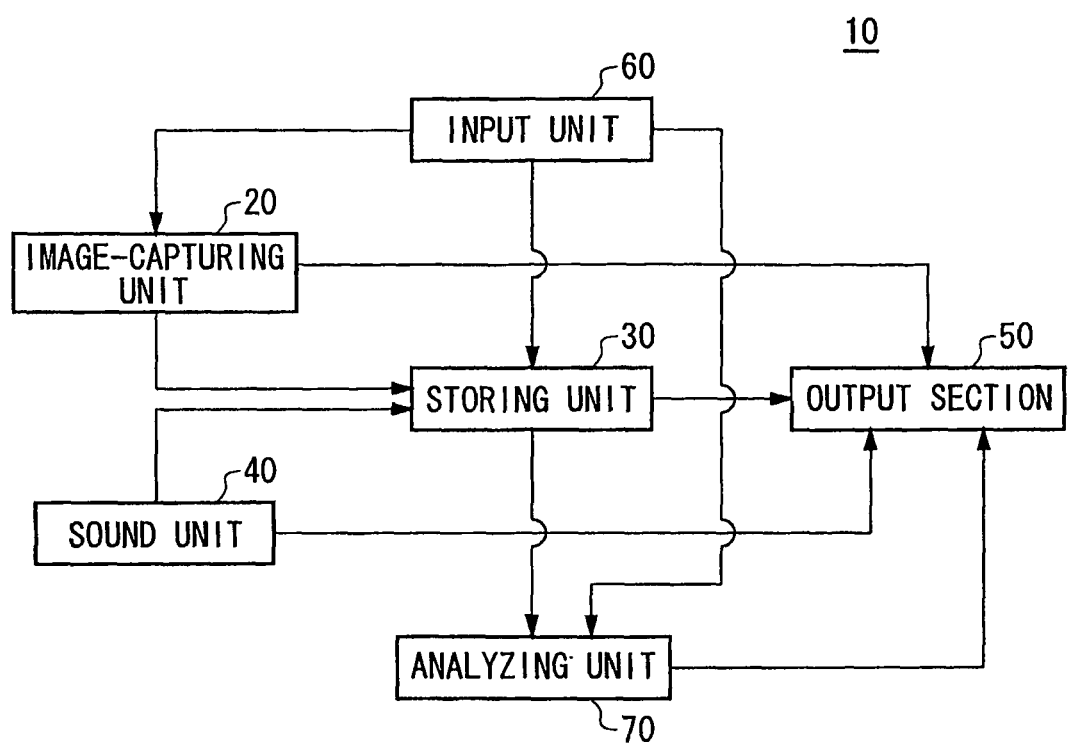
FIG. 2 is a block diagram illustrating the functional configuration of the image recording apparatus 10.

FIGS. 1 and 2 schematically illustrate an image recording apparatus 10 relating to a first embodiment of the present invention. The image recording apparatus 10 includes therein an image-capturing unit 20, a storing unit 30, a sound unit 40, an output section 50, an input unit 60, and an analyzing unit 70. The image-capturing unit 20 relating to the first embodiment includes therein a plurality of image-capturing sections. For example, the image-capturing unit 20 includes an image-capturing section 202 for detecting the point of sight of an observer 910, an image-capturing section 208 for measuring the area within which the observer 910 is present, an image-capturing section 204 for detecting the point of sight of an observed person 915, and an image-capturing section 206 for measuring the area within which the observed person 915 is present. The image-capturing sections 202 to 208 may be each a three-dimensional camera, or a camera for capturing two-dimensional images. The output section 50 is a display, for example. The input unit 60 includes therein a digital input section 612 and a writing section 614. The digital input section 612 may include a keyboard and a mouse, and the writing section 614 may be a pen, for example. The sound unit 40 may include therein a sound collecting section 405. Note that the image recording apparatus 10 relating to the present embodiment is an example of an image output apparatus. The image recording apparatus 10 relating to the first embodiment aims to detect an area of the observed person 915 to which the observer 910 pays attention while the observer 910 is observing the observed person 915 and to display an image showing the area of the observed person 915 to which the observer 910 pays attention with the point of sight of the observer 910 being overlapped onto the image. In addition, the first embodiment aims to provide an image output apparatus which detects the point of sight of a viewer who views a recorded image of the observed person 915 on the output section 50 so as to enable the viewer to look at the point of sight of the observer 910.

The image-capturing unit 20 measures the points of sight of the observer 910 and the observed person 915 by means of the corneal reflex method or by detecting a change in light intensity distribution of an image of the eyeball area. Also, the image-capturing unit 20 uses the image of the observed person 915 captured by the image-capturing section 206 and the image captured by the image-capturing section 202 for detecting the point of sight of the observer 910, in order to identify the area of the observed person 915 which is observed by the observer 910.

Also, the image recording apparatus 10 uses the image captured by the image-capturing section 208 for identifying the area, within the image-capturing target area, in which the observer 910 is present and an image captured by the image-capturing section 204 for measuring the direction of the line of sight of the observed person 915, in order to identify an area of the observer 910 or an area of a space other than the observer 910 which the observed person 915 looks at. Here, the image-capturing sections 202 to 208 of the image-capturing unit 20 may include an omnidirectional camera. When any one of the image-capturing sections 202 to 208 is an omnidirectional camera, the single omnidirectional camera can capture the images for measuring the directions of the lines of sight of the observer 910 and observed person 915 and the images for measuring the positions, within the image-capturing target area, where the observer 910 and observed person 915 are respectively present. Therefore, the image recording apparatus 10 is not required to include therein a plurality of image-capturing sections such as the image-capturing section 202 as mentioned above.

When the observer 910 moves the line of sight to the area within which the observed person 915 is present, the image recording apparatus 10 captures an image showing a predetermined area of the observed person 915 which includes the point of sight of the observer 910. The image recording apparatus 10 then displays, on the output section 50, the captured image showing the observed person 915, with a mark indicating the point of sight of the observer 910. In this case, the image recording apparatus 10 may display, side by side, an image showing the observed person 915 and an enlarged image obtained by enlarging at a predetermined enlarging ratio the captured partial image of the observed person 915. According to the image recording apparatus 10, the image-capturing section 206 captures the image of the observed person 915 when the observer 910 writes the symptoms of the observed person 915 into an electronic medical record by way of the digital input section 612 such as a keyboard and a mouse, or when the observer 910 writes the symptoms into a medical record using the writing section 614 such as a pen. In addition, the image recording apparatus 10 obtains, through the sound collecting section 405, the sound uttered by the observer 910 to ask a question to the observed person 915. In this way, the image recording apparatus 10 displays, side by side on the output section 50, an image of the observed person 915 which is captured when the observer 910 previously asks the same question to the observed person 915 and the current image of the observed person 915.

In the image recording apparatus 10, the analyzing unit 70 analyzes the images captured by the image-capturing sections 204 and 206 to determine the physical status of the observed person 915. For example, based on the image of the observed person 915 captured by the image-capturing section 204, the analyzing unit 70 obtains information about the observed person 915 such as a change in the size of the pupils, the movement of the line of sight, the moving rate of the line of sight, and the number of blinks, so as to identify the disease of the observed person 915. When the image-capturing section 204 or 206 includes therein a temperature measuring section for measuring the temperature of the face of the observed person 915, the analyzing unit 70 may also use the measured temperature of the face of the observed person 915 to identify the disease of the observed person 915. The analyzing unit 70 displays the identified disease on the display screen. Specifically speaking, the analyzing unit 70 displays, on the display screen, information including the name and symptoms of the disease. The analyzing unit 70 may display on the display screen multiple disease candidates which the observed person 915 may possibly suffer from.

According to the image recording apparatus 10 of the first embodiment, the point of sight of the observer 910 can be overlapped onto the image of the observed person 915 when displayed. In this way, the image recording apparatus 10 makes it possible to easily know the area of the observed person 915 on which the observer 910 focuses while observing the observed person 915. For example, a moving image of the observed person 915 can be captured and displayed on the output section 50 with the movement of the point of sight of the observer 910 being overlapped onto the moving image. Therefore, the image recording apparatus 10 can reproduce how the observer 910 observes and diagnoses the observed person 915. Also, the image recording apparatus 10 can capture an image showing how the observed person 915 behaves while the observer 910 writes the result of the observation into the electronic medical record. In this way, even if the observer 910 misses a change in the facial expressions of the observed person 915, the image recording apparatus 10 makes it possible to easily retrieve and reproduce, after the observation, an image showing the missed facial expressions of the observed person 915. In addition, the image recording apparatus 10 can display side by side the previous and current images of the observed person 915, and therefore makes it possible to accurately know a change in the symptoms of the observed person 915.

Figure 3:
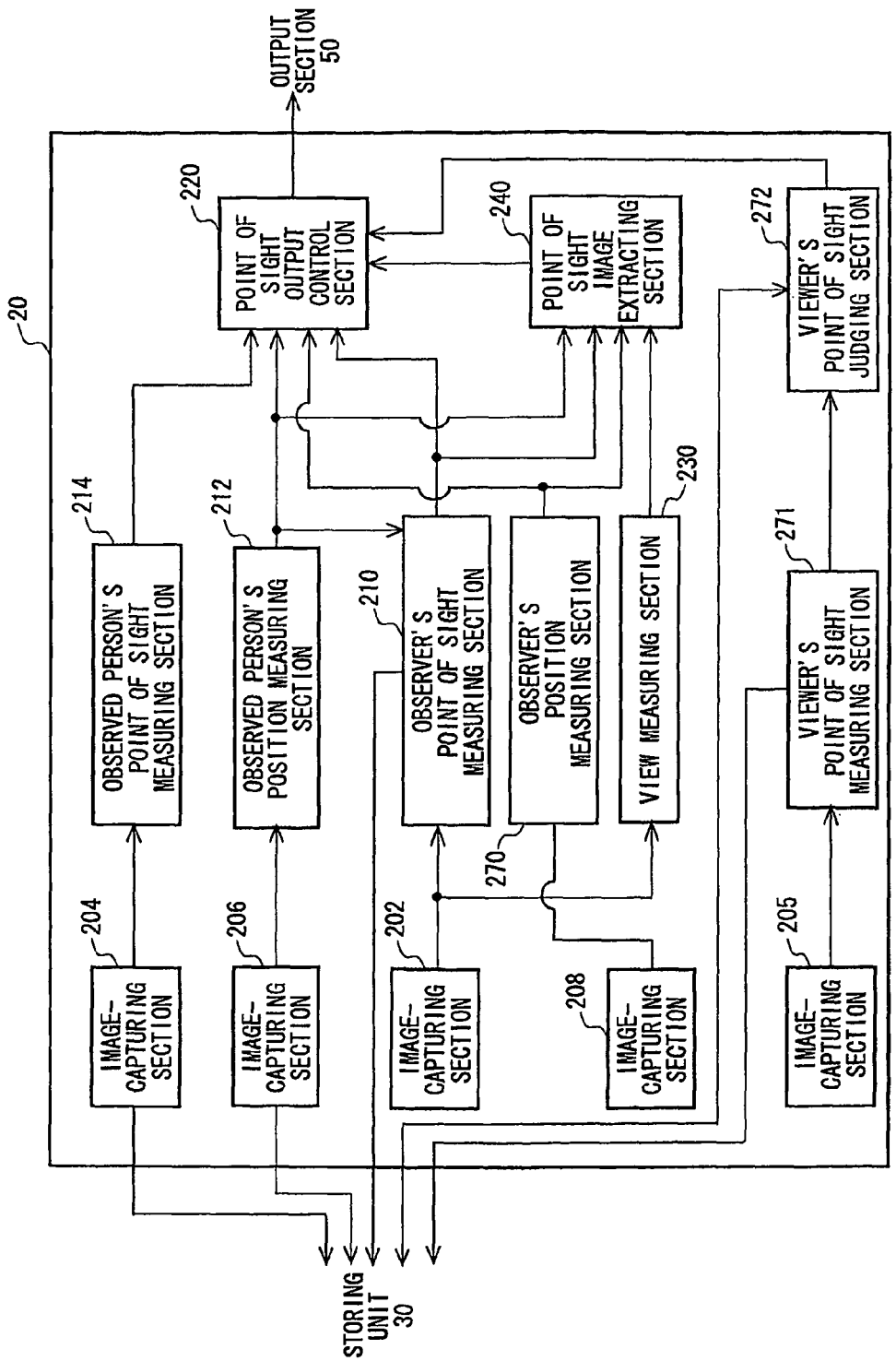
FIG. 3 is a block diagram illustrating the functional configuration of an image-capturing unit 20.
Figure 4:
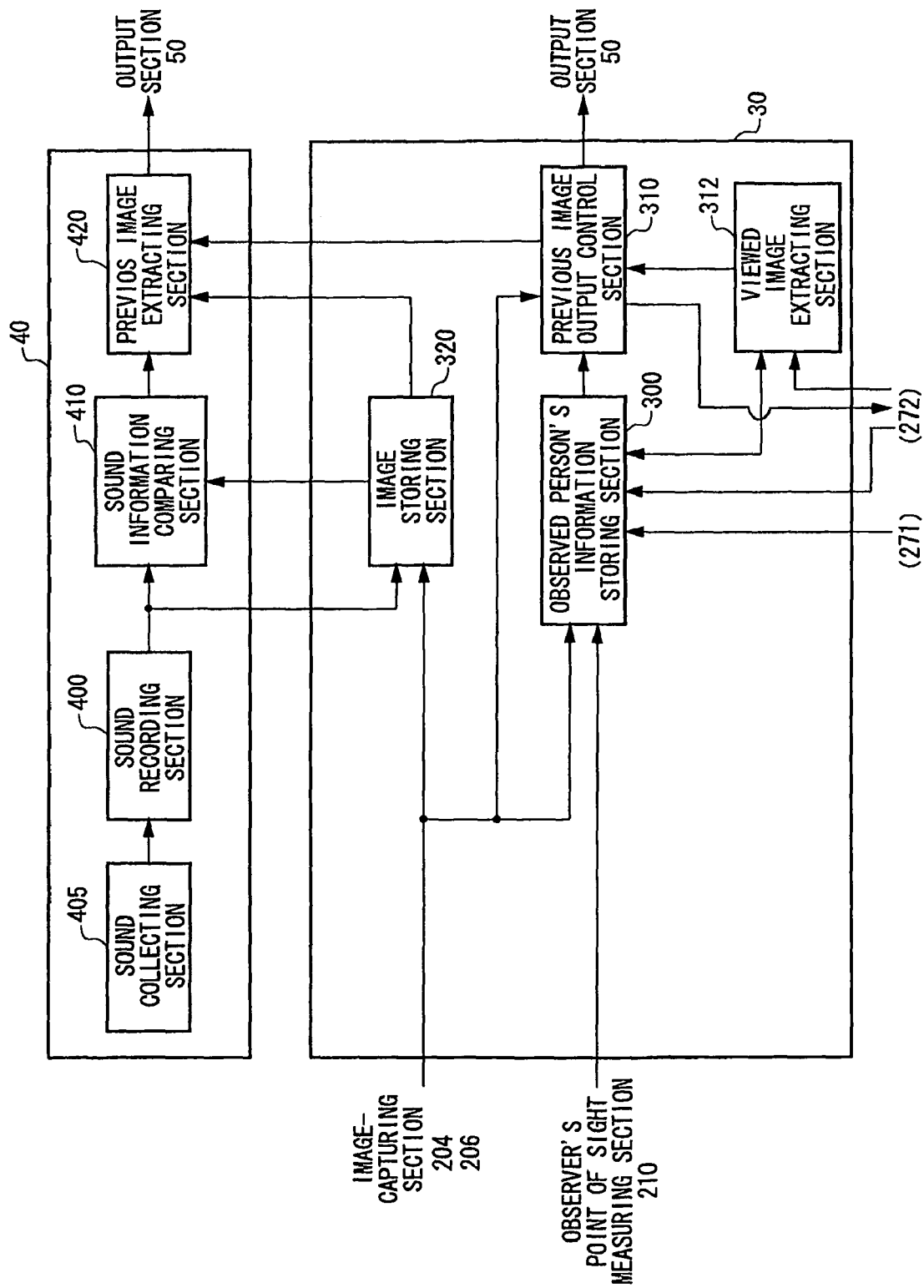
FIG. 4 is a block diagram illustrating the functional configurations of a storing unit 30 and a sound unit 40.

FIG. 3 illustrates an exemplary functional configuration of the first embodiment of the image-capturing unit 20. The image-capturing unit 20 includes therein the image-capturing sections 202, 204, 206 and 208, an observer's point of sight measuring section 210, an observed person's position measuring section 212, an observed person's point of sight measuring section 214, a point of sight output control section 220, a view measuring section 230, a point of sight image extracting section 240, and an observer's position measuring section 270. FIG. 4 illustrates exemplary functional configurations of the storing unit 30 and sound unit 40. The storing unit 30 includes therein an observed person's information storing section 300, a previous image output control section 310, and an image storing section 320. The sound unit 40 includes therein a sound recording section 400, a sound information comparing section 410, and a previous image extracting section 420.

The image-capturing section 204 captures an image of the observed person 915. The image-capturing section 204 may capture a moving image of the observed person 915. The image-capturing section 204 supplies the captured image of the observed person 915 to the observed person's point of sight measuring section 214 and the image storing section 320 of the storing unit 30. The image-capturing section 206 captures an image for identifying a position at which the observed person 915 is present within the predetermined image-capturing target area. The image-capturing section 206 supplies the captured image to the observed person's position measuring section 212. The image-capturing section 202 captures an image of the observer 910. The image-capturing section 202 supplies the captured image to the observer's point of sight measuring section 210 and the view measuring section 230. The image-capturing section 208 captures an image for identifying the position at which the observer 910 is present within the predetermined image-capturing target area. The image-capturing section 208 supplies the captured image to the observer's position measuring section 270. Here, the image-capturing sections 202, 204, 206 and 208 may each capture a moving image of a corresponding one of the observer 910 and observed person 915.

When capturing moving images, the image-capturing sections 202, 204, 206 and 208 each may supply to one or more corresponding constituents a plurality of images composing the corresponding moving image. Here, the images composing the moving image may include any type of frame images, field images, and other moving-image composing images in a different format. Here, the image recording apparatus 10 may additionally include therein a blink measuring section for measuring the number of blinks of the observed person 915. Such a blink measuring section measures the number of times the observed person 915 blinks within a predetermined period of time. The blink measuring section supplies the measured number of blinks of the observed person 915 to the observed person's information storing section 300.

The observer's point of sight measuring section 210 measures the point of sight of the observer 910 when the image-capturing sections 204 and 206 capture the images of the observed person 915. Specifically speaking, the observer's point of sight measuring section 210 may include therein a first observer's line of sight measuring section for measuring the line of sight of the left eye of the observer 910 and a second observer's line of sight measuring section for measuring the line of sight of the right eye of the observer 910. The first and second observer's line of sight measuring sections use the image captured by the image-capturing section 202 to measure the directions of the lines of sight of the left and right eyes of the observer 910. Here, the observer's point of sight measuring section 210 may measure the directions of the lines of sight of the observer 910 based on the corneal reflex method. Alternatively, the first and second observer's line of sight measuring sections extract the images showing the eyeballs from the images of the left and right eyes of the observer 910, and detect changes in the light intensity distributions in the extracted images showing the eyeballs. The first and second observer's line of sight measuring sections may calculate the directions of the lines of sight of the left and right eyes of the observer 910 based on the detected light intensity distributions. For example, the first observer's line of sight measuring section calculates the light intensity distribution of the image showing the eyeball, which varies in response to the position of the iris or pupil, in terms of the vertical and horizontal directions of the eyeball of the left eye.

To be specific, the directions of the lines of sight of the observer 910 are each identified by comparing the light intensity distribution of the eyeball image which is observed when the line of sight of the observer 910 extends in the front direction of the observer 910 and the light intensity distribution of the eyeball image which is observed when the line of sight of the observer 910 extends in a direction other than the front direction. For example, the direction in which the iris or pupil of the left eye faces, that is to say, the direction of the line of sight of the left eye can be calculated by comparing the light intensity distribution of the eyeball image of the left eye which is calculated by the first observer's line of sight measuring section, with the light intensity distribution of the left eyeball image which is observed when the line of sight of the left eye of the observer 910 extends in the front direction of the observer 910. It should be noted that the first observer's line of sight measuring section may judge that the line of sight of the left eye extends in the front direction of the observer 910 when detecting that the light intensity distribution of the eyeball image which is calculated in terms of the vertical and horizontal directions of the eyeball of the left eye is substantially even with respect to the central point of the left eye. In the same manner, the second observer's line of sight measuring section calculates the direction of the line of sight of the right eye. Here, the first and second observer's line of sight measuring sections may identify the directions of the lines of sight of the left and right eyes of the observer 910 based on the combination of the corneal reflex method and the detection of the changes in the light intensity distributions of the eyeball images. The observer's point of sight measuring section 210 identifies the point of sight of the observer 910 based on the lines of sight of the left and right eyes. For example, the observer's point of sight measuring section 210 may identify, as the point of sight of the observer 910, a point at which the lines of sight of the left and right eyes intersect each other or a point in the vicinity of the intersecting point. When the lines of sight of the left and right eyes do not intersect each other, the observer's point of sight measuring section 210 may identify, as the point of sight of the observer 910, the midpoint of a perpendicular line which extends from one of the lines of sight to the other or a point in the vicinity of the midpoint. Alternatively, the point of sight of the observer 910 can be calculated based on the lines of sight calculated by the observer's point of sight measuring section 210 and three-dimensional coordinate data which indicates the area within which the observer 910 is present and calculated by the observer's position measuring section 270, as described later. The observer's point of sight measuring section 210 supplies information indicating the identified point of sight of the observer 910 to the point of sight output control section 220 and point of sight image extracting section 240. Here, the observed person's point of sight measuring section 214 measures the point of sight of the observed person 915 in the same manner as the observer's point of sight measuring section 210. The observed person's point of sight measuring section 214 supplies information indicating the point of sight of the observed person 915 to the point of sight output control section 220 and point of sight image extracting section 240.

The observed person's position measuring section 212 measures the position, within the predetermined image-capturing target area, at which the observed person 915 is present based on the image of the observed person 915 captured by the image-capturing section 206. Specifically speaking, the observed person's position measuring section 212 obtains coordinate data in which the position at which the observed person 915 is present is determined in accordance with a predetermined three-dimensional coordinate system. For example, the positions and image-capturing directions of the image-capturing sections 202, 204, 206 and 208 and the positions at which the observer 910 and observed person 915 are present are determined in advance in accordance with the predetermined three-dimensional coordinate system. To be specific, an area occupied by the observed person 915 within the image-capturing target area of the image-capturing section 206 can be identified by causing the observed person 915 to be present at a predetermined position. For example, the area occupied by the observed person 915 within the image-capturing target area of the image-capturing section 206 can be identified by using coordinate data by causing the observed person 915 to be seated at a predetermined position. In the same manner, the area occupied by the observer 910 within the image-capturing target area of the image-capturing section 208 can be identified by using coordinate data by causing the observer 910 to be seated at a predetermined position. When the observed person 915 moves within the image-capturing target area of the image-capturing section 206, the observed person's position measuring section 212 may measure the area occupied by the observed person 915 within the image-capturing target area of the image-capturing section 206 in compliance with the movement of the observed person 915.

The image-capturing section 206 may be a three-dimensional camera. The observed person's position measuring section 212 calculates the position at which the observed person 915 is present in a three-dimensional coordinate system, based on the image captured by the image-capturing section 206. For example, the image-capturing section 206 detects, for each pixel, a distance from the image-capturing section 206 to the area within the image-capturing target area in which the observed person 915 is present. Based on the distance to the observed person 915 which is detected by the image-capturing section 206, the observed person's position measuring section 212 may calculate coordinate data indicating the position at which the observed person 915 is present within the three-dimensional coordinate system. The observed person's position measuring section 212 supplies the calculation result to the point of sight output control section 220 and point of sight image extracting section 240. Also, the observed person's position measuring section 212 may supply the calculation result to the observer's point of sight measuring section 210. The observer's position measuring section 270 measures the position, within the image-capturing target area of the image-capturing section 208, at which the observer 910 is present. The observer's position measuring section 270 may calculate coordinate data indicating the position within a three-dimensional coordinate system at which the observer 910 is present, in the same manner as the observed person's position measuring section 212. The observer's position measuring section 270 supplies the result of the calculation to the point of sight output control section 220 and point of sight image extracting section 240. Since the image-capturing direction of the image-capturing section 202 is determined in advance in accordance with the three-dimensional coordinate system, the observer's point of sight measuring section 210 can calculate coordinate data indicating the direction of the line of sight of the observer 910 based on the image captured by the image-capturing section 202. In the same manner, the observed person's point of sight measuring section 214 can calculate coordinate data indicating the direction of the line of sight of the observed person 915 based on the image captured by the image-capturing section 204.

Here, the observer's point of sight measuring section 210 identifies which area of the observed person 915 has the point of sight of the observer 910, based on the coordinate data which is calculated by the observed person's position measuring section 212 and indicates the area in which the observed person 915 is present and the direction of the line of sight of the observer 910 which is measured by the observer's point of sight measuring section 210. Specifically speaking, the observer's point of sight measuring section 210 may determine, as the point of sight of the observer 910, an intersection of the area of the observed person 915 which is identified by the coordinate data which is calculated by the observed person's position measuring section 212 and indicates the area in which the observed person 915 is present and a line extending from the eyes of the observer 910 along the direction of the line of sight of the observer 910 which is measured by the observer's point of sight measuring section 210. The observer's point of sight measuring section 210 obtains the coordinate data of the intersection as the coordinate data indicating the point of sight of the observer 910. The observed person's point of sight measuring section 214 may obtain the coordinate data indicating the point of sight of the observed person 915 in the same manner as the observer's point of sight measuring section 210.

Also, the observer's point of sight measuring section 210 extracts information about the observer 910 such as the outline of the face, the shapes of the eyes, and the characteristic points of the eyes (the inner and outer corners of the eyes). When the observer 910 moves the head, the observer's point of sight measuring section 210 may trace the extracted characteristic points of the eyes and the like so as to follow the movement of the observer 910, and measure the line of sight of the observer 910. For example, the observer's point of sight measuring section 210 may include therein an observer's characteristic point extracting section for extracting the characteristic points of the eyes of the observer 910 and the like and a movement control section for moving the image-capturing section 202 in accordance with the movement of the characteristic points of the eyes and the like of the observer 910 which are extracted by the observer's characteristic point extracting section. With this configuration, even when the observer 910 moves the head, the observer's point of sight measuring section 210 can appropriately measure the point of sight of the observer 910 by moving the image-capturing section 202 in accordance with the movement of the head of the observer 910. The observer's point of sight measuring section 210 supplies the measured point of sight of the observer 910 to the point of sight output control section 220 and point of sight image extracting section 240.

Here, the observer 910 may remotely observe the observed person 915. For example, an image recording apparatus 10 is provided for the observer 910 and another image recording apparatus 10 is provided for the observed person 915, and the image recording apparatuses 10 are connected to each other by a network such as the Internet. If this is the case, the image-capturing sections 204 and 206 for capturing the images of the observed person 915 supply, via the network, the captured images of the observed person 915 to the output section 50 of the image recording apparatus 10 for the observer 910. Thus, the observer 910 observes the images of the observed person 915 displayed on the output section 50. In this case, the observer's point of sight measuring section 210 measures which area of the observed person 915 displayed on the output section 50 is focused by the observer 910.

The view measuring section 230 identifies the view of the observer 910. To be specific, the view measuring section 230 analyzes the image captured by the image-capturing section 202, so as to identify an angle of convergence based on the directions of the lines of sight of the left and right eyes of the observer 910. For example, the view measuring section 230 may calculate the angle of convergence formed by the directions of the lines of sight of the left and right eyes of the observer 910 based on the image of the observer 910 captured by the image-capturing section 202. Here, the view measuring section 230 may receive the information indicating the directions of the lines of sight of the observer 910 which are measured by the observer's point of sight measuring section 210, and calculate the angle of convergence based on the received information indicating the directions of the lines of sight. Alternatively, the view measuring section 230 may measure the focal distance of the left and right eyes of the observer 910, and identify, as the view of the observer 910, the area within which the eyes of the observer 910 focus together. As another example, the view measuring section 230 measures a still time period during which the line of sight of the observer 910 stays still. Specifically speaking, the view measuring section 230 may measure the still time period of the line of sight of the observer 910, and identify, as the view of the observer 910, an area for which the measured still time period is longer than a predetermined time period. Here, the predetermined time period may be one second, for example. The view measuring section 230 supplies the identified view of the observer 910 to the point of sight image extracting section 240.

The point of sight image extracting section 240 extracts a partial image, from the image of the observer person 915 which is received from the image-capturing section 204, which includes the point of sight of the observer 910 which is measured by the observer's point of sight measuring section 210. Also, the point of sight image extracting section 240 may extract an image corresponding to the view of the observer 910 which is measured by the view measuring section 230, from the image of the observed person 915 which is received from the image-capturing section 204. The point of sight image extracting section 240 supplies the extracted image to the point of sight output control section 220. The point of sight output control section 220 causes the output section 50 to output the information indicating the point of sight of the observer 910 which is received from the observer's point of sight measuring section 210, together with the image of the observed person 915 which is captured by the image-capturing section 204.

Specifically speaking, the point of sight output control section 220 causes the output section 50 to output a mark indicating the point of sight of the observer 910 which is received from the observer's point of sight measuring section 210, in such a state that the mark is overlapped onto the image of the observed person 915 which is captured by the image-capturing section 204. The point of sight output control section 220 may cause the output section 50 to output an enlarged image obtained by enlarging the image extracted by the point of sight image extracting section 240 at a predetermined enlarging ratio, together with the image of the observed person 915 which is captured by the image-capturing section 204. Here, the input unit 60 may include therein an enlarging ratio input section for allowing the observer 910 to input an enlarging ratio used by the point of sight output control section 220 to enlarge the image extracted by the point of sight image extracting section 240. Since the observer 910 is allowed to input a desired enlarging ratio into the enlarging ratio input section, the point of sight output control section 220 can cause the output section 50 to output the image of the observed person 915 which has been enlarged to a desired size.

The observed person's information storing section 300 stores thereon the image of the observed person 915 which is received from the image-capturing section 204, in association with the observed person 915. Also, the observed person's information storing section 300 stores thereon the information indicating the point of sight of the observer 910 which is received from the observer's point of sight measuring section 210, in association with the observed person 915. Furthermore, the observed person's information storing section 300 may store thereon the number of blinks of the observed person 915 which is received from the blink measuring section, in association with the time at which the observed person 915 is observed. The observed person's information storing section 300 supplies the image of the observed person 915 and information indicating the number of blinks of the observed person 915 to the previous image output control section 310, under the control of the previous image output control section 310. The sound recording section 400 records sound information relating to the observer 910 when the image-capturing section 204 captures the image of the observed person 915. The sound recording section 400 records sound information obtained when the observer 910 asks a question to the observed person 915, for example. The sound recording section 400 supplies the recorded sound information to the image storing section 320 and sound information comparing section 410.

The image storing section 320 stores thereon the image of the observed person 915 which is received from the image-capturing section 204 and the sound information which is received from the sound recording section 400, in association with each other. The image storing section 320 may store thereon the image and sound information, in association with the time at which the sound recording section 400 records the sound information. The image storing section 320 supplies the sound information to the sound information comparing section 410, under the control of the sound information comparing section 410. When the image-capturing section 204 captures a new image of the observed person 915, the previous image output control section 310 causes the output section 50 to output a previous image of the observed person 915 being stored on the observed person's information storing section 300 in association with the observed person 915, together with the image of the observed person 915 which is newly captured by the image-capturing section 204 while the observer 910 observes the observed person 915.

Here, the previous image of the observed person 915 which is output by the output section 50 under the control of the previous image output control section 310 may be an image of the observed person 915 which is captured when the observer 910 observes the observed person 915 last time, for example. Alternatively, the previous image may be an image of the observed person 915 which is captured at the first visit. Also, the previous image output control section 310 may cause the output section 50 to output information indicating the point of sight of the observer 910, together with the previous image of the observed person 915. The previous image output control section 310 may cause the number of blinks of the observed person 915 to be displayed in the state of being overlapped on the image of the observed person 915. When the image-capturing section 204 captures a new image of the observed person 915, the previous image output control section 310 may cause the output section 50 to output the previous image of the observed person 915 stored on the observed person's information storing section 300 in association with the observed person 915, the image of the observed person 915 which is newly captured by the image-capturing section 204, and the difference between the previous and current numbers of blinks.

The sound information comparing section 410 compares the sound information of the observer 910 which is newly recorded by the sound recording section 400 with the sound information of the observer 910 which is previously recorded by the sound recording section 400 and stored on the image storing section 320. For example, the sound information comparing section 410 may include therein a word pronunciation information storing section for storing, in association with words that are included in sound information, information indicating frequency components observed when the words are pronounced by a human. The sound information comparing section 410 analyzes the sound information which is newly received from the sound recording section 400 in terms of frequency components at predetermined time intervals, to generate frequency component information. Subsequently, the sound information comparing section 410 compares the generated frequency component information with the information indicating the frequency components of the words which is stored on the word pronunciation information storing section. In this way, the sound information comparing section 410 calculates a coincidence level between the sound information of the observer 910 which is newly recorded by the sound recording section 400 and the previous sound information of the observer 910. The sound information comparing section 410 supplies the calculated coincidence level to the previous image extracting section 420.

When the coincidence level received from the sound information comparing section 410 is equal to or higher than a predetermined level, the previous image extracting section 420 extracts a previous image of the observed person 915 which is stored on the image storing section 320 in association with the previous sound information of the observer 910 which shows the received coincidence level. In this case, the previous image output control section 310 may cause the output section 50 to output the previous image of the observed person 915 which is extracted by the previous image extracting section 420, together with the image of the observed person 915 which is newly captured by the image-capturing section 204. The output section 50 outputs the image of the observed person 915 which is received from the image-capturing section 204. Also, the output section 50 outputs the images received from the point of sight output control section 220 and previous image extracting section 420. In addition, the output section 50 may display the number of blinks of the observed person 915 which is measured by the blink measuring section in such a state that the number of blinks is overlapped onto the image of the observed person 915. Here, the output section 50 is a monitor or the like, for example.

In the case of the second or subsequent observation for the observed person 915, the image recording apparatus 10 may ask questions to the observed person 915 in place of the observer 910, based on the results of the previous observations which are done by the observer 910 on the observed person 915. For example, the image recording apparatus 10 may include therein a question storing section for storing thereon predetermined questions in association with the behaviors of the observed person 915. The image recording apparatus 10 then may display an appropriate question selected from the questions stored on the question storing section in accordance with the symptoms of the observed person 915, on the display screen which is shown as one example of the output section 50, so as to encourage the observed person 915 to answer to the displayed question and record the answer thereon. In this way, the observer 910 is not required to do a routine health interview. As a result, the observer 910 can spend a longer time period on the observation of the observed person 915 than otherwise.

The image recording apparatus 10 relating to the present embodiment judges whether the observer 910 observes the entire body of the observed person 915 or pays attention to a particular area of the observed person 915, and obtains the point of sight of the observer 910 which is identified when the observer 910 pays attention to the particular area of the observed person 915. Thus, the image recording apparatus 10 can extract and display an image showing an area of the observed person 915 which corresponds to the point of sight of the observer 910. With this configuration, the image recording apparatus 10 enables the observer 910 and other users to easily know which area of the observer person 915 the observer 910 pays attention to during the observation. Also, the image recording apparatus 10 can display the point of sight of the observer 910 together with the image of the observed person 915 which is captured while the observer 910 observes the observed person 915. Therefore, the image recording apparatus 10 makes it possible to reproduce how the observer 910 observes the observed person 915.

Furthermore, the image recording apparatus 10 relating to the present embodiment can identify the point of sight and view of the observer 910. When the point of sight of the observer 910 is present within the area occupied by the observed person 915, or when the observed person 915 is present within the view of the observer 910, the image recording apparatus 10 can extract the image of the observed person 915. In this manner, the image recording apparatus 10 can appropriately judge that the observer 910 pays attention to the observed person 915, and correctly extract the image of the observed person 915 which is captured when the observer 910 observes the observed person 915. Consequently, the image recording apparatus 10 can extract an image useful for the observation of the observed person 915.

In addition, the image recording apparatus 10 relating to the present embodiment can display, side by side, the current image of the observed person 915 and the previously captured image of the observed person 915. Therefore, the image recording apparatus 10 makes it possible to easily know the change of the status of the observed person 915. Also, the image recording apparatus 10 relating to the present embodiment can display, side by side, the current image of the observed person 915 which is captured when the observer 910 asks a certain question to the observed person 915 and the image of the observed person 915 which is captured when the observer 910 previously asks the same question to the observed person 915. In this way, the observer 910 can observe the status of the observed person 915 while comparing the current and previous facial expressions of the observed person 915 which are observed when the observer 910 asks the same question to the observed person 915.

Figure 5:
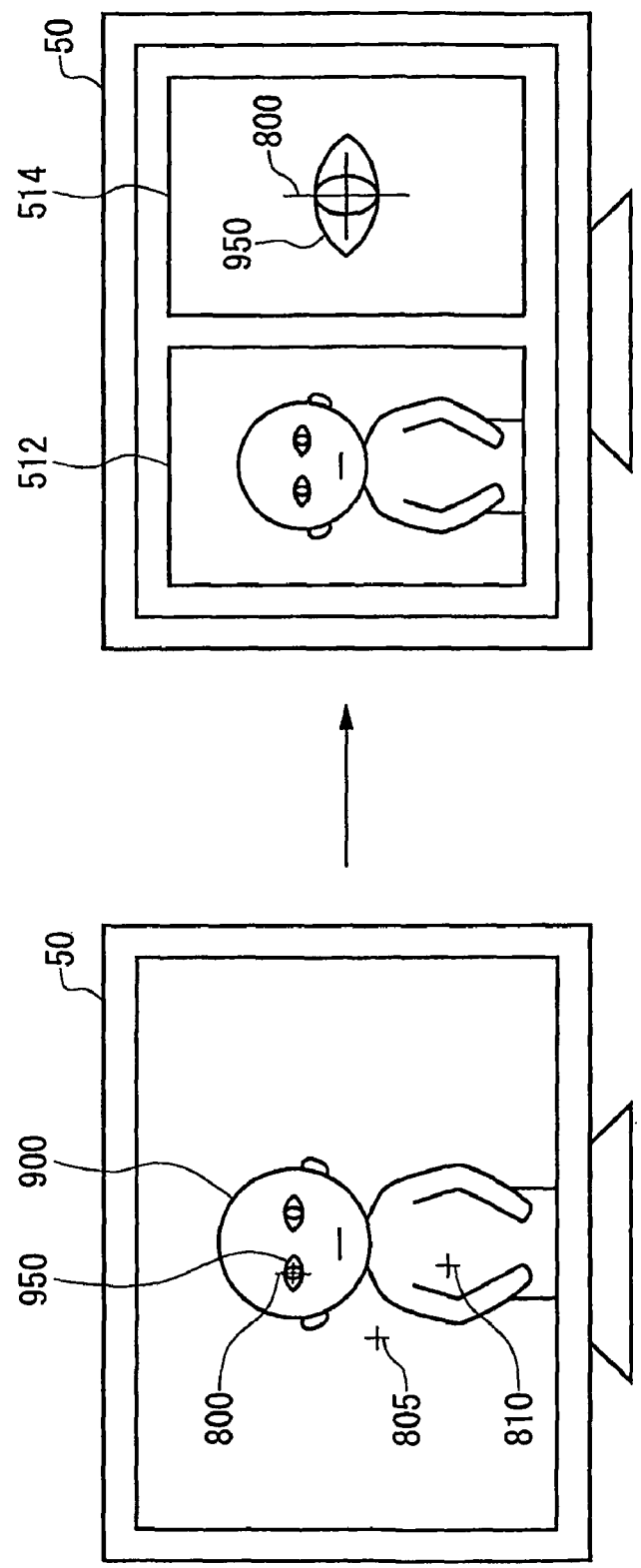
FIG. 5 illustrates the operation performed by a point of sight output control section 220.

FIG. 5 illustrates an exemplary operation performed by the point of sight output control section 220 relating to the present embodiment. The point of sight output control section 220 causes the image-capturing section 204 to capture an image of a person 900, who is the observed person 915, when the point of sight of the observer 910 is present within the area occupied by the person 900. Note that the point of sight output control section 220 judges whether the still time period of the point of sight which is measured by the view measuring section 230 is equal to or longer than a predetermined time period. When judging positively, the point of sight output control section 220 determines that the observer 910 pays attention to the area including the point of sight. Subsequently, the point of sight output control section 220 extracts the image of the person 900 and a partial image of the person 900 which includes the point of sight.

A case is assumed where the point of sight of the observer 910 is at positions indicated by a mark 800, a mark 805 and a mark 810, for example. Here, if the still time period of the point of sight at the position indicated by the mark 800 is equal to or longer than a predetermined time period, the point of sight output control section 220 extracts an image of an area corresponding to an eye 950 of the person 900 which includes the point of sight indicated by the mark 800. Following this, the point of sight output control section 220 enlarges the extracted image to obtain an enlarged image 514, and outputs the enlarged image 514 to the output section 50. Here, the point of sight output control section 220 may cause the output section 50 to output an image 512 including the entire body of the person 900 along with the enlarged image 514. In the enlarged image 514, the region including the eye 950 of the person 900 is displayed in the enlarged state.

The point of sight output control section 220 relating to the present embodiment can enlarge a portion of the area occupied by the observed person 915 to which the observer 910 pays attention, and display, side by side, the enlarged image and the image of the observed person 915. Thus, it is possible to reproduce the observation done by the observer 910 in such a manner as to make it possible for a user of the image recording apparatus 10 to meticulously observe the area to which the observer 910 pays attention while observing the observed person 915. Also, the user of the image recording apparatus 10 can learn the procedure used by the observer 910 to do observation with reference to the observation done by the observer 910 which is reproduced by the image recording apparatus 10.

Figure 6:
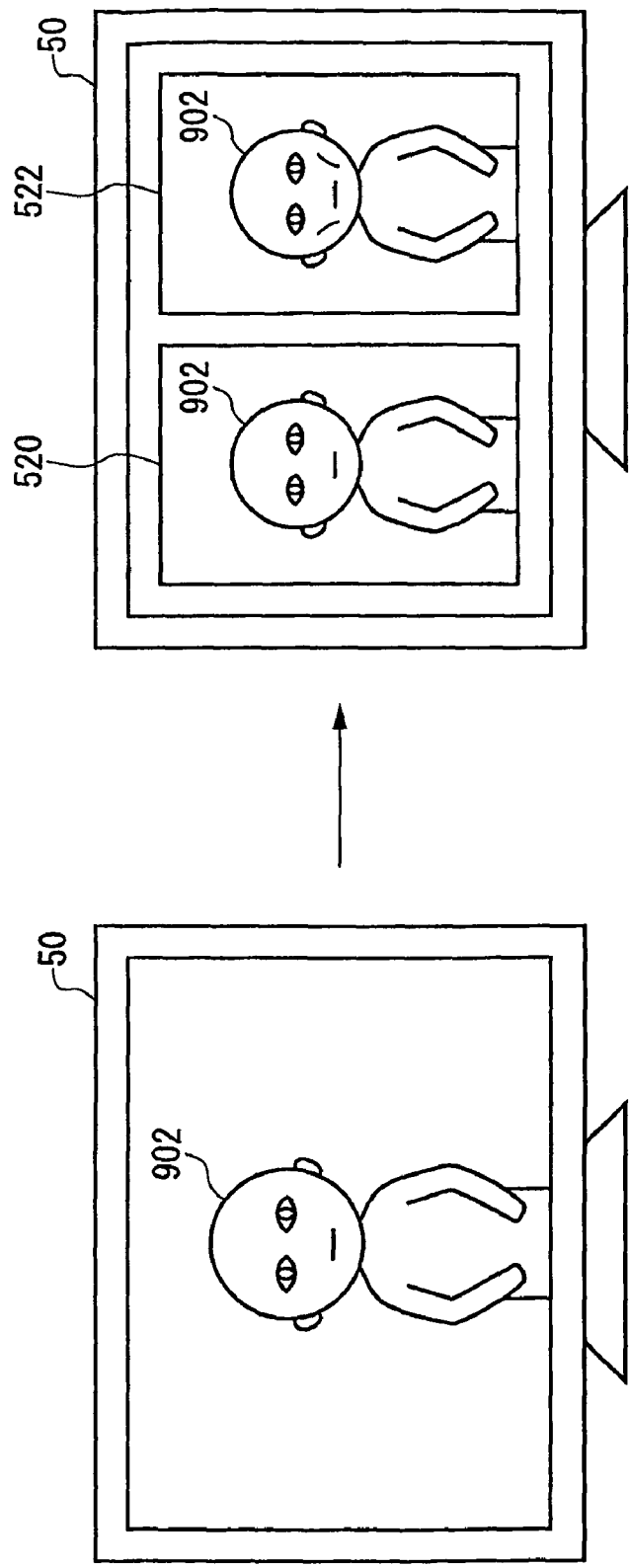
FIG. 6 illustrates the operation performed by a previous image output control section 310.

FIG. 6 illustrates an exemplary operation performed by the previous image output control section 310 relating to the present embodiment. The previous image output control section 310 extracts a previous image of a person 902, who is the observed person 915 being observed by the observer 910, which is stored on the observed person's information storing section 300 in association with the person 902. Subsequently, the previous image output control section 310 causes the output section 50 to output, side by side, a current image 520 of the person 902 which is captured by the image-capturing section 204 and a previous image 522 including the person 902. The previous image of the person 902 which is extracted by the previous image output control section 310, for example, the image 522, may be an image of the person 902 which is captured at the first visit, an image of the person 902 which is captured when the person 902 is observed last time, or an image of the person 902 which is captured at a date and a time designated by the observer 910.

To be specific, the input unit 60 provided in the image recording apparatus 10 may include therein an image-capturing time input section. The image-capturing time input section allows the observer 910 to input a date and a time at which an image of the observed person 915 is captured. The image-capturing time input section supplies the date and time input by the observer 910 to the previous image output control section 310. The previous image output control section 310 extracts an image of the observed person 915 which is captured at the date and time received from the image-capturing time input section, and causes the output section 50 to output the extracted image.

The previous image output control section 310 relating to the present embodiment can cause the output section 50 to display, side by side, the current and previous images of the observed person 915. Therefore, the observer 910 can perform accurate observation by comparing the current and previous facial expressions of the person 902.

Figure 7:
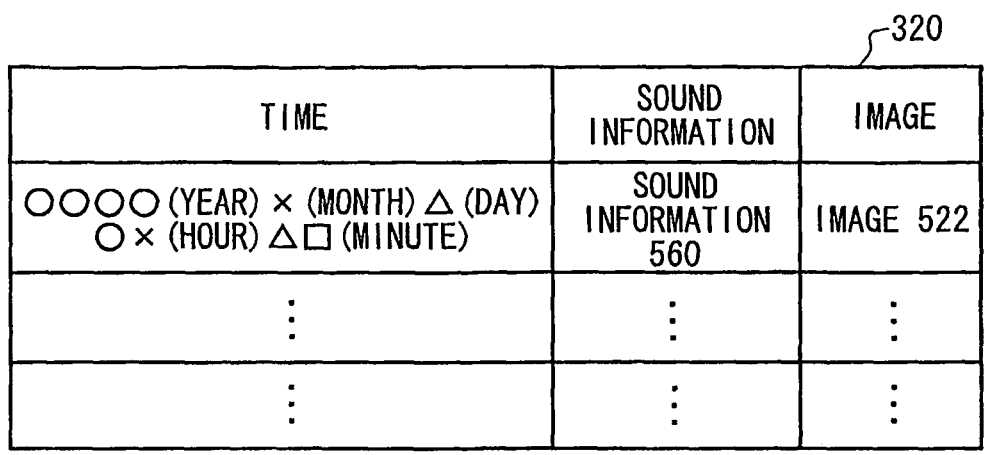
FIG. 7 illustrates the structure of data stored on an image storing section 320.

FIG. 7 illustrates an exemplary structure of data stored on the image storing section 320 relating to the present embodiment. The image storing section 320 stores thereon the sound information of the observer 910 and the image of the observed person 915. To be specific, the image storing section 320 stores thereon, in association with a time at which sound information 560 of the observer 910 is recorded by the sound recording section 400, an image 522 of the observed person 915 which is captured by the image-capturing section 204 at the time and the sound information 560 of the observer 910.

For example, the sound recording section 400 records the sound information 560 which is obtained when the observer 910 asks a question to the observed person 915. The sound recording section 400 supplies the sound information 560 to the image storing section 320 and sound information comparing section 410. The image storing section 320 stores the image 522 of the observed person 915 which is received from the image-capturing section 204 and the sound information 560 which is received from the sound recording section 400, in association with the time at which the sound recording section 400 records the sound information 560. The image storing section 320 supplies the sound information 560 to the sound information comparing section 410 under the control of the sound information comparing section 410. The sound information comparing section 410 compares sound information of the observer 910 which is newly recorded by the sound recording section 400 with the previous sound information 560 of the observer 910 which is stored on the image storing section 320, to calculate a coincidence level between the newly recorded sound information and the previous sound information 560. When the coincidence level calculated by the sound information comparing section 410 is equal to or higher than the predetermined coincidence level, the previous image output control section 310 extracts the image 522 from the image storing section 320, and causes the output section 50 to output the extracted image 522 together with the current image of the observed person 915. In this way, the image recording apparatus 10 makes it possible to later reproduce a previously asked question and to reproduce the behavior of the observed person 915 which is observed when the question is previously asked.

The image recording apparatus 10 relating to the present embodiment can be utilized in the medical field. To be specific, the image recording apparatus 10 is used as a diagnosis assisting apparatus that records thereon the contents of the diagnoses made for patients. For example, the image recording apparatus 10 is a diagnosis assisting apparatus that records thereon the contents of the diagnoses made for patients, the observed person is a patient suffering from a mental disease, and the observer is a medical doctor who observes the patient. When the observed person 915 is a patient suffering from a mental disease, the medical doctor often diagnoses the patient with focusing on an area of the patient which is likely to show the tension. The image recording apparatus 10 relating to the present embodiment makes it possible to easily reproduce at a later time than the diagnosis which area of the patient the medical doctor pays attention to during the diagnosis. For this reason, it is highly useful to use the image recording apparatus 10 for assisting the diagnoses of patients suffering from mental diseases.

Figure 8:
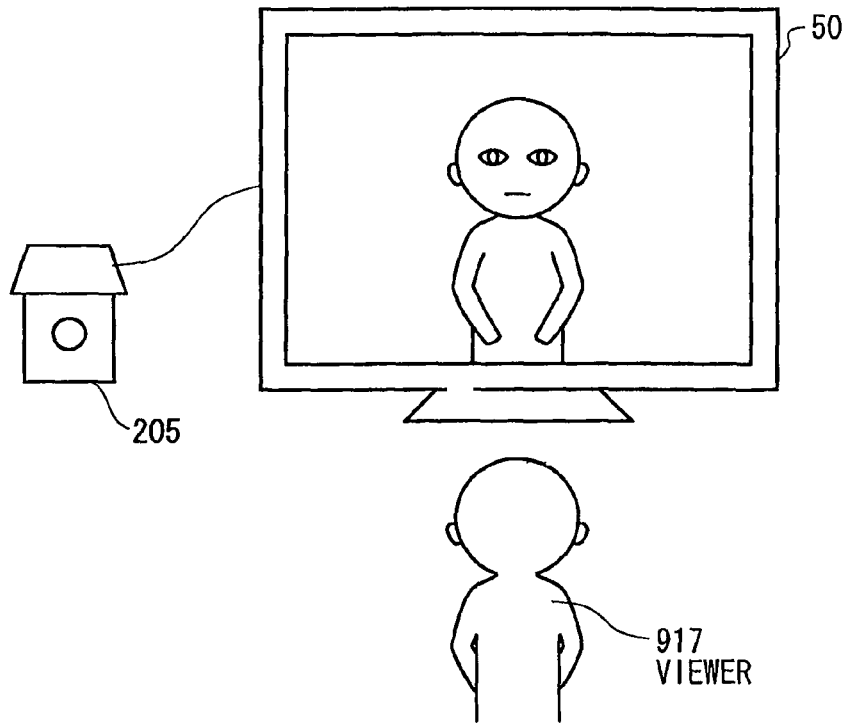
FIG. 8 is used to illustrate another example of the image-capturing unit 20 relating to a first embodiment.

FIG. 8 is used to illustrate another example of the image-capturing unit 20 relating to the first embodiment. The image-capturing unit 20 further includes therein an image-capturing section 205, a viewer's point of sight measuring section 271, and a viewer's point of sight judging section 272. Here, the storing unit 30 may further include therein a viewed image extracting section 312. As described above, the observed person's information storing section 300 stores thereon the images of the observed person 915 which are captured by the image-capturing sections 204 and 206, in association with the information indicating the point of sight of the observer 910 which is measured by the observer's point of sight measuring section 210. Here, the previous image output control section 310 reads the image of the observed person 915 which is stored on the observed person's information storing section 300, and causes a display section of the output section 50 to display the read image. This operation is shown in FIG. 8. In this case, the point of sight output control section 220 does not cause the output section 50 to display the mark indicating the position of the point of sight of the observer 910. The image-capturing section 205 captures an image of the viewer who views the image of the observed person 915 which is displayed on the display section of the output section 50, and supplies the captured image of the viewer to the viewer's point of sight measuring section 271.

The viewer's point of sight measuring section 271 measures the point of sight of the viewer who views the image of the observed person 915 which is displayed on the output section 50. Here, the viewer may or may not be the observer 910. For example, when the observer 910 is a medical doctor, the viewer is another medical doctor, a nurse, or an intern. The viewer's point of sight measuring section 271 identifies an area of the observed person 915 displayed on the display section of the output section 50 in which the point of sight of the viewer is present, and supplies information indicating the point of sight of the viewer to the viewer's point of sight judging section 272 and observed person's information storing section 300. Here, the viewer's point of sight measuring section 271 may measure the point of sight of the viewer in the same manner as the observer's point of sight measuring section 210, observed person's point of sight measuring section 214 and view measuring section 230. In FIG. 8, the image-capturing section 205 is shown as a camera that is fixed at a remote position from the viewer, for example. However, the image-capturing section 205 may be a head-mounted camera to be mounted on the head of the viewer. If such is the case, the positions of the eyeballs of the viewer with respect to the coordinate system of the camera are in advance calibrated. Also, the positional relation between the viewer and the display screen of the output section 50 is identified in advance. Here, the point of sight of the viewer may be identified by measuring the movement of the eyeballs of the viewer based on, for example, the corneal reflex method. The observed person's information storing section 300 further stores thereon the point of sight of the viewer which is measured by the viewer's point of sight measuring section 271, in association with the image of the observed person 915 which is read by the previous image output control section 310.

The viewer's point of sight judging section 272 judges whether the point of sight of the observer 910 which is measured by the observer's point of sight measuring section 210 and the point of sight of the viewer which is measured by the viewer's point of sight measuring section 271, and supplies the result of the judgment to the viewed image extracting section 312. To be specific, the viewer's point of sight judging section 272 judges whether the information indicating the point of sight of the observer 910 which is stored on the observed person's information storing section 300 coincides with the point of sight of the viewer. When the viewer's point of sight judging section 272 judges negatively, the viewed image extracting section 312 extracts the image of the observed person 915 which corresponds to the information indicating the points of sight do not coincide with each other. The previous image output control section 310 causes the output section 50 to output the image of the observed person 915 which corresponds to the information indicating that the points of sight do not coincide with each other and thus is extracted by the viewed image extracting section 312. This configuration enables the viewer to look at the movement of the point of sight of the observer 910 and the movement of the viewer's own point of sight. According to the present embodiment, the image is output when the points of sight do not coincide with each other. In this way, the viewer can easily retrieve an image corresponding to a case where the viewer uses a different observation procedure from the observer 910. This configuration can help the viewer efficiently learn where to pay attention to, especially when the viewer is an intern.

The point of sight output control section 220 may cause the output section 50 to output at least one of the marks respectively indicating the position of the point of sight of the observer 910 which is measured by the observer's point of sight measuring section 210 and the position of the point of sight of the viewer which is measured by the viewer's point of sight measuring section 271, in such a state that the mark is overlapped onto the image of the observed person 915. Since the mark indicating the point of sight of the observer 910 is displayed, the viewer can easily know which part the viewer is supposed to pay attention to. In addition to the mark indicating the point of sight of the observer 910, the mark indicating the viewer's point of sight is also displayed. In this way, the viewer can objectively realize an error.

Figures 9A, 9B:
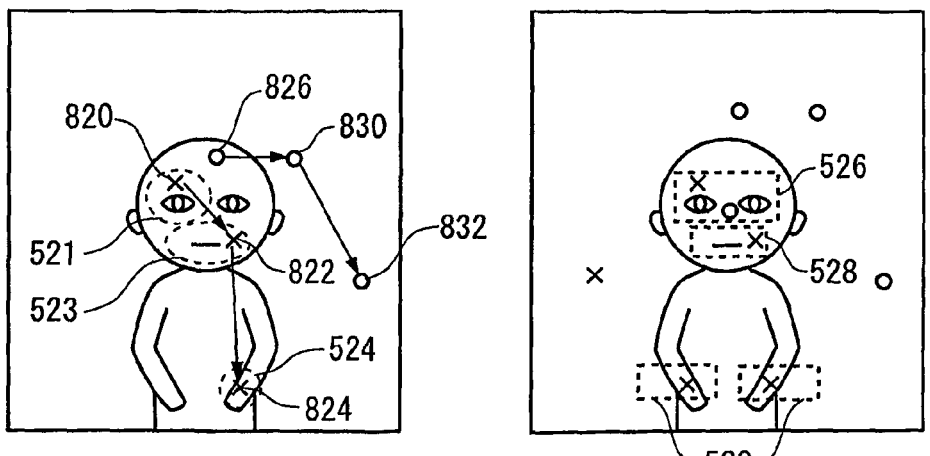
FIGS. 9A and 9B are used to illustrate the operation performed by a viewer's point of sight judging section 272.

FIG. 9 is used to illustrate the operation performed by the viewer's point of sight judging section 272. The viewer's point of sight judging section 272 judges that the points of sight of the viewer 917 and observer 910 do not coincide with each other, when the point of sight of the viewer which is measured by the viewer's point of sight measuring section 271 is not present within a predetermined region including the point of sight of the observer 910 which is measured by the observer's point of sight measuring section 210. Here, the predetermined region including the point of sight of the observer 910 which is measured by the observer's point of sight measuring section 210 is determined based on the position of the point of sight of the observer 910. For example, a region 521 is determined based on a point of sight 820 of the observer which is measured by the observer's point of sight measuring section 210 as shown in FIG. 9A. When the point of sight of the viewer which is measured by the viewer's point of sight measuring section 271 is not present within the region 521, the viewer's point of sight judging section 272 judges that the points of sight of the viewer 917 and observer 910 do not coincide with each other.

A case is assumed where the point of sight of the observer 910 which is measured by the observer's point of sight measuring section 210 moves to multiple different positions. In this case, the viewer's point of sight judging section 272 may judge that the points of sight coincide with each other if the point of sight of the viewer which is measured by the viewer's point of sight measuring section 271 moves to the vicinities which respectively correspond to the positions of the point of sight of the observer 910. Here, the vicinities of the positions may be regions which are determined in accordance with the point of sight of the observer 910 which is measured by the observer's point of sight measuring section 210. Furthermore, the viewer's point of sight judging section 272 may judge that the points of sight coincide with each other when the point of sight of the viewer which is measured by the viewer's point of sight measuring section 271 moves to the vicinities in the same order as the point of sight of the observer 910. In the present embodiment, the viewer's point of sight judging section 272 judges negatively since none of the reference numerals 826, 830 and 832 indicating the point of sight of the viewer 917 is present within the regions 521, 523 and 524 determined based on the point of sight of the observer 910.

The viewer's point of sight judging section 272 may judge that the points of sight coincide with each other when the point of sight of the viewer 917 moves to the vicinities of the respective positions of the point of sight of the observer 910 which is measured by the observer's point of sight measuring section 210, irrespective of the movement order of the point of sight of the viewer 917. Here, the predetermined regions each including the point of sight of the observer 910 may be defined by circles, squares or rectangles with the point of sight of the observer 910 being set as the center. In addition, the predetermined regions each including the point of sight of the observer 910 may each have a size determined in accordance with at least one of the movement rates of the points of sight of the observer 910 and viewer 917. For example, when the movement rate of the point of sight of the observer 910 is higher than a predetermined rate, the viewer's point of sight judging section 272 may set a larger size to the predetermined regions each including the point of sight of the observer 910. Meanwhile, when the movement rate of the point of sight of the viewer 917 is lower than a predetermined rate, the viewer's point of sight judging section 272 may set a larger size to the predetermined regions each including the point of sight of the observer 910. Here, the predetermined rate may be equal to the average rate of the movement of the point of sight of the observer 910 displayed on the output section 50, or the average of the movement rates of the points of sight of multiple observers which are stored on the image storing section 320. Alternatively, the predetermined rate may be equal to the average rate of the movement of the point of sight of the viewer 917, or the average of the movement rates of the points of sight of multiple viewers.

As an alternative example, the viewer's point of sight judging section 272 may judge that the points of sight coincide with each other when the point of sight of the observer 910 which is measured by the observer's point of sight measuring section 210 and the point of sight of the viewer which is measured by the viewer's point of sight measuring section 271 are both present within a predetermined region of the image of the observed person 915 which is captured by the image-capturing section 206, as described with reference to FIG. 9B. According to the present embodiment, the predetermined region of the image of the observed person 915 is made up by a plurality of separate regions which respectively include therein at least the eyes, mouth and hands of the observed person 915. In detail, the region including the eyes may be a region corresponding to the black part (pupil and iris) of one of the eyes, a region corresponding to the black and white areas of one of the eyes, or a predetermined circular, rectangular or oval region including the black and white parts of one of the eyes. Alternatively, the region including the eyes may be a predetermined circular, rectangular or oval region including both eyes. The region including the mouth may be a region corresponding to the lips, a region defined by the lips, or a predetermined circular, rectangular or oval region including the lips. The region including the hands may be a region corresponding to the palm or back of one of the hands or a predetermined circular, rectangular or oval region including the region corresponding to the palm or back of one of the hands. Alternatively, the region including the hands may be a predetermined circular, rectangular or oval region including the palms or backs of both hands. The regions 526, 528 and 530 are shown in FIG. 9B as examples of the regions respectively including the eyes, mouth, and hands of the observed person 915. According to the present embodiment, since the points of sight of the observer 910 and viewer 917 are both present in the region 526, the viewer's point of sight judging section 272 judges that the points of sight coincide with each other. With the above-described configuration, the image recording apparatus 10 can easily make a judgment whether the points of sight coincide with each other.

Alternatively, the viewer's point of sight judging section 272 may make the judgment whether the points of sight coincide with each other by additionally taking into consideration the order in which the point of sight of the observer 910 moves. As another alternative example, the viewer's point of sight judging section 272 may make the judgment whether the points of sight coincide with each other based on the respective likelihoods at which the points of sight of the observer 910 and viewer which are measured by the observer's point of sight measuring section 210 and viewer's point of sight measuring section 271 are present within the predetermined region of the image of the observed person 915 during a predetermined time period. Here, when the points of sight move to multiple different positions during the predetermined time period, the viewer's point of sight judging section 272 may calculate those likelihoods by calculating a total time period for which each of the points of sight stays still in each of the multiple predetermined regions, for example. The viewer's point of sight judging section 272 obtains a coincidence level between the likelihoods which are calculated for the observer and viewer with respect to each predetermined region, and judges that the points of sight coincide with each other when the coincidence level is equal to or higher than a predetermined level.

Figures 10, 11:
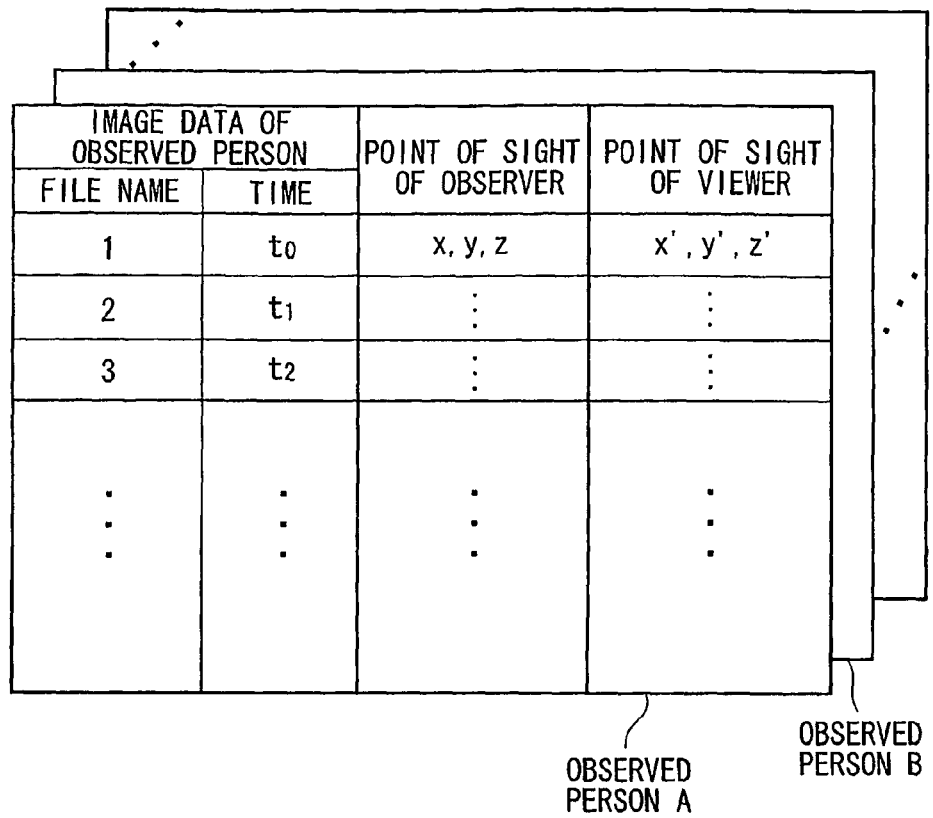
FIG. 10 illustrates exemplary data stored on an observed person's information storing section 300.
FIG. 11 is used to illustrate the operation in which an image is extracted by a viewed image extracting section 312 and the extracted image is output by an output section 50.

FIG. 10 illustrates an example of the data stored on the observed person's information storing section 300. The observed person's information storing section 300 relating to the present embodiment stores thereon, for each observed person, the image of the observed person 915 captured by the image-capturing section 206 together with the information indicating the point of sight of the observer 910 which is measured by the observer's point of sight measuring section 210. The observed person's information storing section 300 relating to the present embodiment stores thereon the image of the observed person 915 which is captured by the image-capturing section 206 together with the information indicating the time and the coordinate data indicating the point of sight of the observer 910. Also, the observed person's information storing section 300 relating to the present embodiment stores thereon the coordinate data indicating the point of sight of the viewer 917 together with the coordinate data indicating the point of sight of the observer 910.

FIG. 11 is used to illustrate the operation in which the image extracted by the viewed image extracting section 312 is output by the output section 50. Based on the judgment made by the viewer's point of sight judging section 272, the viewed image extracting section 312 extracts an image of the observed person 915 which is stored in association with the coordinate data indicating the point of sight that does not show the coincidence, and the previous image output control section 310 causes the output section 50 to output the image extracted by the viewed image extracting section 312. Here, the previous image output control section 310 may cause the output section 50 to output a plurality of images extracted by the viewed image extracting section 312 to reproduce a single continuous moving image. Alternatively, the previous image output control section 310 may cause the output section 50 to play back the images corresponding to no coincidence at a normal speed, and play back the images corresponding to coincidence at a higher speed than normal. In this way, the image recording apparatus 10 relating to the present embodiment can select and output the images corresponding to no coincidence between the points of sight of the observer and viewer within a brief time period. This configuration enables the viewer to easily look at the images corresponding to no coincidence.

Figure 12:
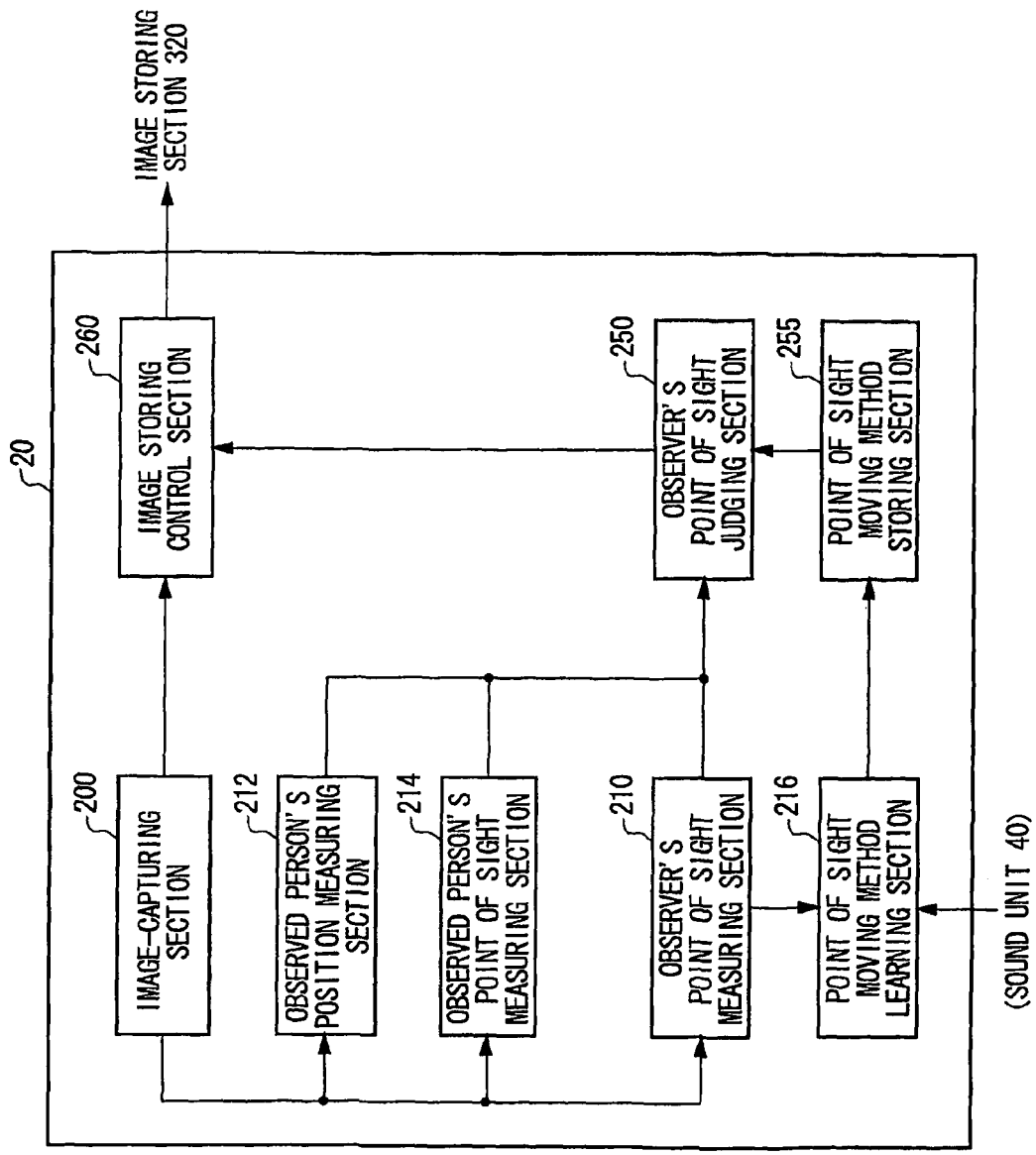
FIG. 12 illustrates an exemplary functional configuration of the image-capturing unit 20 relating to a second embodiment.

FIG. 12 illustrates an exemplary functional configuration of the image-capturing unit 20 relating to a second embodiment. The image-capturing unit 20 relating to the present embodiment includes therein an image-capturing section 200, the observer's point of sight measuring section 210, the observed person's position measuring section 212, the observed person's point of sight measuring section 214, a point of sight moving method learning section 216, the observer's point of sight judging section 250, a point of sight moving method storing section 255, and an image storing control section 260. The present embodiment provides an image recording apparatus for accurately recording the change in the facial expressions of the observed person 915 during conversation. The image-capturing unit 20 relating to the present embodiment may further include some or all of the functions and constituents of the units which together constitute the image recording apparatus 10 described with reference to FIGS. 1 to 11. In the following description, the constituents assigned with the same reference numerals as in FIGS. 1 to 11 have substantially the same functions as the corresponding constituents described with reference to FIGS. 1 to 11, and therefore not explained in detail.

When the image-capturing section 200 is an omnidirectional camera, for example, the image-capturing section 200 may have the functions of the image-capturing sections 202, 204, 206 and 208 described with reference to FIGS. 1 to 11. Alternatively, the image-capturing unit 20 may include therein, in place of the image-capturing section 200, the image-capturing section 202 for detecting the point of sight of the observer 910, the image-capturing section 208 for measuring the area in which the observer 910 is present, the image-capturing section 204 for detecting the point of sight of the observed person 915, and the image-capturing section 206 for measuring the area in which the observed person 915 is present, similarly to the embodiment described with reference to FIGS. 1 to 11.

The image-capturing section 200 supplies the captured image of the observed person 915 to the image storing control section 260 under the control of the image storing control section 260. Also, the image-capturing section 200 supplies the image used for measuring the point of sight of the observed person 915 to the observed person's point of sight measuring section 214, and supplies the image used for measuring the position at which the observed person 915 is present to the observed person's position measuring section 212. Furthermore, the image-capturing section 200 supplies the image used for measuring the point of sight of the observer 910 to the observer's point of sight measuring section 210. The observer's point of sight measuring section 210 measures the point of sight of the observer 910 when the image-capturing section 200 captures the image of the observed person 915. In addition, the observer's point of sight measuring section 210 further measures how the observer 910 directs the line of sight towards the observed person 915 when the image-capturing section 200 captures the image of the observed person 915. Specifically speaking, the observer's point of sight measuring section 210 relates the point of sight of the observer 910 to a time of measuring the point of sight of the observer 910, to measure the trajectory of the point of sight of the observer 910. The observer's point of sight measuring section 210 further measures the movement rate of the point of sight of the observer 910 when the image-capturing section 200 captures the image of the observed person 915.

To be specific, the observer's point of sight measuring section 210 may measure the point of sight of the observer 910 at predetermined time intervals. For example, the observer's point of sight measuring section 210 measures the point of sight of the observer 910 at a first time and then at a second time. The observer's point of sight measuring section 210 measures the movement rate of the point of sight based on a time period calculated by using the first and second times and a distance calculated by using the points of sight measured at the first and second times. The observer's point of sight measuring section 210 supplies the trajectory and movement rate of the point of sight of the observer 910 to the observer's point of sight judging section 250 and point of sight moving method learning section 216.

The observed person's position measuring section 212 measures an area, within a predetermined image-capturing target area of the image-capturing section 200, in which the observed person 915 is present. Here, the observed person's position measuring section 212 obtains the position at which the observed person 915 is present in the form of coordinate data defined in accordance with a predetermined three-dimensional coordinate system within the image-capturing target area. The observed person's position measuring section 212 relating to the present embodiment measures an area corresponding to the face of the observed person 915. The observed person's position measuring section 212 may also measure an area corresponding to the eyes of the observed person 915. For example, the observed person's position measuring section 212 extracts a region of the face of the observed person 915 based on edge detection and skin color extraction from the image captured by the image-capturing section 200. The observed person's position measuring section 212 then measures the area corresponding to the eyes of the observed person 915, which is included in the extracted region of the face of the observed person 915. The observed person's position measuring section 212 supplies the coordinate data indicating the area in which the observed person 915 is present and the coordinate data indicating the area corresponding to the eyes, to the observer's point of sight judging section 250.

The observed person's point of sight measuring section 214 measures the point of sight of the observed person 915. To be specific, the observed person's point of sight measuring section 214 may include therein a first observed person's line of sight measuring section for measuring the line of sight of the left eye of the observed person 915 and a second observed person's line of sight measuring section for measuring the line of sight of the right eye of the observed person 915. The first and second observed person's line of sight measuring sections measure the directions of the lines of sight of the left and right eyes of the observed person 915. For example, the first and second observed person's line of sight measuring sections may calculate the lines of sight of the left and right eyes of the observed person 915 in the same manner as the first and second observer's line of sight measuring sections. Here, by defining a three-dimensional coordinate system in advance, coordinate data can be generated which indicates the directions in which the lines of sight of the observed person 915 measured by the observed person's point of sight measuring section 214 are directed with respect to the observed person 915.

The image-capturing unit 20 may further include therein the observer's position measuring section 270 for measuring the position at which the observer 910 is present within the predetermined image-capturing target area of the image-capturing section 200. The observer's position measuring section 270 measures the position, within the image-capturing target area, at which the observer 910 is present. The observer's position measuring section 270 obtains coordinate data that indicates the position at which the observer 910 is present in accordance with the three-dimensional coordinate system defined in advance within the image-capturing target area. The observer's position measuring section 270 may determine both positions of the observer 910 and observed person 915 in the same coordinate system. The observer's position measuring section 270 obtains a plurality of pieces of coordinate data included in the area in which the observer 910 is present, in order to identify the area occupied by the observer 910.

The observed person's point of sight measuring section 214 measures the area of the observer 910 at which the point of sight of the observed person 915 is present, based on the coordinate data indicating the area within which the observer 910 is present which is obtained by the observer's position measuring section 270 and the directions of the lines of sight of the observed person 915 which are measured by the observed person's point of sight measuring section 214. To be specific, the observed person's point of sight measuring section 214 judges, as the point of sight of the observed person 915, an intersecting point between the area occupied by the observer 910 which is identified by the pieces of coordinate data which are obtained by the observer's position measuring section 270 and an extended line of the line of sight of the observed person 915 which is measured by the observed person's point of sight measuring section 214. The observed person's point of sight measuring section 214 obtains the coordinate data indicating the intersecting point as coordinate data indicating the point of sight of the observed person 915.

Similarly to the observer's point of sight measuring section 210, the observed person's point of sight measuring section 214 may include therein an observed person's characteristic point extracting section for extracting characteristic points of the eyes and the like of the observed person 915. The observed person's characteristic point extracting section extracts the characteristic points of the observed person 915. When the observed person 915 moves the head, the observed person's point of sight measuring section 214 may trace the extracted characteristic points of the eyes and the like so as to follow the movement of the observed person 915, and measure the line of sight of the observed person 915. To be specific, the observed person's point of sight measuring section 214 may include therein a movement control section for moving the image-capturing section 200 that captures images of the observed person 915 in accordance with the movement of the characteristic points of the observed person 915 which are extracted by the observed person's characteristic point extracting section. The observed person's point of sight measuring section 214 supplies information indicating the measured point of sight of the observed person 915 to the observer's point of sight judging section 250.

The point of sight moving method learning section 216 learns how the observer 910 directs the line of sight towards the observed person 915, and supplies information indicating the learned method of how to direct the line of sight of the observer 910 towards the observed person 915, to the point of sight moving method storing section 255. According to the present embodiment, the point of sight moving method learning section 216 learns how the observer 910 habitually moves the line of sight based on the sound made when the observer 910 asks a question to the observed person 915 and the trajectory of the movement of the point of sight of the observer 910. The operation performed by the point of sight moving method learning section 216 is described later in detail.

The point of sight moving method storing section 255 stores thereon a predetermined method of how the observer 910 directs the line of sight towards the observed person 915. When there are a plurality of observers, the point of sight moving method storing section 255 may store thereon one or more methods of how each observer directs the line of sight. The point of sight moving method storing section 255 stores thereon the information indicating the method of how to direct the line of sight which is received from the point of sight moving method learning section 216 in association with the observer. The point of sight moving method storing section 255 supplies the information indicating the method of how the observer 910 directs the line of sight, to the observer's point of sight judging section 250. The observer's point of sight judging section 250 judges whether the point of sight of the observer 910 which is received from the observer's point of sight measuring section 210 is present within a predetermined area. To be specific, the observer's point of sight judging section 250 judges whether the point of sight of the observer 910 is present within the area in which the observed person 915 is present.

The observed person's position measuring section 212 may obtain, as the area in which the observed person 915 is present, a plurality of pieces of coordinate data determined in accordance with the predetermined three-dimensional coordinate system for the image-capturing target area of the image-capturing section 200, for example. By comparing the direction of the line of sight of the observer 910 with the coordinate data indicating the area in which the observed person 915 is present, the observer's point of sight judging section 250 may make the judgment whether the point of sight of the observer 910 is present within the area in which the observed person 915 is present. The observer's point of sight judging section 250 may also judge whether the point of sight of the observer 910 is present within the area corresponding to the eyes of the observed person 915. Also, the observer's point of sight judging section 250 further judges whether the trajectory of the point of sight of the observer 910 which is received from the observer's point of sight measuring section 210 coincides with the trajectory of the point of sight indicated by the information indicating the method of how to direct the line of sight which is received from the point of sight moving method storing section 255. The observer's point of sight judging section 250 may additionally judge whether the movement rate of the point of sight of the observer 910 which is measured by the observer's point of sight measuring section 210 falls within a predetermined range.

The observer's point of sight judging section 250 judges whether the lines of sight of the observer 910 and observed person 915 coincide with each other based on the point of sight of the observed person 915 which is received from the observed person's point of sight measuring section 214 and the point of sight of the observer 910 which is received from the observer's point of sight measuring section 210. For example, the observer's point of sight judging section 250 may judge that the lines of sight of the observer 910 and observed person 915 coincide with each other if the point of sight of the observer 910 which is measured by the observer's point of sight measuring section 210 is present within the area corresponding to the eyes of the observed person 915 and the point of sight of the observed person 915 which is measured by the observed person's point of sight measuring section 214 is present within the area corresponding to the eyes of the observer 910. The observer's point of sight judging section 250 supplies the result of the judgment to the image storing control section 260.

When receiving from the observer's point of sight judging section 250 a result of judgment indicating that the point of sight of the observer 910 is present within the predetermined area, the image storing control section 260 obtains the image of the observed person 915 from the image-capturing section 200, and stores the image onto the image storing section 320. Here, the predetermined area may be the area within which the observed person 915 is present, the area corresponding to the eyes of the observed person 915, or the like. Here, the image storing control section 260 may store, onto the image storing section 320, one or more images of the observed person 915 which are captured by the image-capturing section 200 during a predetermined time period starting from a time that precedes, by a predetermined time period, the time at which the observer's point of sight judging section 250 makes the judgment that the point of sight of the observer 910 is present within the predetermined area. When the observer's point of sight judging section 250 judges that the method of how the observer 910 directs the line of sight towards the observed person 915 coincides with the method of how to direct the line of sight which is stored on the point of sight moving method storing section 255, the image storing control section 260 may obtain the image of the observed person 915 from the image-capturing section 200 and stores the obtained image onto the image storing section 320.

Also, when the observer's point of sight judging section 250 judges that the movement rate of the line of sight of the observer 910 falls within the predetermined range, the image storing control section 260 may obtain the image of the observed person 915 from the image-capturing section 200 and store the obtained image onto the image storing section 320. The image storing control section 260 may store, onto the image storing section 320, a plurality of images of the observed person 915 which are captured by the image-capturing section 200 before and after the time at which the observer's point of sight judging section 250 makes the judgment that the lines of sight of the observer 910 and observed person 915 coincide with each other. In addition, the image storing control section 260 may detect the sound that is made when the observer 910 asks a question to the observed person 915, obtain from the image-capturing section 200 the image of the observed person 915 which is captured by the image-capturing section 200 when the sound is detected, and store the obtained image onto the image storing section 320.

The image recording apparatus 10 relating to the present embodiment can automatically record an image showing an area of the region of the observed person 915 to which the observer 910 pays attention, at a timing at which the observer 910 pays attention to the observed person 915, while the point of sight of the observer 910 is present within the predetermined area, that is to say, while the observer 910 is observing the observed person 915. This configuration makes it possible to easily reproduce, at a later time than the observation, the image showing an area of the observed person 915 which is captured when the observer 910 pays attention to the observed person 915 while observing the observed person 915.

Also, the image recording apparatus 10 relating to the present embodiment can record the image of the observed person 915 if the movement rate of the point of sight of the observer 910 falls within the predetermined range. In other words, the image recording apparatus 10 does not record thereon the image of the observed person 915 when the observer 910 does not pay attention to the observed person 915, for example, when the movement rate of the point of sight of the observer 910 is higher than a predetermined rate. Consequently, while the observer 910 observes the observed person 915, the image recording apparatus 10 can only record appropriate images of the observed person 915 which are captured when the observer 910 pays attention to the observed person 915.

In addition, the image recording apparatus 10 relating to the present embodiment can record the image of the observed person 915 when the points of sight of the observer 910 and observed person 915 coincide with each other. With this configuration, the image recording apparatus 10 relating to the present embodiment can reproduce the image of the observed person 915 which is captured when the points of sight of the observer 910 and observed person 915 coincide with each other, together with the sound information of the observer 910 in relation to a health interview, for example. Therefore, the image recording apparatus 10 relating to the present embodiment can easily reproduce the facial expressions presented by the observed person 915 in response to the questions asked by the observer 910.

Figure 13:
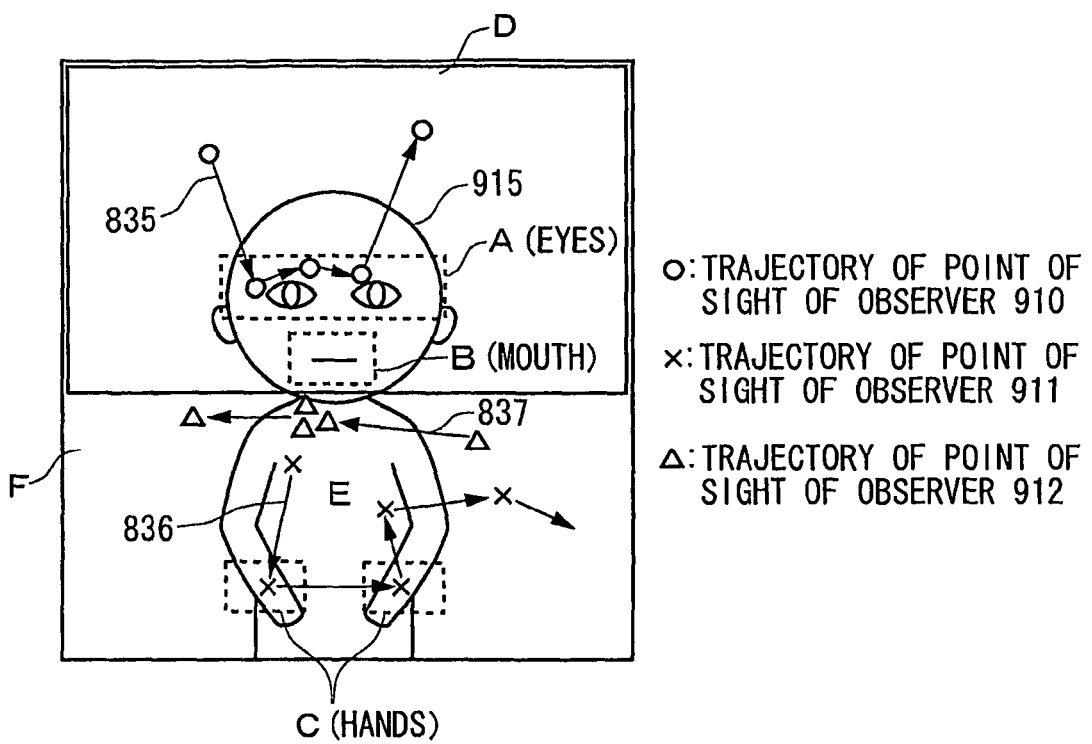
FIG. 13 is used to illustrate the operation performed by a point of sight moving method learning section 216.

FIGS. 13, 14 and 15 are used to illustrate the operation performed by the point of sight moving method learning section 216. FIG. 13 schematically illustrates trajectories 835, 836 and 837 of the point of sight which are obtained when different observers 910, 911 and 912 observe the observed person 915. As seen from FIG. 13, each observer has a different method of directing the line of sight towards the observed person 915. Therefore, the point of sight moving method learning section 216 identifies a unique method of moving the point of sight for each observer. To be specific, the point of sight moving method learning section 216 relating to the present embodiment identifies a unique method of moving the point of sight for each observer, by identifying a region in which the point of sight of the observer is likely to move while the observer is talking.

The point of sight moving method learning section 216 receives, from the observer's point of sight measuring section 210, the information indicating the point of sight of the observer 910 at predetermined time intervals. Also, the point of sight moving method learning section 216 receives from the sound unit 40 information indicating whether there is a sound, and when a sound is detected, identifies the region in which the point of sight of the observer is present. Here, the point of sight moving method learning section 216 may identify whether the point of sight of the observer is present in a predetermined region within the image of the observed person 915. In the present embodiment, for example, a plurality of regions are defined in advance within the image of the observed person 915, as shown in FIG. 13. For example, such regions include a region A (the eyes), a region B (the mouth), a region C (the hands), a region D (a portion of the image which shows the observed person from the neck up but excludes the face), a region E (the body), and a region F (the remaining portion). The point of sight moving method learning section 216 identifies the region in which the point of sight of the observer is present, in association with the information indicating whether there is a speech made by the observer. For each region, the point of sight moving method learning section 216 calculates the total time period for which the point of sight is present in the region. Based on this operation, the point of sight moving method learning section 216 identifies the region in which the point of sight is present for the longest period of time when the speech is made. In the case of the observer 910 shown in FIGS. 13 and 14, for example, the point of sight is present in the region D when the observer 910 does not make a speech, but the point of sight moves to the region corresponding to the eyes of the observed person (region A) when the observer 910 makes a speech. In the case of the observer 911, the point of sight moves to the region corresponding to the hands of the observed person (region C).

The point of sight moving method learning section 216 may also identify the region in which the point of sight is present for the longest time period when there is no speech made, by calculating the total time period for which the point of sight is present for each region. Alternatively, the point of sight moving method learning section 216 may calculate the likelihood at which the point of sight is present for each predetermined region. In the above-described manner, the point of sight moving method leaning section 216 learns how each observer directs the line of sight, and the point of sight moving method storing section 255 stores thereon the information regarding the learned method of how to direct the line of sight.

Here, the point of sight moving method learning section 216 may vary the sizes of the predetermined regions in the image of the observed person 915 in accordance with the learned methods of how to direct the line of sight. For example, the point of sight moving method learning section 216 varies the size of each predetermined region in the image of the observed person 915 in accordance with the period of time for which the point of sight is present in the region when the speech is made. To be specific, in the case of a predetermined region in which the point of sight is present for a long time period when a speech is made, the point of sight moving method learning section 216 reduces the size of the predetermined region. On the other hand, in the case of a predetermined region in which the point of sight is present for a short time period when a speech is made, the point of sight moving method learning section 216 increases the size of the predetermined region. Each observer uniquely behaves in a habitual manner when making a speech, for example, tends to stare at a particular area or move the point of sight frequently. According to the present embodiment, the sizes of the predetermined regions defined in the image of the observed person 915 are varied depending on the method of how the observer directs the line of sight. Therefore, the present embodiment can prevent unnecessary images which are captured when the point of sight moves differently from the habitual manner from being stored.

As indicated by the trajectory 837 of the observer 912 shown in FIG. 13, some observers may habitually observe patients without focusing the point of sight on a certain predetermined region (in FIG. 13, the region B). Taking such a habit into consideration, the point of sight moving method learning section 216 may identify the region in which the point of sight of the observer is highly likely to be present, and it may be judged that the methods of how to direct the line of sight coincide with each other when the point of sight of the observer 910 is present in the identified region.

In addition to the above-described factor, the point of sight moving method learning section 216 may use the movement rate to learn the method of how the observer directs the line of sight. For example, the point of sight moving method learning section 216 calculates the average movement rate of the point of sight of the observer while the sound unit 40 detects a sound. With this configuration, the point of sight moving method learning section 216 can know the habit of the observer 910 exhibited when the observer 910 directs the line of sight towards the observed person 915, for example, slowly moves the line of sight, quickly moves the line of sight, and stares at the observed person 915 during observation. The point of sight moving method storing section 255 stores thereon the average movement rate of the point of sight calculated for each observer. Also, the point of sight moving method learning section 216 may calculate, for each observer, the average movement rate of the point of sight while no sound is detected.

The observer's point of sight judging section 250 judges that the methods of how to direct the lines of sight coincide with each other, when the point of sight of the observer 910 is present while the observer 910 is making a speech, in the region to which the observer 910 is most likely to move the point of sight while making a speech, according to the information stored in the point of sight moving method storing section 255. Alternatively, the observer's point of sight judging section 250 may make the judgment that the methods of how to direct the lines of sight coincide with each other, when the point of sight of the observer 910 is present, while the observer 910 is making a speech, in the region to which the observer 910 is most likely to move the point of sight during a speech, and when the movement rate of the point of sight of the observer 910 during a speech is substantially equal to the average movement rate of the observer 910 during a speech, according to the information stored on the point of sight moving method storing section 255.

Here, by using the image recording apparatus relating to the present embodiment, the observer 910 may observe a plurality of observed persons. When the image captured by the image-capturing section 200 includes a plurality of observed persons, the image storing control section 260 extracts and stores the region indicating an observed person in which the point of sight of the observer 910 measured by the observer's point of sight measuring section 210 is included. In this case, the observer's point of sight judging section 250 judges whether the point of sight of the observer 910 measured by the observer's point of sight measuring section 210 is present within the region corresponding to the face of the observed person which is calculated by the observed person's position measuring section 212. When the observer's point of sight judging section 250 judges positively, the image storing control section 260 may store the image of the observed person 915 captured by the image-capturing section 200. Here, the image storing control section 260 may extract only a region showing the observed person who has the point of sight of the observer 910 measured by the observer's point of sight measuring section 210 and store the extracted region.

Figure 16A:
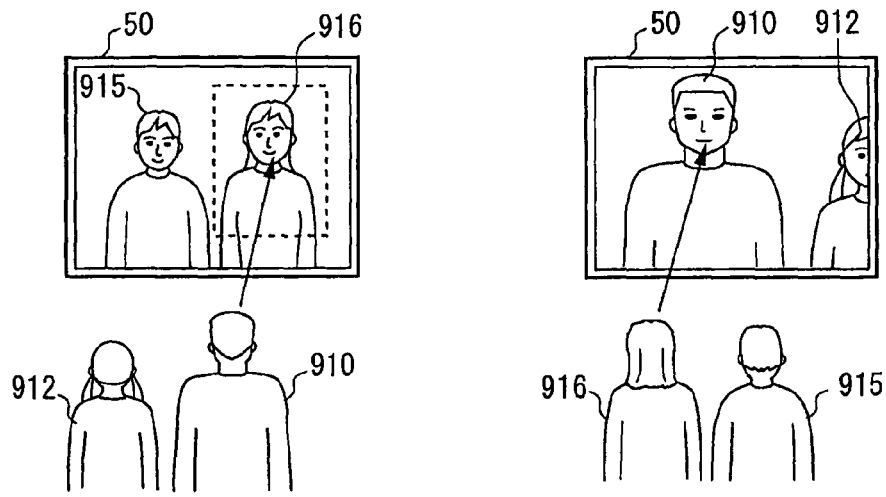
FIGS. 16A and 16B illustrate a case where the image recording apparatus 10 is used for a video conference.
Figure 16B:
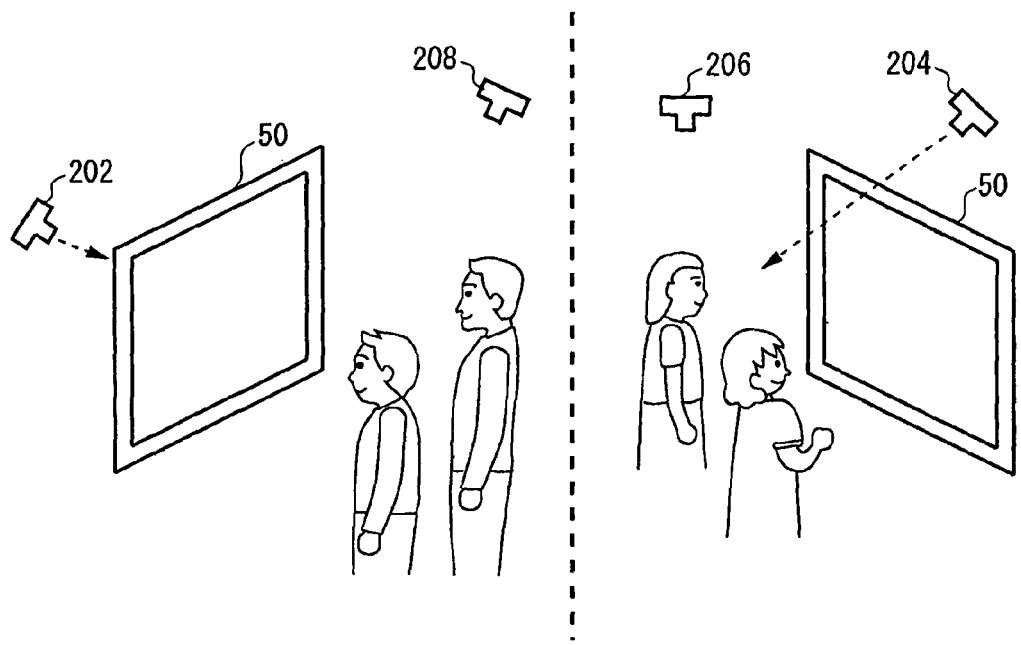

Similarly to the image recording apparatus 10 described with reference to FIGS. 1 to 11, the observer 910 may remotely observe the observed person 915. Also, a plurality of observers may observe a plurality of observed persons via a network. FIGS. 16A and 16B show the case where the image recording apparatus 10 is used for a television conference. In this case, the image recording apparatus relating to the present embodiment can be used for a television conference. To be specific, image recording apparatuses are respectively provided for the observer side and observed persons side, and connected to each other via a network. The sound unit 40 provided in each image recording apparatus transmits sound to the other image recording apparatus, and the output section 50 provided in each image recording apparatus displays the image showing the other side on the display section.

The image-capturing unit 20 of the observer side includes therein the image-capturing sections 202 and 208, observer's point of sight measuring section 210 and observer's position measuring section 270. The image-capturing unit 20 of the observed person side includes therein the image-capturing section 204, observed person's position measuring section 212 and observed person's point of sight measuring section 214. Here, the coordinate systems of the image-capturing sections 202 to 208 may have a predetermined relation with each other. For example, the relation among the coordinate systems is calibrated before the observation is started via a network. As described earlier, the observer's point of sight measuring section 210 measures the points of sight of the observers 910 and 912 when the observers 910 and 912 observe the images of the observed persons 915 and 916 displayed on the display section included in the output section 50 of the observer side. The observed person's point of sight measuring section 214 measures the points of sight of the observed persons 915 and 916 when the observed persons 915 and 916 observe the images of the observers 910 and 912 displayed on the display section included in the output section 50 of the observed person side. The observer's position measuring section 270 measures the position of the observer 910 within the predetermined image-capturing target area. The observed person's position measuring section 212 measures the position of the observed person 915 within the predetermined image-capturing target area. Except for these operations, the above-mentioned constituents operate as described earlier.

Even when connected to each other via a network, the plurality of image recording apparatuses can accurately record the change in the facial expressions of the other side during conversation. In particular, when a speaker is making a speech to a plurality of persons, the image recording apparatuses can accurately record the facial expressions of a person to whom the speaker is paying attention during the speech.

Figure 17:
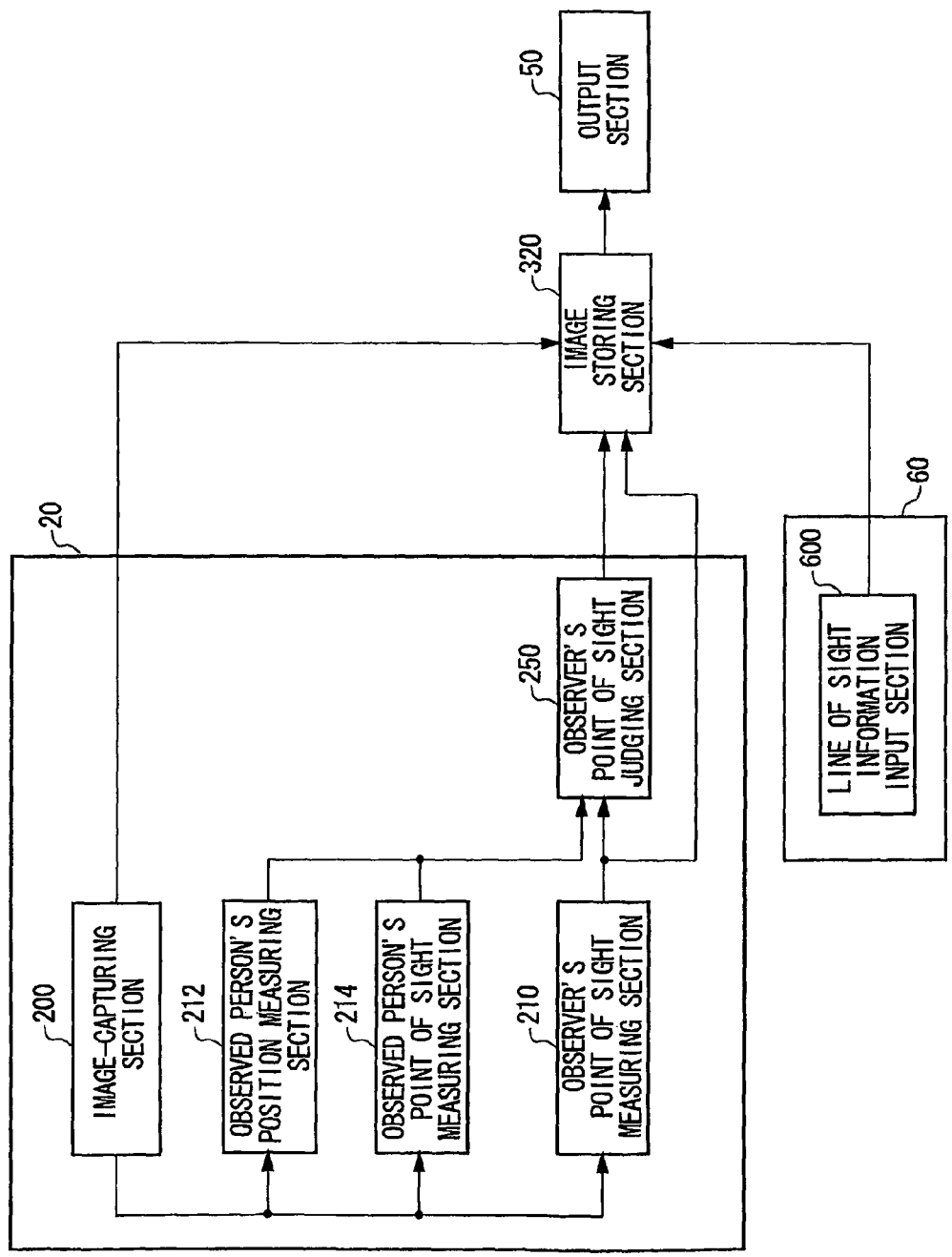
FIG. 17 illustrates exemplary functional configurations of the image-capturing unit 20 relating to a third embodiment and an input unit 60 relating to a second embodiment.

FIG. 17 shows exemplary functional configurations of the image-capturing unit 20 relating to a third embodiment and the input unit 60 relating to a second embodiment. The image-capturing unit 20 relating to the third embodiment includes therein the image-capturing section 200, observer's point of sight measuring section 210, observed person's position measuring section 212, observed person's point of sight measuring section 214 and observer's point of sight judging section 250. The input unit 60 relating to the second embodiment includes therein a line of sight information input section 600. These configurations aim to provide an image recording apparatus which makes it possible to, at a later time, easily retrieve an image of the observed person 915 to which the observer 910 pays attention. The image-capturing unit 20 and input unit 60 relating to the present embodiment may additionally include therein some or all of the functions and configurations of the units which together constitute the image recording apparatus 10 described with reference to FIGS. 1 to 11. The constituents assigned with the same reference numerals as in FIGS. 1 to 11 have substantially the same functions as the corresponding constituents in FIGS. 1 to 11, and therefore not explained in detail in the following.

As mentioned in the description of the image-capturing unit 20 relating to the first and second embodiments, when the image-capturing section 200 is an omnidirectional camera, the image-capturing section 200 may include the functions of the image-capturing sections 202 to 208. Alternatively, the image-capturing unit 20 may include, in place of the image-capturing section 200, the image-capturing section 202 for detecting the direction of the line of sight of the observer 910, the image-capturing section 208 for measuring the area within which the observer 910 is present, the image-capturing section 204 for detecting the direction of the line of sight of the observed person 915, and the image-capturing section 206 for measuring the area within which the observed person 915 is present.

The image-capturing section 200 captures the image of the observed person 915, and supplies the captured image of the observed person 915 to the image storing section 320. The image-capturing section 200 supplies the image used to measure the point of sight of the observed person 915 to the observed person's point of sight measuring section 214, and supplies the image used to measure the position at which the observed person 915 is present to the observed person's position measuring section 212. Also, the image-capturing section 200 supplies the image used to measure the point of sight of the observer 910 to the observer's point of sight measuring section 210. The observed person's position measuring section 212 measures the area, within the predetermined image-capturing target area of the image-capturing section 200, in which the observed person 915 is present. The observed person's position measuring section 212 measures the area corresponding to the eyes of the observed person 915. The observed person's position measuring section 212 supplies, to the observer's point of sight judging section 250, the information indicating the measured area within which the observed person 915 is present and the information indicating the measured area corresponding to the eyes of the observed person 915.

The observer's point of sight measuring section 210 measures the point of sight of the observer 910 when the image-capturing section 200 captures the image of the observed person 915. The observer's point of sight measuring section 210 also measures the method of how the observer 910 directs the line of sight towards the observed person 915 when the image-capturing section 200 captures the image of the observed person 915. The observer's point of sight measuring section 210 also measures the movement rate of the point of sight of the observer 910 when the image-capturing section 200 captures the image of the observed person 915. The observer's point of sight measuring section 210 supplies the measured information about the observer 910, such as the point of sight, the method of how to direct the line of sight, and the movement rate of the point of sight, to the observer's point of sight judging section 250 and the image storing section 320.

The observed person's point of sight measuring section 214 measures the point of sight of the observed person 915. The observed person's point of sight measuring section 214 may measure the point of sight of the observed person 915 in association with the time, to measure information indicating the trajectory of the point of sight of the observed person 915. The observed person's point of sight measuring section 214 supplies the information indicating the measured point of sight of the observed person 915 and the information indicating the trajectory of the point of sight, to the observer's point of sight judging section 250. The observer's point of sight judging section 250 judges whether the point of sight of the observer 910 measured by the observer's point of sight measuring section 210 is present within the area in which the observed person 915 is present which is measured by the observed person's position measuring section 212. The observer's point of sight judging section 250 also judges whether the point of sight of the observer 910 measured by the observer's point of sight measuring section 210 is present within the area corresponding to the face or hands of the observed person 915 which is measured by the observed person's position measuring section 212. Also, the observer's point of sight judging section 250 may judge whether the point of sight of the observer 910 measured by the observer's point of sight measuring section 210 is present within the area corresponding to the eyes of the observed person 915 which is measured by the observed person's position measuring section 212. Furthermore, the observer's point of sight judging section 250 judges whether the lines of sight of the observer 910 and observed person 915 coincide with each other. The observer's point of sight judging section 250 supplies the result of the judgment to the image storing section 320.

The image storing section 320 stores thereon the image captured by the image-capturing section 200 in association with the information indicating the point of sight of the observer 910, the method of how the observer 910 directs the line of sight towards the observed person 915, the movement rate of the point of sight of the observer 910, and the information indicating the result of the judgment made by the observer's point of sight judging section 250. The image storing section 320 supplies the stored image to the output section 50 under the control of the line of sight information input section 600. Here, the line of sight information input section 600 enables the user 917 to input information indicating the point of sight of the observer 910. Specifically speaking, the line of sight information input section 600 enables the user 917 to input information indicating that the point of sight of the observer 910 is present within the area in which the observed person 915 is present or information indicating that the point of sight of the observer 910 is present within the area corresponding to the face or hands of the observed person 915. Also, the line of sight information input section 600 may enable the user 917 to input information indicating that the point of sight of the observer 910 is present within the area corresponding to the eyes of the observed person 915. Here, the area corresponding to the face, the area corresponding to the hands, and the area corresponding to the eyes respectively may be regions of predetermined sizes including the face, hands and eyes and the surrounding areas thereof. For example, the area corresponding to the eyes is a region defined by a circle that has a center at the black part of at least one of the left and right eyes and a radius of 1 cm. Alternatively, the area corresponding to the eyes may be a region which includes both of the eyes and is defined by a rectangle or ellipse that has the long side in the horizontal direction of the face. The line of sight information input section 600 may enable the user 917 to input information indicating the method of how the observer 910 directs the line of sight towards the observed person 915, information indicating the movement rate of the point of sight, and information indicating that the lines of sight of the observer 910 and observed person 915 coincide with each other. For example, when the user 917 desires to look at the image of the observed person 915 which is captured when the observer 910 pays attention to the eyes of the observed person 915, the user 917 inputs, into the line of sight information input section 600, information indicating that the point of sight of the observer 910 is present at the eyes of the observed person 915. The line of sight information input section 600 supplies the information input by the user 917 to the output section 50.

The output section 50 outputs the image of the observed person 915 which is stored on the image storing section 320 in association with the information indicating the point of sight of the observer 910 which is input through the line of sight information input section 600. Specifically speaking, the output section 50 receives the information indicating the point of sight of the observer 910 input through the line of sight information input section 600, and extracts and outputs the image which is stored on the image storing section 320 in association with the information coinciding with the information received form the line of sight information input section 600.

The output section 50 may include therein an advising section. The advising section advises that the observer 910 should ask a different question to the observed person 915, based on the change in the point of sight of the observed person 915. Specifically speaking, the advising section judges whether the observed person 915 diverts the eyes from the observer 910, based on the trajectory of the point of sight of the observed person 915. When judging that the observed person 915 diverts the eyes from the observer 910, the advising section displays on the output section 50 a character string advising that the observer 910 should ask a different question to the observed person 915. Here, the output section 50 may advise the observer 910 to ask a different question by way of sound.

According to the present embodiment, the image recording apparatus 10 can store thereon the image of the observed person 915 in association with the information obtained when the observer 910 observes the observed person 915, such as the point of sight of the observer 910, the method of how the observer 910 directs the line of sight towards the observed person 915, the movement rate of the point of sight, and information indicating the lines of sight of the observer 910 and observed person 915 coincide with each other. Therefore, the image recording apparatus 10 can reproduce how the observer 910 observes the observed person 915, at a later time than the actual observation of the observed person 915 by the observer 910. In addition, the image recording apparatus 10 makes it possible to easily retrieve the image of the observed person 915 to which the observer 910 pays attention.

According to the present embodiment, the image storing section 320 may store thereon the image of the observed person 915 captured by the image-capturing section 200 further in association with information indicating the point of sight of the observed person 915 which is measured by the observed person's point of sight measuring section 214. In this case, the line of sight information input section 600 further enables the user to input information indicating the point of sight of the observed person 915. The output section 50 outputs the image of the observed person or observer which is stored on the image storing section 320, based on the information indicating the point of sight of the observed person 915 and the information indicating the point of sight of the observer 910 which are input through the line of sight information input section 600. With this configuration, the image recording apparatus 10 relating to the present embodiment makes it possible to reproduce the image of the observed person at a later time than the observation, based on the combination of the points of the sight of the observer and observed person.

FIGS. 18 and 19 are used to illustrate the operation performed by the observer's point of sight judging section 250. FIG. 20 shows one example of the data stored on the image storing section 320. FIG. 18A shows a plurality of predetermined regions 850 to 858 in the image of the observed person 915, and FIG. 18B shows a plurality of predetermined regions 860 to 868 in the image of the observer 910. The regions 850, 852 and 854 are, for example, the areas corresponding to the face, eyes and mouth of the observed person 915. The regions 856 and 858 are the areas corresponding to the hands (right and left hands) of the observed person 915. The regions 860 and 862 are the areas corresponding to the eyes (left and right eyes) of the observer 910, and the region 864 is the area corresponding to the mouth of the observer 910. The regions 866, 868 and 870 are respectively right, left and upper regions, with respect to the observer 910, which do not include the observer 910.

The observer's point of sight judging section 250 judges whether the point of sight of the observer 910 is present in any one of the regions 850 to 858 while the observer 910 is observing the observed person 915. Also, the observer's point of sight judging section 250 judges whether the point of sight of the observed person 915 is present in any one of the regions 860 to 868. In the present embodiment, the observer's point of sight judging section 250 receives pieces of coordinate data indicating the points of sight from the observer's point of sight measuring section 210 and observed person's point of sight measuring section 214, as pieces of information indicating the points of sight of the observer 910 and observed person 915, and judges whether the received points of sight are included in any of the predetermined regions, as shown in FIG. 19. The image storing section 320 stores thereon the result of the judgment in accordance with the data structure shown in FIG. 20, for example. According to the example shown in FIG. 20, the image storing section 320 stores thereon the coordinate data indicating the point of sight of the observer and the region in the image of the observed person 915 which includes the point of sight of the observer, in association with the image of the observed person the observer looks at. The image storing section 320 also stores thereon the coordinate data indicating the point of sight of the observed person and the region in the image of the observer 910 which includes the point of sight of the observed person, in association with the image of the observed person.

For example, the line of sight information input section 600 enables the user to input, as the information indicating the point of sight of the observer 910, the name of the region to which the observer 910 pays attention, and, as the information indicating the point of sight of the observed person 915, the name of the region to which the observed person 915 pays attention to. It is assumed that the observer is a medical doctor, for example. Here, if the medical doctor desires to retrieve an image which is captured when the medical doctor pays attention to the area including the mouth of a patient who is the observed person, the medical doctor inputs a keyword of "mouth" as the information indicating the point of sight of the observer 910. In this case, the output section 50 outputs a moving image 1 which is captured when the medical doctor pays attention to the mouth and surrounding area of the patient. Also, based on the information indicating the point of sight of the observer which is input through the line of sight information input section 600, the output section 50 may extract and output the predetermined region corresponding to the input point of sight from the image of the observed person 915 stored on the image storing section 320. In this case, the output section 50 extracts and outputs, as the predetermined region corresponding to the input point of sight, a predetermined region in the image of the observed person which is stored in association with the information indicating the point of sight of the observer 910. For example, when a keyword "right eye" is input as the information indicating the point of sight of the observer, the image showing the region 852 corresponding to the right eye of the patient is extracted from the moving image 1 which is stored in association with the keyword "right eye", and the extracted image is output.

According to the present embodiment, the sound recording section 400 in the sound unit 40 records sound information of the observer 910 and observed person 915. Here, the image storing section 320 further stores thereon the sound information of the observer 910 which is recorded by the sound recording section 400 in association with the image of the observed person 915 which is captured by the image-capturing section 200. The line of sight information input section 600 enables the user to further input the information indicating the sound information of the observer 910. The output section 50 outputs the image of the observed person 915 which is stored on the image storing section 320, based on the input sound information of the observed person 915.

Note that the sound information is, for example, conversation exchanged when the observer 910 observes the observed person 915. The line of sight information input section 600 stores, as the sound information, sound data and information regarding the contents of the sound data, in association with the image of the observed person 915. Here, the line of sight information input section 600 may store a keyword or sentence, as the information regarding the contents of the sound data. The line of sight information input section 600 enables the user to input a keyword relating to the contents of the observation performed by the observer 910 on the observed person 915, as the information indicating the sound information of the observer 910. In this way, the image recording apparatus relating to the present embodiment can reproduce how the observer 910 observes the observed person 915 at a later time than the observation. Also, the image recording apparatus relating to the present embodiment can easily retrieve the image of the observed person 915 based on the information indicating the area to which the observer 910 pays attention to during the observation. Furthermore, the image recording apparatus relating to the present embodiment can retrieve a desired image based on the information regarding the conversation exchanged between the observer and observed person.

Here, the image-capturing section 200 relating to the present embodiment may capture an image of a plurality of observed persons. In this case, an image is captured which indicates the area, within the predetermined image-capturing target area of the image-capturing section 200, in which the plurality of observed persons 915 are present, and the observed person's position measuring section 212 supplies the information indicating the area in which the plurality of observed persons 915 are present, to the observer's point of sight judging section 250. The observer's point of sight judging section 250 identifies an area corresponding to one of the observed persons in which the point of sight of the observer measured by the observer's point of sight measuring section 210 is present. Here, the observer's point of sight judging section 250 may judge whether the point of sight of the observer 910 is present in the area corresponding to the face, hands or eyes of the identified observed person 915 which is measured by the observed person's position measuring section 212. The image storing section 320 stores thereon the image of the observed person who is identified, by the observer's point of sight judging section 250, so as to correspond to the point of sight of the observer, in association with the information indicating the point of sight of the observer. The line of sight information input section 600 enables the user to input information indicating the point of sight of the observer, and the output section 50 outputs the image of the observed person which is stored on the image storing section 320 in association with the input information indicating the point of sight of the observer.

The image recording apparatus 10 including therein the image-capturing unit 20 relating to the present embodiment may be used when a plurality of observers observe a plurality of observed persons via a network. For example, the image recording apparatus 10 may be used for a television conference. In this case, in association with the point of sight of a speaker on the observer side and the point of sight of the audience who observes the speaker on the display section on the observed person side, the image storing section 320 may store thereon the image of the speaker and the image of the audience listening to the speaker. Also, the image storing section 320 may store thereon the images of the speaker and audience in association with the contents of the speech made by the speaker. The line of sight information input section 600 enables the user to input information indicating the point of sight of the speaker, the point sight of the audience, and/or contents of the speech made by the speaker. The output section 50 outputs the images of the speaker and audience which are stored in association with the input information indicating the point of sight of the speaker, the point of sight of the audience, and/or contents of the speech made by the speaker. In this way, the image recording apparatus 10 relating to the present embodiment makes it possible to retrieve an image by using the points of sight of a speaker and audience as a keyword after the television conference.

Figure 21:
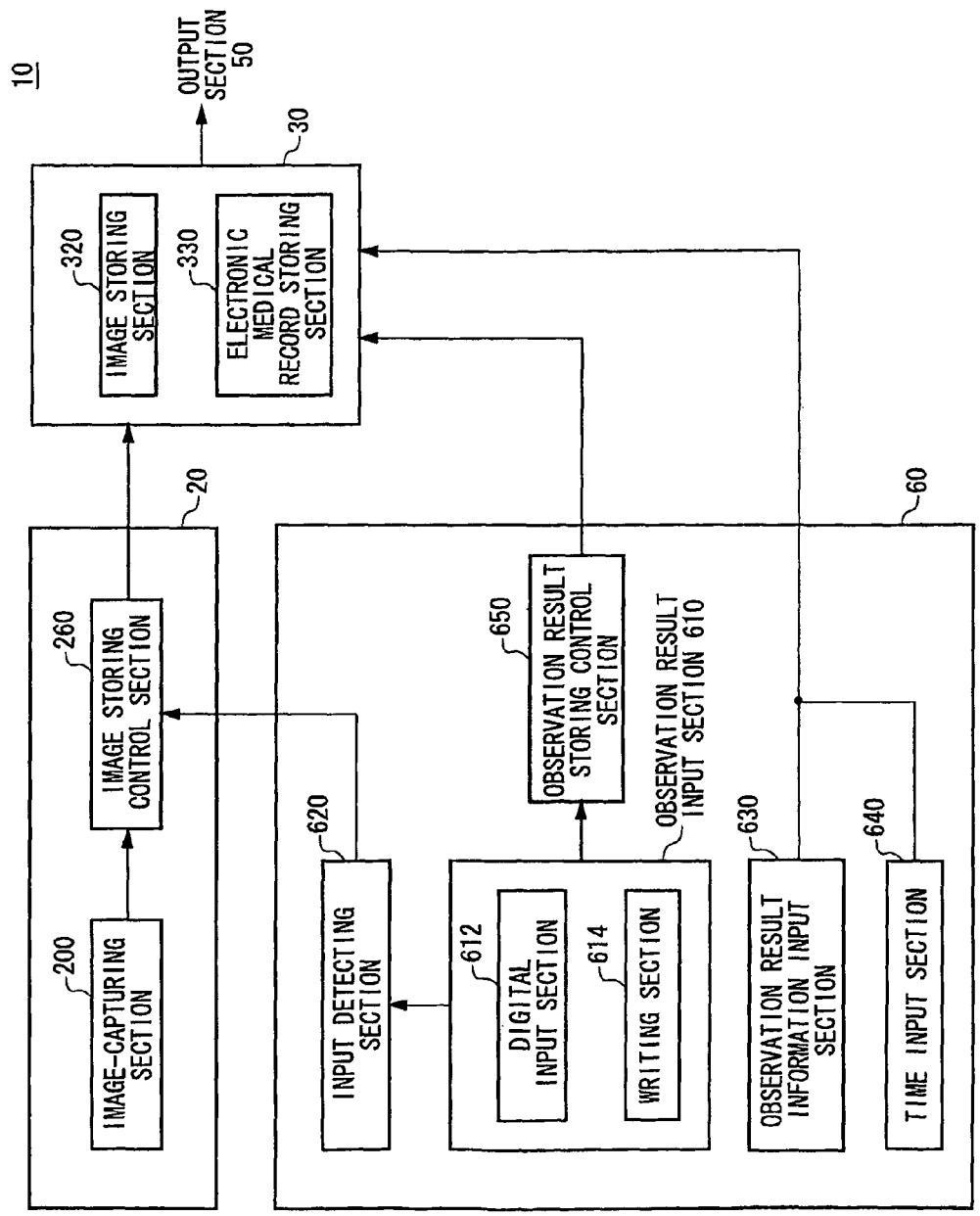
FIG. 21 illustrates exemplary functional configurations of the image-capturing unit 20 relating to a fourth embodiment and input unit 60 relating to a third embodiment in the image recording apparatus 10.

FIG. 21 illustrates exemplary functional configurations of the image-capturing unit 20 relating to a fourth embodiment and the input unit 60 relating to a third embodiment included in the image recording apparatus 10. The image-capturing unit 20 includes therein the image-capturing section 200 and image storing control section 260. The storing unit 30 includes therein the image storing section 320 and an electronic medical record storing section 330. The input unit 60 includes therein an observation result input section 610, an input detecting section 620, an observation result information input section 630, a time input section 640, and an observation result storing control section 650. Here, the observation result input section 610 includes therein the digital input section 612 and writing section 614. With the above-described configurations, the image recording apparatus 10 relating to the present embodiment aims to make it possible to appropriately reproduce the facial expressions of the observed person 915 at a later time, even if the observer 910 can not see the facial expressions of the observed person 915 while inputting the observation result into an electronic medical record or the like. Here, the image recording apparatus 10 relating to the present embodiment may further include some or all of the functions and configurations of the units which together constitute the image recording apparatus 10 described with reference to FIGS. 1 to 11. The constituents assigned with the same reference numerals as in FIGS. 1 to 11 have substantially the same functions as the corresponding constituents in FIGS. 1 to 11, and therefore not explained in detail in the following.

The image-capturing section 200 captures an image of the observed person 915, and supplies the captured image of the observed person 915 to the image storing section 320. The image-capturing section 200 also supplies the image to the image storing control section 260. The electronic medical record storing section 330 stores thereon en electronic medical record to which a result of the observation on the observed person 915 is input. Specifically speaking, the observation result input section 610 is used to input the result of the observation done by the observer 910. The observation result input section 610 supplies information indicating the input of the observation result, to the input detecting section 620. The observation result input section 610 then supplies the observation result which is input by the observer 910 to the observation result storing control section 650. The observation result storing control section 650 stores, as an electronic medical record, the observation result received from the observation result input section 610 onto the electronic medical record storing section 330. To be more specific, the digital input section 612 included in the observation result input section 610 is used to input the result of the observation done by the observer 910 into the electronic medical record. The digital input section 612 is, for example, a keyboard, a mouse, a touch panel or the like. The digital input section 612 supplies, to the input detecting section 620, the information indicating that the observer 910 is inputting the observation result into the electronic medical record.

The writing section 614 included in the observation result input section 610 is used by the observer 910 to write the observation result into a medical record. The writing section 614 may include a case 615, a pressing detecting section 616, a pen tip 617, and a detected result transmitting section 618. The pressing detecting section 616 detects a change in pressure which is caused by application of pressure to the pen tip 617 when the observer 910 writes the observation result. The pressing detecting section 616 supplies information indicating the detected change in pressure to the detected result transmitting section 618. The detected result transmitting section 618 supplies the information indicating the change in pressure to the input detecting section 620. The detected result transmitting section 618 may supply the information indicating the change in pressure to the input detecting section 620 by way of wired or wireless communication.

The input detecting section 620 detects that the digital input section 612 is used to input the result of the observation done by the observer 910 into the electronic medical record stored on the electronic medical record storing section 330. Also, the input detecting section 620 detects that the writing section 614 is used to write the result of the observation done by the observer 910 into the medical record. Note that the writing section 614 may be used to write the observation result into a paper medical record. The writing section 614 may be a pen or the like for a digital white board. When the writing section 614 is a pen for a digital white board, the writing section 614 can be used to write the observation result into the electronic medical record via the digital white board. In this case, the observation result written by using the writing section 614 is supplied to the observation result storing control section 650.

The image storing control section 260 stores the image of the observed person 915 captured by the image-capturing section 200 onto the image storing section 320, when the input detecting section 620 detects that the result of the observation done by the observer 910 is input. To be specific, the image storing control section 260 obtains the image of the observed person 915 captured by the image-capturing section 200, when receiving, from the input detecting section 620, the information indicating that the result of the observation done by the observer 910 is input by using the observation result input section 610. The image storing control section 260 then stores the obtained image of the observed person 915 onto the image storing section 320. Alternatively, the image storing control section 260 stores, onto the image storing section 320, images of the observed person 915 which are captured by the image-capturing section 200 for a predetermined period of time starting from a time that precedes, by a predetermined time period, the time at which the input detecting section 620 detects that the result of the observation done by the observer 910 is input. The image storing section 320 stores the image captured by the image-capturing section 200 in association with information indicating the result of the observation done by the observer 910 which is input by means of the observation result input section 610 and the time at which the observer 910 inputs the observation result. Here, the information indicating the result of the observation may include the name of a disease, a symptom, progression of the symptom, and improvement of the symptom. The image storing section 320 supplies the image stored thereon to the output section 50 under the control of the observation result information input section 630 and time input section 640.

The observation result information input section 630 enables the user 917 to input information indicating a result of observation done by the observer 910. Here, the user 917 may be the observer 910, a different observer than the observer 910, or the observed person 915, for example. When the user 917 desires to know what facial expression of the observer person 915 helps the observer 910 judge the symptom of the observed person 915, for example, the user 917 inputs, as the information indicating the observation result, the name of the symptom observed by the observer 910 into the observation result information input section 630. The observation result information input section 630 causes the output section 50 to output an image of the observed person 915 which is stored on the image storing section 320 in association with the name of the symptom input by the user 917. The time input section 640 enables the user 917 to input a time. For example, when the user 917 desires to look at a previous image of the observed person 915, the user 917 inputs a time corresponding to a desired image through the time input section 640. The time input section 640 causes the output section 50 to output an image of the observed person 915 which is stored on the image storing section 320 in association with the time input by the user 917.

The output section 50 outputs an image of the observed person 915 which is stored on the image storing section 320 in association with the information indicating the result of the observation done by the observer 910 which is input through the observation result information input section 630. Also, the output section 50 outputs an image of the observed person 915 which is stored on the image storing section 320 in association with the time input through the time input section 640. The output section 50 may be a display apparatus such as a display screen. The output section 50 may display, side by side, images of the observed person 915 in the chronological order. Alternatively, the output section 50 may display, one at a time, images of the observed person 915 in the chronological order at predetermined time intervals.

The output section 50 may be provided in a head-mounted display. When the output section 50 is a head-mounted display, the observer 910 can look at, by way of the output section 50 provided in the head-mounted display, the images of the observed person 915 even while, for example, inputting the observation result into an electronic or paper medical record. In this case, the output section 50 may display the images of the observed person 915 at an area which does not make it difficult for the observer 910 to input the observation result into the electronic medical record or the like. For example, the head-mounted display may include therein an observer's line of sight detecting section for detecting the line of sight of the observer 910. The output section 50 may display the images in a different area which is selected depending on the line of sight of the observer 910 which is detected by the observer's line of sight detecting section. The output section 50 may not be required to display the images of the observed person 915 on the head-mounted display when the observer 910 faces the observed person 915. Here, the image-capturing section 200 may be provided at the entrance and exit of a clinic, for example, so as to capture images of the facial expressions exhibited by the observed person 915 when the observed person 915 walks into and out the clinic.

While the observer 910 is inputting or writing the result of observing the observed person 915 into an electronic or paper medical record, the image recording apparatus 10 relating to the present embodiment detects the timing of inputting and writing by the observer 910 and automatically captures an image of the observed person 915 at the detected timing. In this way, it is made possible to reproduce, at a later time, the facial expressions of the observed person 915 which are not actually observed by the observer 910 because those facial expressions are exhibited while the observer 910 inputs the observation result into an electronic medical record or the like.

Also the image recording apparatus 10 relating to the present embodiment can obtain images of the observed person 915 which are captured for a predetermined period of time starting from a time that precedes, by a predetermined time period, the time at which the observer 910 inputs the result of observing the observed person 915 into an electronic medical record, so as to enable the observer 910 to look at the missed images of the observed person 915 in the chronological order. In this way, the observer 910 can be reliably prevented from missing an image showing the observed person 915 which may have an influence on the observation result of the observed person 915.

Figure 22:
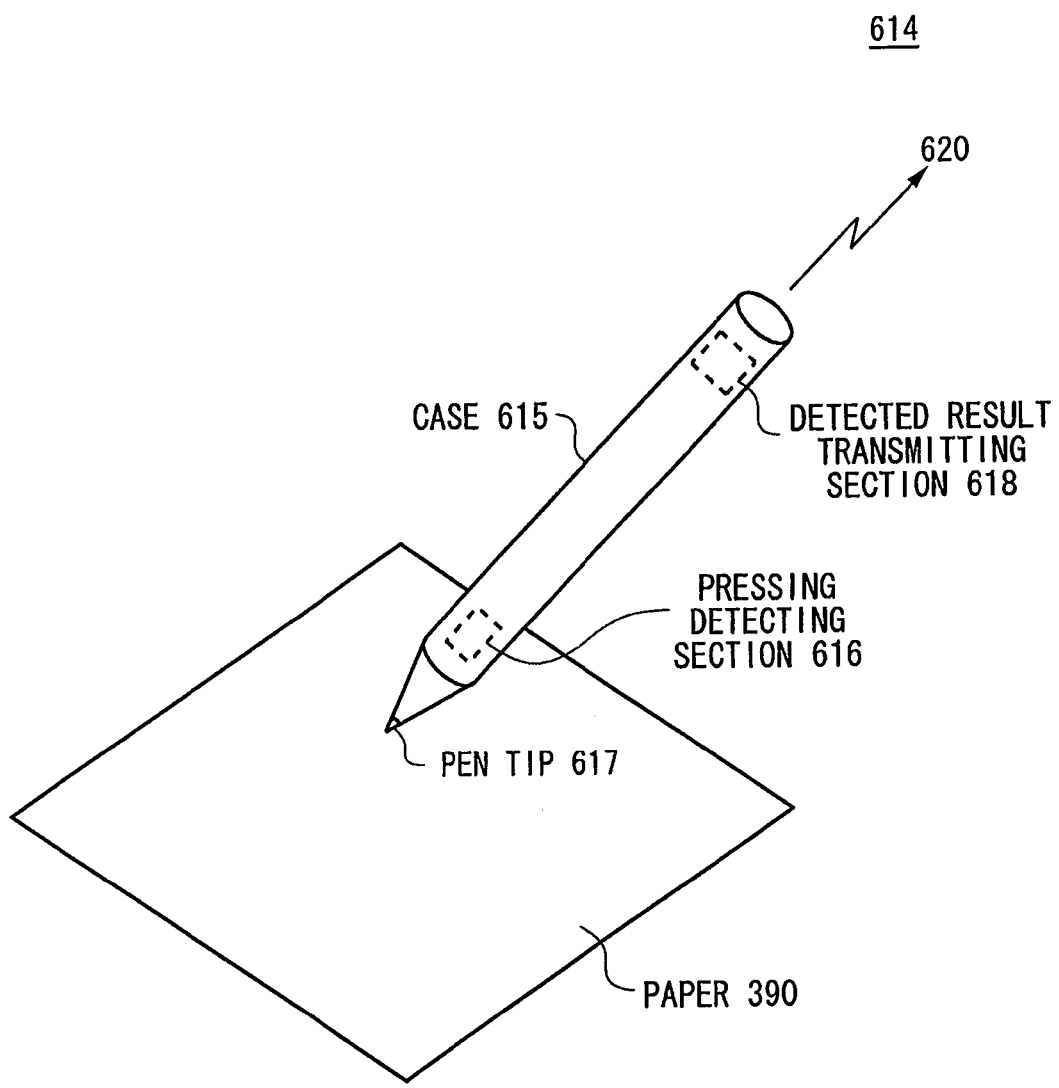
FIG. 22 illustrates a writing section 614.

FIG. 22 illustrates one example of the writing section 614 relating to the present embodiment. The writing section 614 includes the case 615, pressing detecting section 616, pen tip 617, and detected result transmitting section 618. The pressing detecting section 616 detects pressure applied to the pen tip 617 when the pressure is applied to the pen tip 617. For example, the pressing detecting section 616 detects pressure applied to the pen tip 617 when the observer 910 writes a letter or the like on paper 390. The pressing detecting section 616 supplies information indicating the detected pressure to the detected result transmitting section 618. The detected result transmitting section 618 supplies the information indicating the pressure detected by the pressing detecting section 616 to the input detecting section 620. The detected result transmitting section 618 and input detecting section 620 may be coupled to each other by wired or wireless connection.

FIG. 23 illustrates exemplary data stored on the image storing section 320 relating to the present embodiment. According to the example shown in FIG. 23, the image storing section 320 stores thereon a moving image which is captured by the image-capturing section 200 for a period of time starting at a time that precedes, by three minutes, the time at which the observation result is input and ending at the time at which the observation result is input. Note that the sound recording section 400 included in the sound unit 40 records sound information of the observer 910 while the image-capturing section 200 captures an image of the observed person 915. Here, the sound information is conversation exchanged when the observer 910 observes the observed person 915, for example. The line of sight information input section 600 stores, as the sound information, sound data and information regarding the contents of the sound data in association with an image of the observed person 915. In this case, the observation result input section 610 may store, as the information regarding the contents of the sound data, a keyword or sentence. The image storing section 320 stores thereon the images of the observed person 915 which are captured by the image-capturing section 200 further in association with the sound information of the observer 910 which is recorded by the sound recording section 400. The observation result input section 610 may enable the user to input a keyword relating to the contents of the observation on the observed person 915 by the observer 910, and the output section 50 may output the image of the observed person 915 which is stored on the image storing section 320 in association with the sound information of the observer 910.

Figure 24:
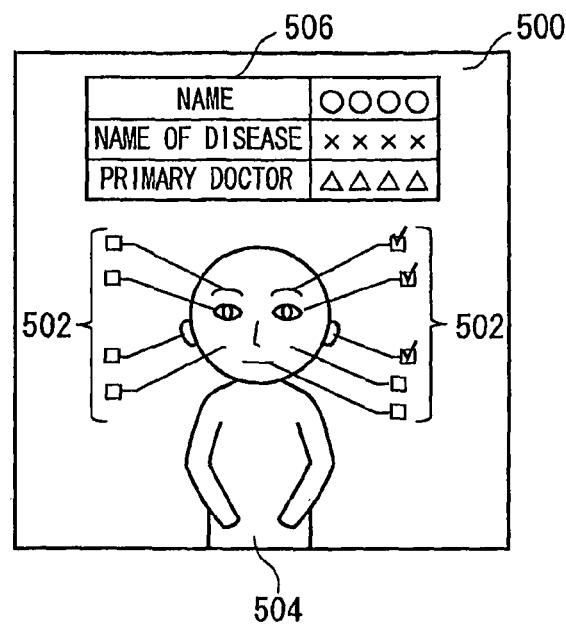
FIG. 24 is used to illustrate an electronic medical record 500.
Figures 25A, 25B:
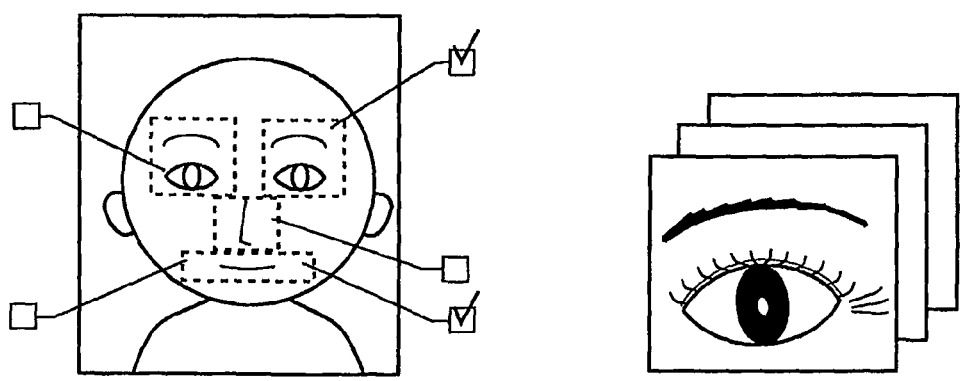
FIGS. 25A and 25B are used to illustrate the electronic medical record 500.

FIGS. 24, 25A and 25B are used to illustrate an electronic medical record 500 relating to the present embodiment. The output section 50 displays, on a display section included in the output section 50, an electronic medical record stored on the electronic medical record storing section 330. FIG. 24 illustrates an exemplary user interface for the electronic medical record 500. The electronic medical record storing section 330 relating to the present embodiment stores thereon the observation result by way of an image 504 which schematically illustrates a patient body. The image 504 schematically illustrating the patient body may be an image showing part of a human body such as an upper body, a lower body, limbs, and a face, or an image showing the entire human body.

The electronic medical record storing section 330 stores information indicating whether a disease is found in association with predetermined areas in the image 504 schematically illustrating a human body. In detail, the electronic medical record 500 has checkboxes respectively corresponding to the predetermined areas of the image 504 schematically illustrating a human body. Here, the checkboxes are checked or cleared depending of whether a disease is found by way of the digital input section 612. The electronic medical record 500 shown in FIG. 24 has a plurality of checkboxes 502 respectively corresponding to different areas of the face of the patient. With this configuration, the observer 910 can quickly complete inputting the result of the observation into the electronic medical record.

Here, the image 504 schematically illustrating a patient may be replaced by an actual image of the observed person 915 which is captured by the image-capturing section 200. If such is the case, the electronic medical record 500 has checkboxes respectively corresponding to predetermined areas of the actual image of the observed person 915 which is captured by the image-capturing section 200. Alternatively, the electronic medical record 500 may have checkboxes corresponding to at least a partial region of the image of the observed person 915 which is captured by the image-capturing section 200. Here, the partial region of the image of the observed person 915 may be a region indicating a predetermined area of a patient body, such as the face, eyes, mouth, and nose of the observed person 915. FIGS. 25A and 25B are used to illustrate exemplary electronic medical record which uses the actual image of the observed person 915.

When one or more of the checkboxes are checked in accordance with the input through the digital input section 612, the image storing section 320 stores thereon the image of the observed person 915 which is associated with the checkboxes, together with the information indicating the observation result. In this way, the image storing section 320 relating to the present embodiment stores at least a partial region of the image of the observed person 915 which is captured by the image-capturing section 200, in association with the information indicating the observation result, based on the input by way of the digital input section 612. Here, when the observation result is input by checking the checkboxes, the image storing section 320 stores thereon some of the images of the observed person 915 which are captured by the image-capturing section 200 during a predetermined period of time starting at a time that precedes, by a predetermined time period, the time at which the input detecting section 620 detects the input of the observation result. The output section 50 may display an image obtained by enlarging at least part of the image of the observed person 915 which is stored on the image storing section 320. Alternatively, the output section 50 may display at least part of each of the images of the observed person 915 which are stored on the image storing section 320, in the chronological order within the electronic medical record.

As described above, the electronic medical record 500 relating to the present embodiment uses the actual image of the observed person 915, thereby enabling a change in symptoms to be accurately known. Also, since the electronic medical record 500 uses part of the image of the observed person 915, the privacy of the observed person 915 can be protected.

Figure 26:
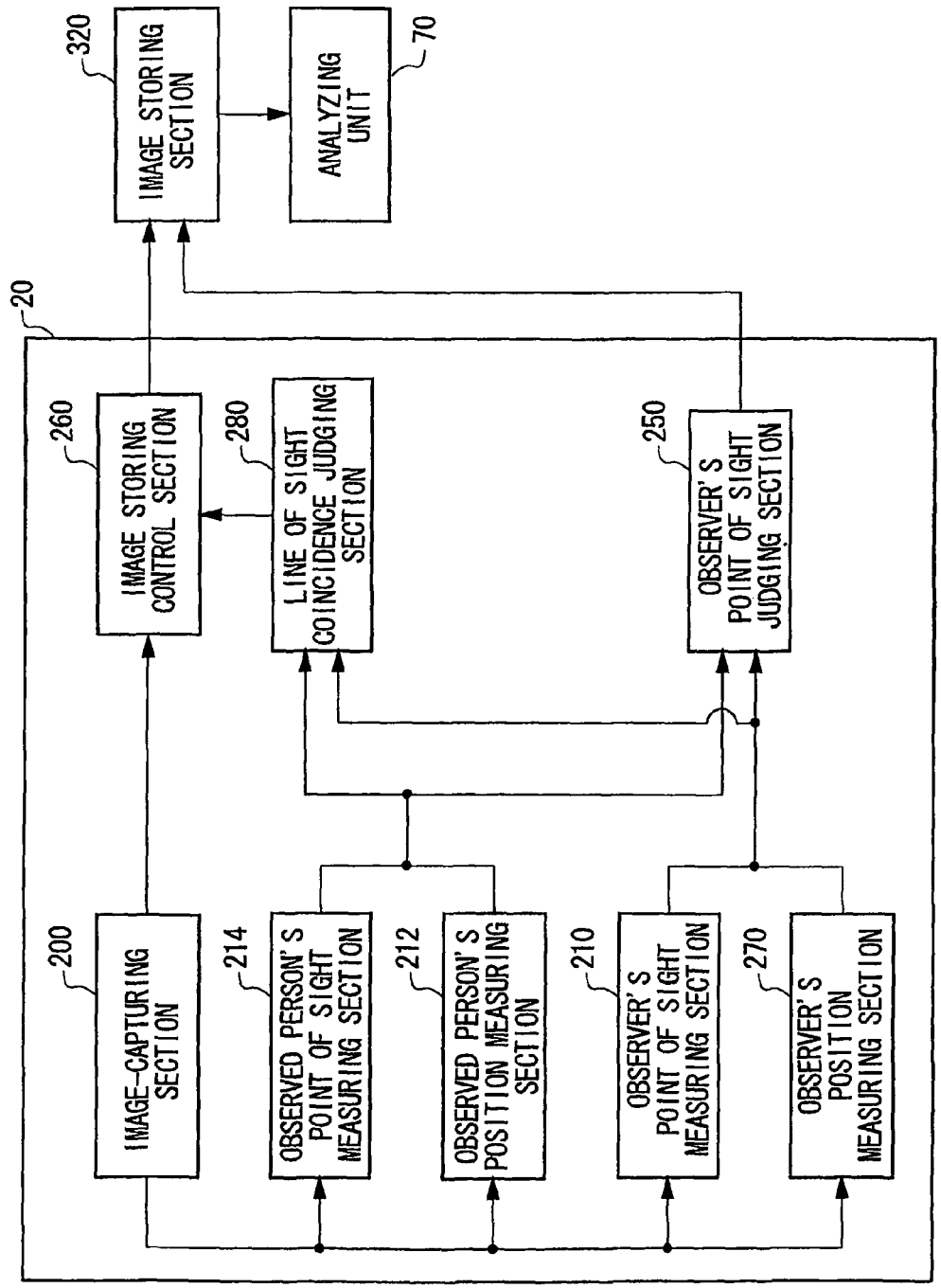
FIG. 26 illustrates an exemplary functional configuration of the image-capturing unit 20 relating to a fifth embodiment.

FIG. 26 illustrates an exemplary functional configuration of the image-capturing unit 20 relating to a fifth embodiment. The image-capturing unit 20 includes therein the image-capturing section 200, observer's point of sight measuring section 210, observed person's position measuring section 212, observed person's point of sight measuring section 214, observer's point of sight judging section 250, image storing control section 260, observer's position measuring section 270, and a line of sight coincidence judging section 280. The following description is made based on an assumption that the image recording apparatus 10 relating to the present embodiment is used in the medical field. The image recording apparatus 10 relating to the present embodiment quantifies the physical status of the observed person 915 when the observer 910 observes the observed person 915, and records thereon the quantified physical status. Based on this, the image recording apparatus 10 relating to the present embodiment aims to output information indicating a disease candidate which a person under observation may possibly suffer from, when the person under observation is newly observed. Also, the image recording apparatus 10 aims to facilitate observation by generating an image corresponding to a disease.

Here, when the image-capturing section 200 is an omnidirectional camera, for example, the image-capturing section 200 may include functions of the image-capturing section 202 for detecting the point of sight of the observer 910, the image-capturing section 208 for measuring the area in which the observer 910 is present, the image-capturing section 204 for detecting the point of sight of the observed person 915, and the image-capturing section 206 for measuring the area in which the observed person 915 is present. Alternatively, the image-capturing unit 20 may include therein, in place of the image-capturing section 200, the image-capturing section 202 for detecting the direction of the line of sight of the observer 910, the image-capturing section 208 for measuring the area in which the observer 910 is present, the image-capturing section 204 for detecting the direction of the line of sight of the observed person 915, and the image-capturing section 206 for measuring the area in which the observed person 915 is present.

Figure 27:
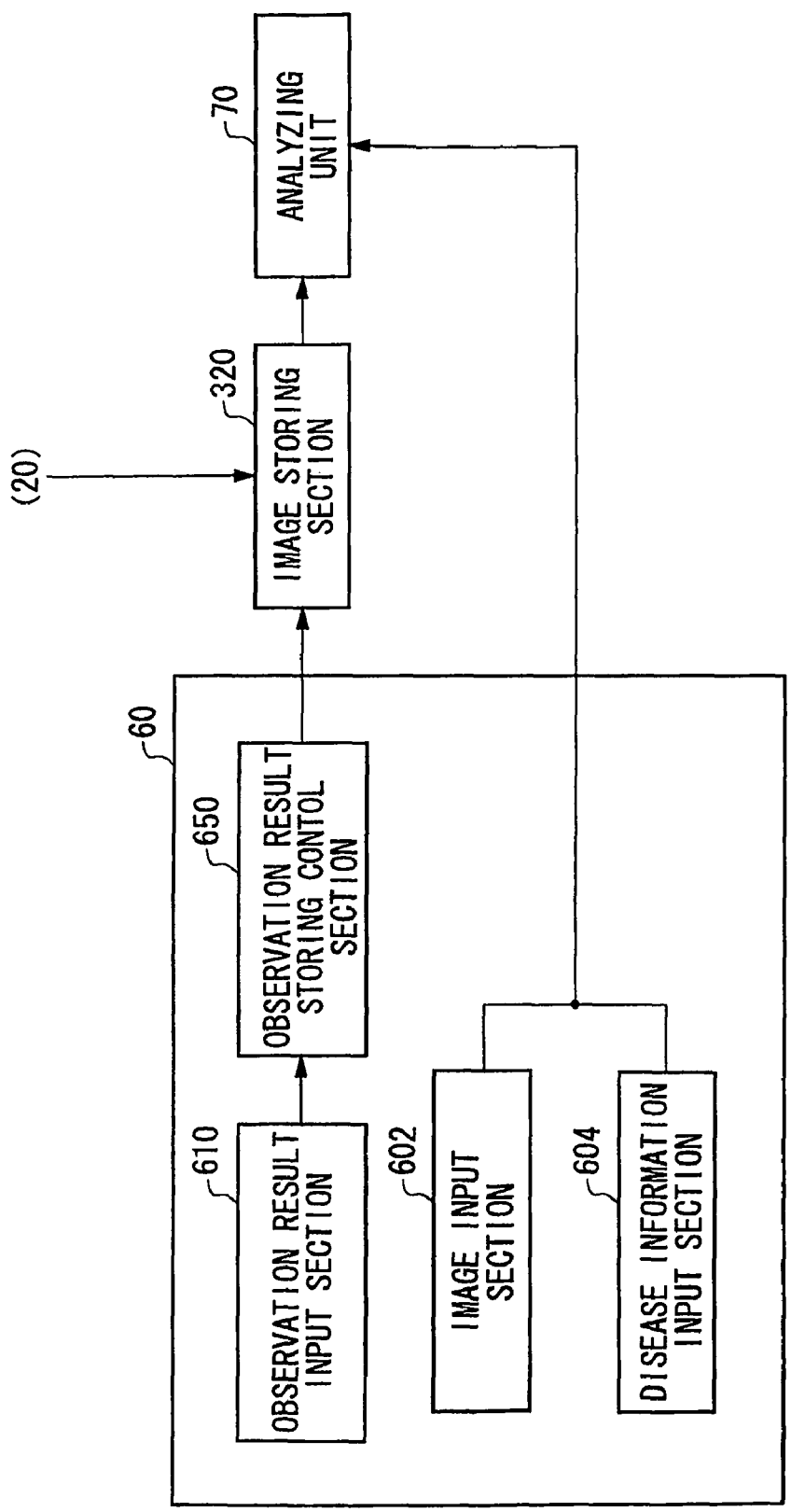
FIG. 27 illustrates an exemplary functional configuration of the input unit 60 relating to a fourth embodiment.
Figure 28:
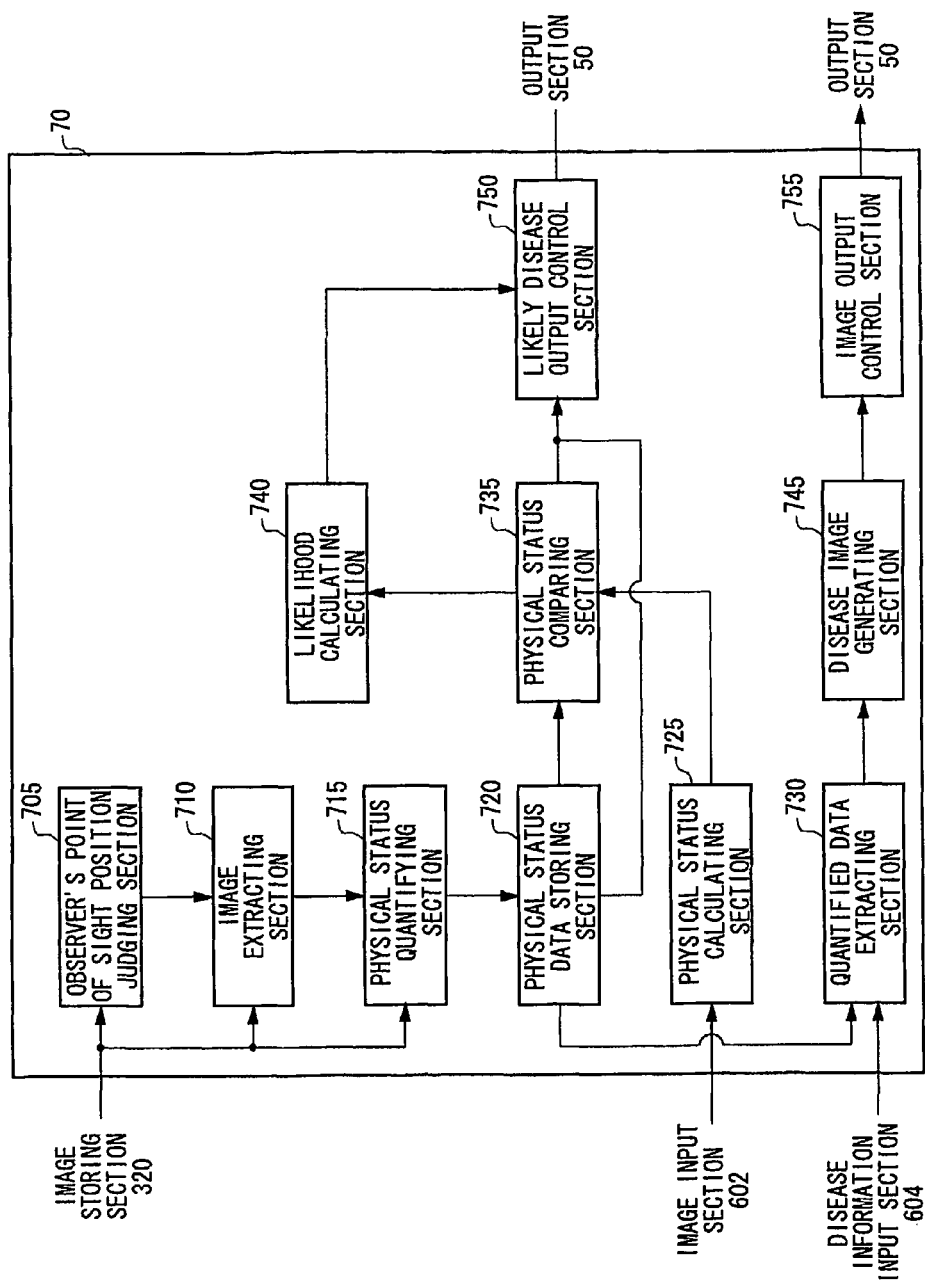
FIG. 28 illustrates an exemplary functional configuration of an analyzing unit 70 relating to a second embodiment.

FIG. 27 illustrates an exemplary functional configuration of the input unit 60 relating to a fourth embodiment. The input unit 60 relating to the present embodiment includes therein an image input section 602, a disease information input section 604, the observation result input section 610, and the observation result storing control section 650. FIG. 28 illustrates an exemplary functional configuration of the analyzing unit 70 relating to a second embodiment. The analyzing unit 70 includes therein an observer's point of sight position judging section 705, an image extracting section 710, a physical status quantifying section 715, a physical status data storing section 720, a physical status calculating section 725, a quantified data extracting section 730, a physical status comparing section 735, a likelihood calculating section 740, a disease image generating section 745, a likely disease output control section 750, and an image output control section 755. Here, the image recording apparatus 10 relating to the present embodiment may further include some or all of the functions and configurations of the units which together constitute the image recording apparatus 10 described with reference to FIGS. 1 to 11. The constituents assigned with the same reference numerals as in FIGS. 1 to 11 have substantially the same functions as the corresponding constituents in FIGS. 1 to 11, and therefore not explained in detail in the following.

The image-capturing section 200 captures an image of the observed person 915. The image-capturing section 200 may capture a moving image of the observed person 915. The image-capturing section 200 supplies the captured image to the image storing control section 260 under control of the image storing control section 260. Also, the image-capturing section 200 supplies the image used to measure the point of sight of the observed person 915 to the observed person's point of sight measuring section 214, and the image used to measure the position at which the observed person 915 is present to the observed person's position measuring section 212. In addition, the image-capturing section 200 supplies the image used to measure the point of sight of the observer 910 to the observer's point of sight measuring section 210, and the image used to measure the position at which the observer 910 is present to the observer's position measuring section 270. The observer's point of sight measuring section 210 measures the point of sight of the observer 910 when the image-capturing section 200 captures the image of the observed person 915. The observer's point of sight measuring section 210 supplies the measured point of sight to the observer's point of sight judging section 250 and line of sight coincidence judging section 280.

The observed person's point of sight measuring section 214 measures the point of sight of the observed person 915 when the image-capturing section 200 captures the image of the observed person 915. The observed person's point of sight measuring section 214 supplies the measured point of sight to the observer's point of sight judging section 250 and line of sight coincidence judging section 280. The observer's position measuring section 270 measures the position of the observer 910 within the predetermined image-capturing target area of the image-capturing section 200. The observer's position measuring section 270 supplies information indicating the measured position of the observer 910 to the observer's point of sight judging section 250 and line of sight coincidence judging section 280. The observed person's position measuring section 212 measures the position at which the observed person 915 is present within the image-capturing target area. The observed person's position measuring section 212 supplies information indicating the measured position of the observed person 915 to the observer's point of sight judging section 250 and line of sight coincidence judging section 280.

The observer's point of sight judging section 250 judges whether the point of sight of the observer 910 which is received from the observer's point of sight measuring section 210 is present within a predetermined area. Here, the predetermined area may be the area occupied by the observed person 915, an area corresponding to the eyes of the observed person 915 or the like. To be specific, the observer's point of sight judging section 250 judges whether the point of sight of the observer 910 is present within the predetermined area, based on the measurement results received from the observer's point of sight measuring section 210, observer's position measuring section 270, observed person's point of sight measuring section 214, and observed person's position measuring section 212. The observer's point of sight judging section 250 supplies, to the image storing section 320, information indicating the point of sight of the observer 910 which is measured by the observer's point of sight measuring section 210, and one of information indicating that the point of sight of the observer 910 is present within the predetermined area and information indicating that the point of sight of the observer 910 is not present within the predetermined area.

The line of sight coincidence judging section 280 judges whether the lines of sight of the observer 910 and observed person 915 coincide with each other based on the point of sight of the observed person 915 which is measured by the observed person's point of sight measuring section 214 and the point of sight of the observer 910 which is measured by the observer's point of sight measuring section 210. Specifically speaking, the line of sight coincidence judging section 280 judges whether the point of sight of the observer 910 is present within the area corresponding to the eyes of the observed person 915 based on the measurement results supplied by the observed person's position measuring section 212 and observer's point of sight measuring section 210. For example, the line of sight coincidence judging section 280 judges whether the coordinate indicating the point of sight of the observer 910 is included in the area corresponding to the eyes of the observed person 915 which is defined by a plurality of coordinates. In the same manner, the line of sight coincidence judging section 280 judges whether the point of sight of the observed person 915 is present within the area corresponding to the eyes of the observer 910 based on the measurement results supplied by the observer's position measuring section 270 and observed person's point of sight measuring section 214. When the point of sight of the observer 910 is present within the area corresponding to the eyes of the observed person 915 and the point of sight of the observed person 915 is present within the area corresponding to the eyes of the observer 910, the line of sight coincidence judging section 280 judges that the lines of sight of the observer 910 and observed person 915 coincide with each other. The line of sight coincidence judging section 280 supplies the result of the judgment to the image storing control section 260. In this case, the line of sight coincidence judging section 280 may supply the judgment result to the image storing control section 260 as observed person's point of sight position information.

The image storing control section 260 obtains the image of the observed person 915 from the image-capturing section 200, and supplies the obtained image to the image storing section 320. The image storing control section 260 also supplies the judgment result from the line of sight coincidence judging section 280 to the image storing section 320. The observation result input section 610 is used to input the result of the observation on the observed person 915 done by the observer 910. Here, the observation result may be a disease, and the disease input through the observation result input section 610 is a name of a disease, for example. The observation result input section 610 may be used to input information indicating the symptom of the disease observed by the observer 910. When the observer 910 judges that the observed person 915 does not suffer from a disease, the observation result input section 610 is used to input information indicating that no disease is found, as the result of the observation conducted on the observed person 915 by the observer 910. The observation result input section 610 supplies the input disease to the observation result storing control section 650. The observation result storing control section 650 supplies the disease input through the observation result input section 610 to the image storing section 320.

The image input section 602 is used to input an image of a person under observation. The image input section 602 may be used to input the image of the observed person 915 which is captured by the image-capturing section 200. Here, the person under observation may be an observed person 915 who is to be newly observed by the observer 910. Meanwhile, the observed person 915 may be a person who has already been observed by the observer 910 and whose image has already been stored on the image storing section 320. The image input section 602 may be used to input an image of the person under observation which is captured when the person does not suffer from a disease, and an image of the person under observation which is obtained by the image-capturing section 200 when the observer 910 observes the new observed person 915. The image input section 602 supplies the input image of the person under observation to the physical status calculating section 725. The disease information input section 604 is used to input information indicating a disease. Specifically speaking, the disease information input section 604 is used by the observer 910 to input information indicating a disease of the observed person 915. The disease information input section 604 supplies the information indicating the disease of the observed person 915 to the quantified data extracting section 730.

The image storing section 320 stores thereon the disease received from the observation result input section 610 and the observer's point of sight position information indicating the point of sight of the observer 910 which is measured by the observer's point of sight measuring section 210, in association with the image of the observed person 915 which is captured by the image-capturing section 200. Here, the observer's point of sight position information may indicate the result of the judgment made by the line of sight coincidence judging section 280, that is to say, the observed person's point of sight position information, and whether the observer 910 looks at the observed person 915. The image storing section 320 further stores thereon information indicating that no disease is found which is input through the observation result input section 610 in association with the image of the observed person 915 which is captured by the image-capturing section 200. The image storing section 320 supplies the observer's point of sight position information to the observer's point of sight position judging section 705. Also, the image storing section 320 supplies the image of the observed person 915 to the image extracting section 710 and physical status quantifying section 715.

Based on the observer's point of sight position information which is stored on the image storing section 320, the observer's point of sight position judging section 705 judges whether the observer 910 looks at the observed person 915 when the image of the observed person 915, which is stored on the image storing section 320 in association with the observer's point of sight position information, is captured. To be specific, the observer's point of sight position judging section 705 may judge that the observer 910 looks at the observed person 915, if the point of sight of the observer 910 which is indicated by the observer's point of sight position information is present within the area of the observed person 915. The observer's point of sight position judging section 705 supplies, to the image extracting section 710, the observer's point of sight position information when judging that the observer 910 looks at the observed person 915. When receiving, from the image storing section 320, the observer's point of sight position information indicating that the line of sight coincidence judging section 280 judges that the lines of sight of the observer 910 and observed person 915 coincide with each other, the observer's point of sight position judging section 705 supplies the received the observer's point of sight position information to the image extracting section 710.

The image extracting section 710 extracts an image of the observed person 915 which is stored on the image storing section 320 in association with the observer's point of sight position information received from the observer's point of sight position judging section 705. The image extracting section 710 may extract a plurality of images of the observed person 915 which are stored on the image storing section 320 in association with the observer's point of sight position information. Specifically speaking, the image extracting section 710 extracts an image of the observed person 915 which is captured at a time that precedes, by a predetermined time period, the image-capturing time at which the image of the observed person 915, which is stored on the image storing section 320 in association with the observer's point of sight position information, is captured, and an image of the observed person 915 which is captured when a predetermined time period elapses after the image-capturing time. For example, the image extracting section 710 may extract a plurality of images of the observed person 915 which are captured within a predetermined period of time that is defined with respect to the image-capturing time at which the image of the observed person 915 which is stored in association with the observer's point of sight position information is captured. The image extracting section 710 supplies the extracted images to the physical status quantifying section 715.

The physical status quantifying section 715 analyzes the plurality of images of the observed person 915 extracted by the image extracting section 710, for each of the diseases stored on the image storing section 320 in association with the images of the observed person 915 received from the image extracting section 710. The physical status quantifying section 715 quantifies the physical status of the observed person 915. Here, the physical status of the observed person 915 may include information regarding the observed person 915, for example, the size of the pupil, the point of sight, the number of blinks measured within a predetermined time period, twitching of the eyelids or face, the color of the face, the temperature of the face, the sag of the cheeks, swelling of the face, and the condition of the skin (a rash and the like). Specifically speaking, the physical status quantifying section 715 quantifies a change in the physical status while the observer 910 observes the observed person 915, by comparing the plurality of images of the observed person 915 which are captured within a predetermined period of time. When the observer 910 observes a plurality of observed persons, the physical status quantifying section 715 quantifies a change of the physical status of each of the observed persons, and calculates the average value for the quantified changes.

For example, the image extracting section 710 extracts an image of the observed person 915 which is captured when the observer's point of sight position judging section 705 judges that the observer 910 looks at the area corresponding to the eyes of the observed person 915, and an image of the observed person 915 which is captured when a predetermined time period has elapsed after the time at which the above image is captured. The physical status quantifying section 715 compares the images extracted by the image extracting section 710 in terms of the size of the pupil of the observed person 915, to calculate the change in the size of the pupil. Subsequently, the physical status quantifying section 715 quantifies the calculated change in the size of pupil. For example, the physical status quantifying section 715 may calculate, as the change in the size of the pupil, the rate of change from the size of the pupil of the observed person 915 which is detected at the time at which the observer 910 looks at the area corresponding to the eyes of the observed person 915 to the size of the pupil of the observed person 915 which is detected when a predetermined time period has elapsed, with the former size being used as a reference. Subsequently, the physical status quantifying section 715 calculates an average value of the changes calculated for the plurality of observed persons. The physical status quantifying section 715 may also quantify the change in the position of the point of sight of the observed person 915 and the change in the number of blinks.

Furthermore, for each of the diseases stored on the image storing section 320 in association with the images of the observed person 915 which are extracted by the image extracting section 710, the physical status quantifying section 715 compares the image of the observed person 915 which is stored on the image storing section 320 in association with the disease, with the image of the observed person 915 which is stored on the image storing section 320 in association with information indicating that the disease is not found. The physical status quantifying section 715 may quantify the difference in the physical status of the observed person 915 based on the result of the comparison, to calculate physical status difference quantified data. The physical status quantifying section 715 may obtain the difference in the size of the pupil by comparing the physical statuses shown by the observed person 915 when the observed person 915 suffers from a disease and does not, and quantify the obtained difference, to generate physical status difference quantified data.

The physical status quantifying section 715 may obtain the difference in the size of the pupil of the observed person 915 by comparing the sizes of the pupil shown when the observed person 915 suffers from a disease and does not, and quantify the obtained difference. In addition, the physical status quantifying section 715 may obtain a difference in change of the position of the point of sight of the observed person 915 between when the observed person 915 suffers from a disease and when the observer person 915 does not suffer from the disease, and quantify the obtained difference. Also, the physical status quantifying section 715 may obtain a difference in the number of blinks of the observed person 915 between when the observed person 915 suffers from a disease and when the observed person 915 does not suffer from the disease, and quantify the obtained difference. The physical status quantifying section 715 quantifies the physical statuses of the plurality of observed persons, and calculates an average value based on the total of the quantified physical statuses. The physical status quantifying section 715 may use the calculated average value as physical status quantified data. The physical status quantifying section 715 supplies the physical status quantified data and the physical status difference quantified data to the physical status data storing section 720.

The physical status data storing section 720 stores thereon, for each disease, the physical status quantified data received from the physical status quantifying section 715. The physical status data storing section 720 supplies the physical status quantified data to the quantified data extracting section 730, physical status comparing section 735, and likely disease output control section 750. The physical status calculating section 725 analyzes the image of the person under observation which is received from the image input section 602, to calculate and quantify the physical status of the person under observation. Specifically speaking, the physical status calculating section 725 quantifies the physical status of the person under observation. The physical status calculating section 725 may also have a function as a physical status difference calculating section for calculating the difference in physical status of the person under observation by analyzing the image of the person under observation which is captured when the person does not suffer from a disease and received from the image input section 602 and a newly captured image of the person under observation.

To be specific, the physical status calculating section 725 quantifies the physical status of the person under observation shown in the image of the person under observation, by analyzing a plurality of images of the person under observation which are received from the image input section 602. In more detail, the physical status calculating section 725 may quantify the physical status, by comparing the images of the person under observation which are captured within a predetermined period of time in the chronological order. For example, the physical status calculating section 725 may calculate the number of blinks of the person under observation within a predetermined period of time, and use the calculated number as the quantified physical status. The physical status calculating section 725 supplies the information indicating the quantified physical status of the person under observation to the physical status comparing section 735.

The physical status comparing section 735 compares the information indicating the physical status of the person under observation which is received from the physical status calculating section 725, with the physical status quantified data stored on the physical status data storing section 720. The physical status comparing section 735 may calculate a coincidence level as the result of the comparison. To be specific, the physical status comparing section 735 compares the information indicating the quantified physical status which is received from the physical status calculating section 725, with the physical status quantified data stored on the physical status data storing section 720. For example, the physical status comparing section 735 may calculate a coincidence level, with an assumption that the maximum coincidence level is achieved when the information indicating the quantified physical status which is received from the physical status calculating section 725 coincides with the physical status quantified data stored on the physical status data storing section 720. The physical status comparing section 735 may also has a function of a physical status difference comparing section for comparing the difference in physical status of the person under observation which is calculated by the physical status calculating section 725 with the physical status difference quantified data stored on the physical status data storing section 720. The physical status comparing section 735 supplies the result of the comparison to the likelihood calculating section 740 and likely disease output control section 750.

The likelihood calculating section 740 calculates the likelihood of each disease based on the coincidence level indicated by the result of the comparison done by the physical status comparing section 735. To be specific, the likelihood calculating section 740 judges a disease for which the result of the comparison done by the physical status comparing section 735 shows the highest coincidence level, to be the most likely disease which the person under observation may suffer from. For example, the likelihood calculating section 740 calculates a likelihood of 100% or the like for the most likely disease. The likelihood calculating section 740 may judge a plurality of diseases for which the result of the comparison done by the physical status comparing section 735 shows a higher coincidence level than a predetermined level, to be likely diseases which the person under observation may suffer from. The likelihood calculating section 740 supplies the calculated likelihood to the likely disease output control section 750. The likely disease output control section 750 causes the output section 50 to output information indicating a disease stored on the physical status data storing section 720 in association with the physical status quantified data which shows a higher coincidence level than a predetermined level according to the result of the comparison done by the physical status comparing section 735.

The quantified data extracting section 730 extracts physical status quantified data which is stored on the physical status data storing section 720 in association with information indicating the disease input through the disease information input section 604. The quantified data extracting section 730 supplies the extracted physical status quantified data to the disease image generating section 745. The disease image generating section 745 generates an image of a patient suffering from the disease indicated by the information input through the disease information input section 604, based on the physical status quantified data received from the quantified data extracting section 730. To be specific, the disease image generating section 745 may include therein a disease template image storing section storing thereon template images each uniquely defined for a patient suffering from a certain disease. The disease template image storing section stores thereon template images each showing a patient suffering from a certain disease. The template image stored on the disease template image storing section may be a still or moving image showing a patient suffering from a certain disease.

The disease image generating section 745 extracts a template image which is stored on the disease template image storing section in association with the disease indicated by the information input through the disease information input section 604. Subsequently, the disease image generating section 745 generates an image of a patient suffering from the disease, based on the physical status indicated by the physical status quantified data received from the quantified data extracting section 730 and the extracted template image. Here, the disease image generating section 745 may generate a moving image showing the patient suffering from the disease. For example, for a certain disease, the physical status shown by a patient with the disease is a change in position of the point of sight within a predetermined period of time. In this case, the disease image generating section 745 generates a moving image showing the patient with the disease who moves the line of sight based on the template image and the change in the position of the point of sight which is indicated by physical status quantified data. The image output control section 755 causes the output section 50 to output the image generated by the disease image generating section 745.

From the perspective of privacy, it may not be allowed to record an image of the person 917 with a disease in a digital format. According to the present embodiment, however, it is not necessary to record the image of the patient suffering from a disease. Alternatively, the present embodiment can generate the image of the patient suffering from a disease based on the physical status quantified data calculated by the physical status calculating section 725 and a template image provided in advance.

Under the control of the likely disease output control section 750, the output section 50 outputs information indicating a disease which is stored on the physical status data storing section 720 in association with physical status quantified data which shows a higher coincidence level than a predetermined level according to the result of the comparison done by the physical status comparing section 735. For example, the output section 50 outputs the name of a disease which the person under observation is most likely to suffer from, which is identified as a result of the comparison done, by the physical status comparing section 735, between the change in the position of the point of sight and physical status quantified data indicating a change in the position of the point of sight. The output section 50 may output information indicating a plurality of disease, together with the respective likelihoods of the plurality of diseases which are calculated by the likelihood calculating section 740. To be specific, the output section 50 outputs the names, symptoms and other relating information of the diseases in descending order of likelihood. In addition, the output section 50 outputs the image generated by the disease image generating section 745, which is received from the image output control section 755. The output section 50 may output information indicating a disease which is stored on the physical status data storing section 720 in association with physical status difference quantified data that shows a higher coincidence level than a predetermined level according to the result of the comparison done by the physical status difference comparing section.

The image recording apparatus 10 relating to the present embodiment quantifies the physical status of the observed person 915 when the observer 910 observes the observed person 915, and records the quantified physical status. Therefore, the image recording apparatus 10 can compare the physical status of a newly observed person under observation with the quantified physical status that has been recorded thereon, to output information indicating a disease which the person under observation is likely to suffer from. In this way, the image recording apparatus 10 can assist the observer 910 to identify an accurate disease when the observer 910 observes the observed person 915.

Also, when input with a name of a disease, the image recording apparatus 10 relating to the present embodiment can generate an image showing a patient suffering from the disease corresponding to the input name based on the image of the observed person 915 or person under observation and the physical status quantified data obtained by quantifying the physical status of the observed person 915 or person under observation. In this way, the user of the image recording apparatus 10 can learn how to observe the observed person 915 in terms of diseases by comparing the generated image and the observed person 915 or person under observation.

The image recording apparatus 10 relating to the present embodiment includes therein the observer's point of sight position judging section 705. In other embodiments, however, the image recording apparatus 10 may forgo the observer's point of sight position judging section 705, and be configured in such a manner that the observer's point of sight judging section 250 has a function of the observer's point of sight position judging section 705. If such is the case, the observer's point of sight judging section 250 judges whether the observer looks at the observed person when the image of the observed person is captured, and the image extracting section extracts an image of the observed person for which the observer's point of sight judging section 250 makes positive judgment.

Figure 29:
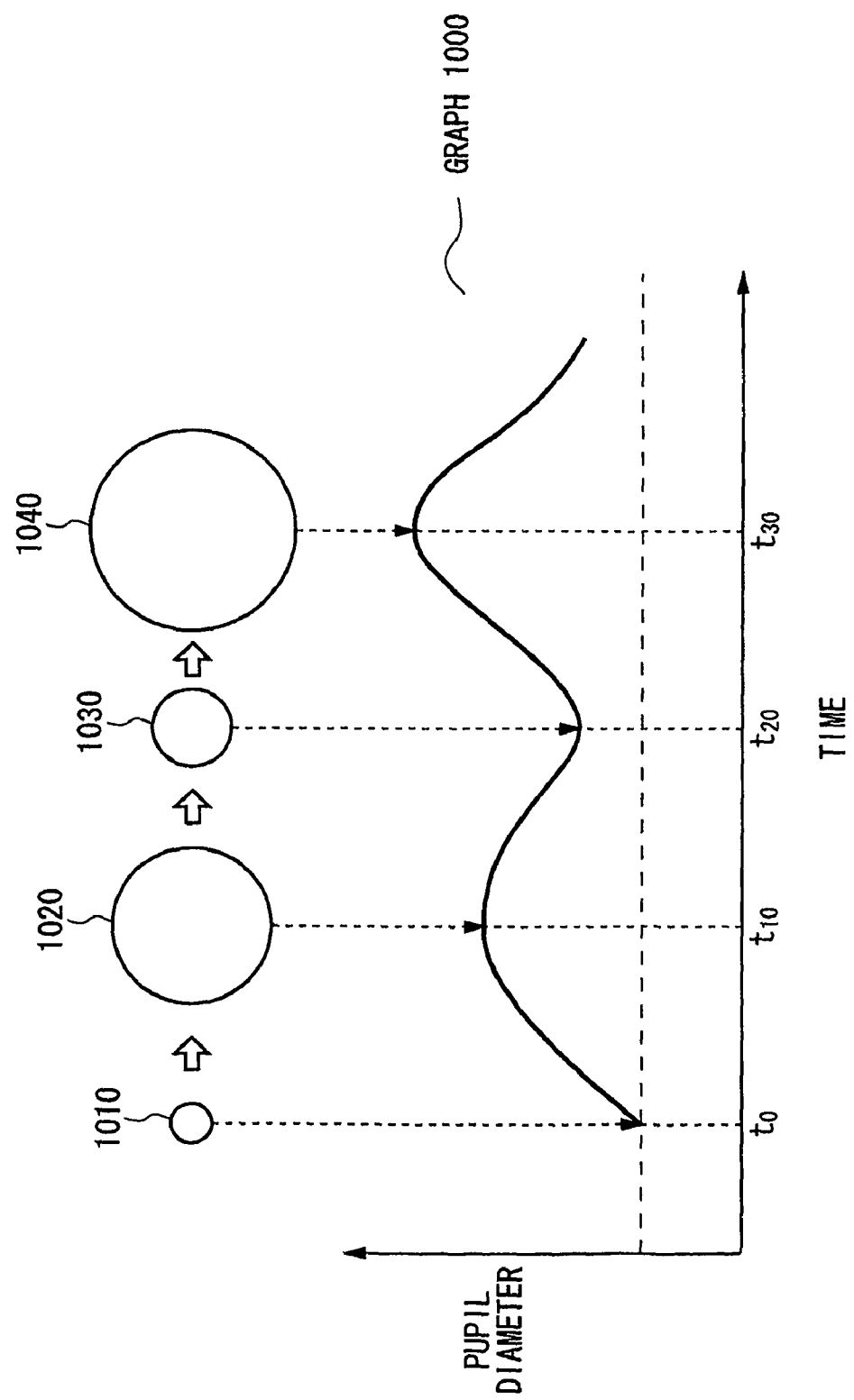
FIG. 29 is used to illustrate the function of a physical status calculating section 725.

FIG. 29 illustrates an exemplary function of the physical status calculating section 725 relating to the present embodiment. Here, the physical status calculating section 725 may also has a function of a physical status difference calculating section for calculating a difference in the physical status of a person under observation by comparing an image of the person under observation which is captured when the person does not suffer from a disease and received from the image input section 602 and an image of the person under observation which is newly captured.

To begin with, the physical status calculating section 725 analyzes the image of the person under observation which is received from the image input section 602. For example, the physical status calculating section 725 analyzes the size of the pupil of the person under observation based on images captured within a predetermined period of time, that is to say, a time period from the time t0 to the time t30 as shown in a graph 1000. For example, the physical status calculating section 725 analyzes and identifies the pupil diameters of pupils 1010, 1020, 1030 and 1040 of the person under observation at the times t0, t10, t20 and t30. The physical status calculating section 725 calculates a change in pupil diameter for the times t10, t20 and t30 with respect to the pupil diameter at the time t0, and adds together the calculated changes. Subsequently, the physical status calculating section 725 may use the result of the addition as the physical status of the person under observation.

FIG. 30 illustrates an exemplary structure of data stored on the physical status data storing section 720 relating to the present embodiment. The physical status data storing section 720 stores thereon a plurality of pieces of physical status quantified data in a one-to-one correspondence with a plurality of diseases. The physical status quantified data may include pieces of data generated by quantifying values such as a change in the size of the pupil of the observed person 915, a change in the position of the point of sight, a change in the number of blinks within a predetermined period of time, and a change in twitching of the eyelids or face. For example, the physical status data storing section 720 stores thereon a plurality of pieces of data indicating the movement of the eyes of the observed person 915 in association with each disease. The plurality of pieces of data includes line of sight data indicating a change in the position of the point of sight, pupil data indicating a change in the size of the pupil, and blink data indicating a change in the number of blinks. The physical status data storing section 720 may store thereon, for each disease, physical status quantified data obtained by the physical status quantifying section 715. For example, the physical status data storing section 720 stores thereon, for a disease 780, pieces of physical status quantified data respectively in the sections of line of sight data, pupil data, and blink data.

Referring to the pieces of physical status quantified data for the disease 780, the values indicated decrease in the order of the line of sight data, blink data and pupil data. This means that, when the observed person 915 is observed in terms of the disease 780, the observation can be conducted with a focus on the line of sight data. By exclusively looking at the pieces of line of sight data stored on the physical status data storing section 720, the values of the pieces of physical status quantified data decrease in the order of the diseases 780, 782, and 784. Therefore, the physical status comparing section 735 can judge which one of the diseases 780, 782 and 784 is most likely, by comparing physical status quantified data obtained by quantifying a change in the position of the point of sight, with the pieces of physical status quantified data (i.e. the pieces of line of sight data) stored on the physical status data storing section 720. For example, the physical status comparing section 735 calculates the likelihoods of the diseases by dividing the pieces of physical status quantified data (the pieces of line of sight data) stored on the physical status data storing section 720 by the physical status quantified data (the line of sight data) received from the physical status calculating section 725. The physical status comparing section 735 then supplies, to the likely disease output control section 750, a name of the disease which shows the highest likelihood according to the result of the calculation. The likely disease output control section 750 outputs the received name of the disease to the output section 50.

It should be noted that the image recording apparatus 10 relating to the present invention can be utilized not only for the observation in the medical field but also in the fields of beauty treatment and sports, for example. When the image recording apparatus 10 is applied in the areas of beauty treatment and sports, the term "disease" is used in a broader sense than "illness" or "sickness". For example, when the image recording apparatus 10 relating to the present invention is used in the area of beauty treatment, a disease indicates an observation result unfavorable for the user, such as wrinkles, rough skin, and the like. When the image recording apparatus 10 relating to the present invention is used in the area of sports, a disease indicates incorrect form and a bad habit in each type of sports.

When the image recording apparatus 10 relating to the present invention is used in the beauty treatment field, the image storing section 320 stores thereon images showing different areas of a human body which have changed with advancing age. The physical status quantifying section 715 calculates the characteristics of the diseases such as "wrinkles", "pigmented spots", and "rough skin" based on image processing, to determine the types of diseases, for example. The physical status quantifying section 715 also quantifies the degree of aging which is indicated by the diseases such as "wrinkles", "pigmented spots", and "rough skin". The observation result input section 610 is used to input, as the observation result indicating a disease, a result of observing the observed person in terms of beauty treatment, such as "the person has wrinkles" or "the person has a rough skin". The physical status calculating section 725 quantifies an input image of a person under observation in the same manner as the physical status quantifying section 715. The physical status comparing section 735 compares the quantified data of the person under observation with the data stored on the physical status data storing section 720, to determine the degree of the wrinkles or skin roughness of the person under observation.

The disease image generating section 745 may prestore thereon, as the template images, the images showing different areas of the human body which have changed with advancing age. For example, the disease image generating section 745 prestores thereon "an image showing the outer corner of the eye of a female in her teens", "an image showing the outer corner of the eye of a female in her twenties", "an image showing the skin of a female in her teens", "an image showing the skin of a female in her forties" and the like. The physical status calculating section 725 calculates the characteristics of diseases based on an input image of a person under observation. Based on the result, the template images stored on the disease image generating section 745 may be changed. In this manner, the output section 50 may display diseases the person under observation is likely to suffer from in the future. For example, the output section 50 displays an image showing wrinkles the person under observation may possibly have in five years' time without beauty treatment. As described above, the image recording apparatus 10 can be used to identify symptoms of a patient, when used in the area of beauty treatment.

When the image recording apparatus 10 relating to the present invention is used in the sports field, the image storing section 320 stores thereon moving images showing forms corresponding to different advancement levels of a certain sport. Here, the following description is made using the hitting forms in baseball as an example. The physical status quantifying section 715 calculates, based on image processing, the characteristics of incorrect forms, such as "hitting only with the force of the hands", "the hitter does not lower the chin" and "the hitter does not keep an eye on the ball", so as to determine the features of the forms. The physical status quantifying section 715 may quantify the degree of the incorrectness of the forms. The observation result input section 610 is used to input, as the observation result indicating a disease, the result of observing the observed person such as "hitting only with the force of the hands", "the hitter does not lower the chin" and "the hitter does not keep an eye on the ball". The physical status calculating section 725 quantifies an input moving image of a person under observation in the same manner as the physical status quantifying section 715. The physical status comparing section 735 compares the quantified data of the person under observation with the data stored on the physical status data storing section 720, to determine the degree of the incorrectness of the form of the person under observation. As described above, the image recording apparatus 10 can be used to identify the habit of a player, when used in the area of sports.

Figure 31:
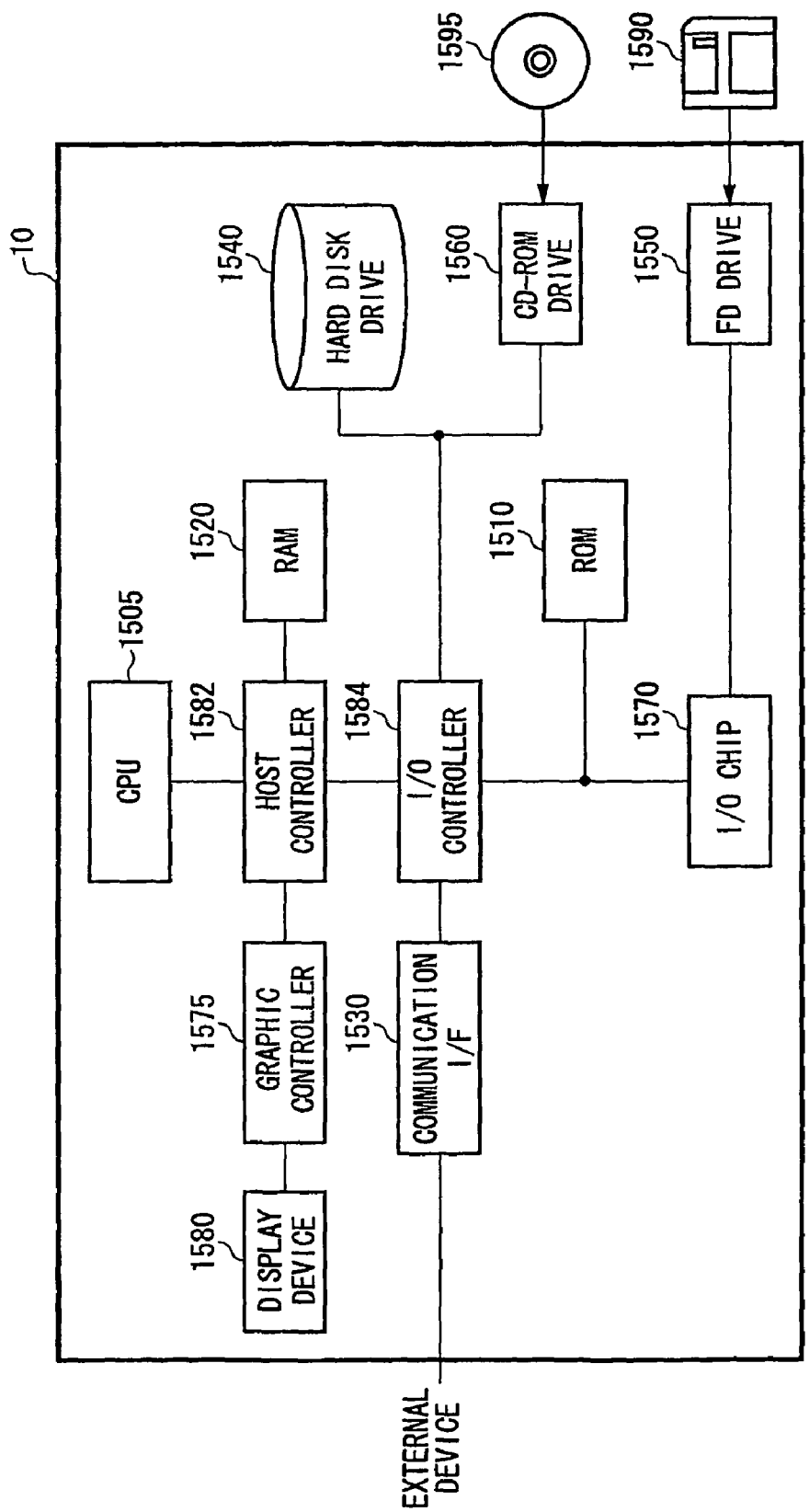
FIG. 31 is a block diagram illustrating the hardware configuration of the image recording apparatus 10.

FIG. 31 illustrates an exemplary hardware configuration of the image recording apparatus 10 relating to the present invention. The image recording apparatus 10 is constituted by a CPU surrounding section, an input/output (I/O) section and a legacy I/O section. The CPU surrounding section includes a CPU 1505, a RAM 1520, a graphic controller 1575, and a display device 1580 which are connected to each other by means of a host controller 1582. The I/O section includes a communication interface 1530, a hard disk drive 1540, and a CD-ROM drive 1560 which are connected to the host controller 1582 by means of an I/O controller 1584. The legacy I/O section includes a ROM 1510, a flexible disk drive 1550, and an I/O chip 1570 which are connected to the I/O controller 1584.

The host controller 1582 connects the RAM 1520 with the CPU 1505 and graphic controller 1575 which access the RAM 1520 at a high transfer rate. The CPU 1505 operates in accordance with programs stored on the ROM 1510 and RAM 1520, to control the constituents. The graphic controller 1575 obtains image data which is generated by the CPU 1505 or the like on a frame buffer provided within the RAM 1520, and causes the display device 1580 to display the obtained image data. Alternatively, the graphic controller 1575 may include therein a frame buffer for storing thereon image data generated by the CPU 1505 or the like.

The I/O controller 1584 connects, to the host controller 1582, the communication interface 1530, hard disk drive 1540 and CD-ROM drive 1560 which are I/O devices operating at a relatively high rate. The communication interface 1530 communicates with a difference device via a network. The hard disk drive 1540 stores thereon programs and data to be used by the CPU 1505 provided in the image recording apparatus 10. The CD-ROM drive 1560 reads programs and data from a CR-ROM 1595, and supplies the read programs and data to the hard disk drive 1540 via the RAM 1520.

The I/O controller 1584 is also connected to the ROM 1510, flexible disk drive 1550 and I/O chip 1570 which are I/O devices operating at a relatively low rate. The ROM 1510 stores thereon a boot program executed by the image recording apparatus 10 at the start up, programs unique to the hardware of the image recording apparatus 10, and the like. The flexible disk drive 1550 reads programs and data from a flexible disk 1590, and supplies the read programs and data to the hard disk drive 1540 via the RAM 1520. The I/O chip 1570 is used to connect a variety of I/O devices such as the flexible disk drive 1550 via, for example, a parallel port, a serial port, a keyboard port, a mouse port or the like.

An image recording program to be supplied to the hard disk drive 1540 via the RAM 1520 is provided by a user in a state of being stored on a recording medium such as the flexible disk 1590, CD-ROM 1595 and an IC card. The image recording program is read from the recording medium, installed via the RAM 1520 in the hard disk drive 1540 in the image recording apparatus 10, and executed by the CPU 1505. The image recording program to be installed in and thus executed by the image recording apparatus 10 causes the CPU 1505 and the like to operate the image recording apparatus 10 as the image-capturing unit 20, storing unit 30, sound unit 40, output section 50, input unit 60 and analyzing unit 70 and the constituents of these units and section 20 to 70 described with reference to FIGS. 1 to 30.

While the embodiments of the present invention have been described, the technical scope of the invention is not limited to the above described embodiments. It is apparent to persons skilled in the art that various alternations and improvements can be added to the above-described embodiment. It is also apparent from the scope of the claims that the embodiments added with such alternations or improvements can be included in the technical scope of the invention.

What is claimed is:

1. An image output apparatus for assisting an observer who observes an observed person, comprising:
    an image-capturing section that captures an image of the observed person;
    an observer's point of sight measuring section that measures a point of sight of the observer when the image-capturing section captures the image of the observed person;
    an output section that outputs the image of the observed person which is captured by the image-capturing section; and
    a point of sight output control section that causes the output section to output information indicating the point of sight of the observer which is measured by the observer's point of sight measuring section, together with the image of the observed person which is captured by the image-capturing section; and
    further comprising:
    an observed person's information storing section that stores the image of the observed person which is captured by the image-capturing section in association with the observed person; and
    a previous image output control section that, when the image-capturing section captures a new image of the observed person, causes the output section to output a previous image of the observed person which is stored on the observed person's information storing section in association with the observed person, together with the new image of the observed person which is captured by the image-capturing section, while the observer observes the observed person, wherein
    the observed person's information storing section further stores the point of sight of the observer which is measured by the observer's point of sight measuring section in association with the observed person, and
    the previous image output control section causes the output section to output, side by side, both the new image of the observed person with information indicating the observer's point of sight when the new image was captured and the previous image of the observed person with information indicating the point of sight of the observer when the previous image of the observed person was captured.

2. The image output apparatus as set forth in claim 1, wherein
    the point of sight output control section causes the output section to output a mark indicating the point of sight of the observer which is measured by the observer's point of sight measuring section, in such a state that the mark is overlapped onto the image of the observed person which is captured by the image-capturing section.

3. The image output apparatus as set forth in claim 1, further comprising
    a point of sight image extracting section that extracts a partial image including the point of sight of the observer which is measured by the observer's point of sight measuring section, from the image of the observed person which is captured by the image-capturing section, wherein
    the point of sight output control section causes the output section to output an image obtained by enlarging the partial image extracted by the point of sight image extracting section, together with the image of the observed person which is captured by the image-capturing section.

4. The image output apparatus as set forth in claim 3, further comprising
    a view measuring section that measures a view of the observer, wherein
    the point of sight image extracting section extracts an image corresponding to the view of the observer which is measured by the view measuring section, from the image of the observed person which is captured by the image-capturing section.

5. The image output apparatus as set forth in claim 1, further comprising:
    a sound recording section that records sound information of the observer when the image-capturing section captures the image of the observed person;
    an image storing section that stores the sound information of the observer which is recorded by the sound recording section, in association with the image of the observed person which is captured by the image-capturing section;
    a sound information comparing section that compares sound information of the observer which is newly recorded by the sound recording section with the sound information of the observer which is previously recorded by the sound recording section and stored on the image storing section; and
    a previous image extracting section that extracts, based on a result of the comparison done by the sound information comparing section, a previous image of the observed person which is stored on the image storing section in association with previous sound information of the observer which shows a higher coincidence level than a predetermined level with the sound information of the observer which is newly recorded by the sound recording section, wherein
    the previous image output control section causes the output section to output the previous image of the observed person which is extracted by the previous image extracting section, together with the new image of the observed person which is captured by the image-capturing section.

6. The image output apparatus as set forth in claim 1, wherein
    the output section is a display section,
    the image output apparatus further comprises:
    an observed person's information storing section that stores the image of the observed person which is captured by the image-capturing section in association with the point of sight of the observer which is measured by the observer's point of sight measuring section;

a previous image output control section that reads the image of the observed person which is stored on the observed person's information storing section, and causes the display section to display the read image of the observed person; and a viewer's point of sight measuring section that measures a point of sight of a viewer who views the image of the observed person which is displayed on the display section, wherein the observed person's information storing section further stores information indicating the point of sight of the viewer which is measured by the viewer's point of sight measuring section, in association with the image of the observed person which is read by the previous image output control section.

7. The image output apparatus as set forth in claim 6, further comprising:

a viewer's point of sight judging section that judges whether the point of sight of the observer which is measured by the observer's point of sight measuring section coincides with the point of sight of the viewer which is measured by the viewer's point of sight measuring section; and a viewed image extracting section that, when the viewer's point of sight judging section judges negatively, extracts an image corresponding to information indicating that the points of sight do not coincide with each other, wherein the previous image output control section causes the output section to output the image which corresponds to the information indicating that the points of sight do not coincide with each other and is thus extracted by the viewed image extracting section.

8. The image output apparatus as set forth in claim 7, wherein the viewer's point of sight judging section judges that the point of sight of the observer which is measured by the observer's point of sight measuring section does not coincide with the point of sight of the viewer which is measured by the viewer's point of sight measuring section, when the point of sight of the viewer is not present within a predetermined region including the point of sight of the observer.

9. The image output apparatus as set forth in claim 7, wherein when the point of sight of the observer which is measured by the observer's point of sight measuring section moves to a plurality of different positions, the viewer's point of sight judging section judges that the point of sight of the observer coincides with the point of sight of the viewer which is measured by the viewer's point of sight measuring section if the point of sight of the viewer moves to vicinities which respectively correspond to the plurality of different positions.

10. The image output apparatus as set forth in claim 9, wherein the viewer's point of sight judging section judges that the point of sight of the observer coincides with the point of sight of the viewer if the point of sight of the viewer which is measured by the viewer's point of sight measuring section moves to the vicinities in a same order as the point of sight of the observer.

11. The image output apparatus as set forth in claim 8, wherein the viewer's point of sight judging section judges that the point of sight of the observer coincides with the point of sight of the viewer if the point of sight of the observer which is measured by the observer's point of sight measuring section and the point of sight of the viewer which is measured by the viewer's point of sight measuring section are both present in a predetermined region of the image of the observed person which is captured by the image-capturing section.

12. The image output apparatus as set forth in claim 11, wherein the predetermined region of the image includes at least one of an eye, a mouth and a hand of the observed person.

13. The image output apparatus as set forth in claim 6, wherein the point of sight output control section causes the output section to output at least one of (i) a mark indicating a position of the point of sight of the observer which is measured by the observer's point of sight measuring section and (ii) a mark indicating a position of the point of sight of the viewer which is measured by the viewer's point of sight measuring section, in such a state that the at least one of the marks is overlapped onto the image of the observed person.

14. An image output method for assisting an observer who observes an observed person, comprising:

capturing an image of the observed person;

measuring a point of sight of the observer during the image capturing; and outputting information indicating the point of sight of the observer which is measured in the point of sight measuring, together with the image of the observed person which is captured in the image capturing; and further comprising:

storing the image of the observed person which is captured by the image-capturing step in association with the observed person; and when the image-capturing step captures a new image of the observed person, outputting a previous image of the observed person which is stored in association with the observed person, together with the new image of the observed person which is captured by the image-capturing step, while the observer observes the observed person, wherein the observed person's information storage further includes storing the point of sight of the observer which is measured by the observer's point of sight in association with the observed person, and outputting, side by side, both the new image of the observed person with information indicating the observer's point of sight when the new image was captured and the previous image of the observed person with information indicating the point of sight of the observer when the previous image of the observed person was captured.

15. A non-transitory computer readable medium storing an image output program for an image output apparatus that assists an observer who observes an observed person, the image output program causing the image output apparatus to function as:

an image-capturing section that captures an image of the observed person;

an observer's point of sight measuring section that measures a point of sight of the observer when the image-capturing section captures the image of the observed person;

an output section that outputs the image of the observed person which is captured by the image-capturing section; and a point of sight output control section that causes the output section to output information indicating the point of sight of the observer which is measured by the observer's point of sight measuring section, together with the image of the observed person which is captured by the image-capturing section; and further comprising:

an observed person's information storing section that stores the image of the observed person which is captured by the image-capturing section in association with the observed person; and a previous image output control section that, when the image-capturing section captures a new image of the observed person, causes the output section to output a previous image of the observed person which is stored on the observed person's information storing section in association with the observed person, together with the new image of the observed person which is captured by the image-capturing section, while the observer observes the observed person, wherein the observed person's information storing section further stores the point of sight of the observer which is measured by the observer's point of sight measuring section in association with the observed person, and the previous image output control section causes the output section to output, side by side, both the new image of the observed person with information indicating the observer's point of sight when the new image was captured and the previous image of the observed person with information indicating the point of sight of the observer when the previous image of the observed person was captured.

* * * * *